US008889672B2

(12) United States Patent
Antonetti et al.

(10) Patent No.: US 8,889,672 B2
(45) Date of Patent: Nov. 18, 2014

(54) COMPOUNDS, FORMULATIONS, AND METHODS OF PROTEIN KINASE C INHIBITION

(75) Inventors: David A. Antonetti, Ann Arbor, MI (US); Paul Titchenell, Hershey, PA (US)

(73) Assignees: The Regents of The University of Michigan, Ann Arbor, MI (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/458,990

(22) Filed: Apr. 27, 2012

(65) Prior Publication Data
US 2012/0302561 A1    Nov. 29, 2012

Related U.S. Application Data

(60) Provisional application No. 61/480,848, filed on Apr. 29, 2011.

(51) Int. Cl.
| *A61K 31/5377* | (2006.01) |
| *A61P 43/00* | (2006.01) |
| *A61K 31/421* | (2006.01) |
| *A61P 29/00* | (2006.01) |
| *A61P 3/00* | (2006.01) |
| *A61P 35/00* | (2006.01) |
| *A61K 31/381* | (2006.01) |
| *A61K 31/4164* | (2006.01) |
| *A61K 31/496* | (2006.01) |
| *A61K 31/352* | (2006.01) |
| *A61K 31/4436* | (2006.01) |
| *A61K 31/4025* | (2006.01) |
| *A61K 31/4535* | (2006.01) |

(52) U.S. Cl.
CPC ............. *A61K 31/381* (2013.01); *A61K 31/496* (2013.01); *A61K 31/5377* (2013.01); *A61K 31/352* (2013.01); *A61K 31/4436* (2013.01); *A61K 31/4025* (2013.01); *A61K 31/4535* (2013.01)
USPC ........ 514/231.5; 514/447; 514/336; 514/398; 514/377

(58) Field of Classification Search
USPC ........ 514/231.5, 447, 336, 398, 377; 435/184
See application file for complete search history.

(56) References Cited

U.S. PATENT DOCUMENTS

| 7,585,865 B2 | 9/2009 | Antonetti et al. |
| 2008/0021036 A1 | 1/2008 | Antonetti et al. |
| 2009/0258006 A1 | 10/2009 | Weiss et al. |
| 2009/0318462 A1 | 12/2009 | Antonetti et al. |
| 2011/0092566 A1 | 4/2011 | Srivastava et al. |

FOREIGN PATENT DOCUMENTS

| WO | WO2005/033102 | 4/2005 |
| WO | WO2008/002641 | 1/2008 |
| WO | WO2008/124849 | 10/2008 |
| WO | WO2009/049362 | 4/2009 |
| WO | WO2009/124086 | 10/2009 |
| WO | WO2010/032976 | 3/2010 |

OTHER PUBLICATIONS

Berra et al., *EMBO J.*, 14:6157-6163 (1995).
Diaz-Meco et al., *Mol. Cell Biol.*, 21:1218-1227 (2001).
Farese et at., *J. Clin. Invest.*, 117:2289-301 (2007).
Kochs et al., *Eur. J. Biochem.*, 216(2):597-606 (1993).
Lee et al., *Cancer Chemother. Pharmacol.*, 57(6): 761-71 (2006).
Leitges et al., *Mol. Cell*, 8:771-780 (2001).
Martin et al., *EMBO J.*, 21: 4049-4057 (2002).
Mohammed et al., *Mol. Cancer Ther.*, 2(2): 183-188 (2003).
Moscat et al., *EMBO Rep.*, 1(5):399-403 (2000).
Ponting et al., *Trends Biochem. Sci.*, 27:10 (2002).
Rannard and Davis, *Organic Letters*, 2:2117-2120 (2000).
Sajan et al., *Diabetologia*, 52:1197-1207 (2009).
Soler et at., *Carcinogenesis*, 20(8);1425-31 (1999).
Steinberg et al., *Physiol. Rev.*, 88:1341-1378 (2008).
Aveleira et al., "TNF-α signals through PKC ζ/NF-κB to alter the tight junction complex and increase retinal endothelial cell permeability", Diabetes, 59:2872-2882 (2010).
Briel et al., "Substituted 2-aminothiopen-derivatives: a potential new class of GluR6-antagonists", European Journal of Medicinal Chemistry, 45:69-77 (2010).
Galvez et al., "Rubosixtaurin and other pkc inhibitors in diabetic retinopathy and macular Edema. Review", Current Diabetes Reviews, 5:14-17 (2009).
Sharlow et al., "Development and implementation of a miniaturized high-throughput time-resolved fluorescence energy transfer assay to identify small molecule inhibitors of polo-like kinase 1", Assay and Drug Development Technologies, 5:723-735 (2007).
Titchenell et al., "Novel Atypical PKC Inhibitors Prevent Vascular Endothelial Growth Factor-induced blood-retinal barrier dysfunction", Biochemical Journal Immediate Publication, Published Jun. 22, 2012, pp. 1-27.
Partial International Search Report for PCT/US2012/035627 dated Aug. 8, 2012.
International Search Report and Written Opinion for PCT/US2012/035627 dated Oct. 1, 2012.
International Preliminary Report on Patentability for PCT/US2012/035627 dated Jul. 29, 2013.

*Primary Examiner* — San-Ming Hui
*Assistant Examiner* — Kathrien Cruz
(74) *Attorney, Agent, or Firm* — Marshall, Gerstein & Borun LLP

(57) ABSTRACT

The invention provides a method of inhibiting atypical protein kinase C (aPKC) comprising contacting an aPKC with a compound having a structure selected from the group consisting of structural formulas (I) to (IX). The invention further provides a method of inhibiting or reducing vascular permeability. The method comprising administering to a subject a composition comprising an amount of a compound having a structure selected from the group consisting of structural formulas (I) to (IX) effective to inhibit or reduce vascular permeability. A method of treating or preventing a disease or disorder characterized by abnormal vascular permeability, a method of inhibiting angiogenesis, a method of inhibiting cancer cell proliferation, a formulation, and a method of preparing a formulation also are provided.

16 Claims, 10 Drawing Sheets

194-094-001
 194-094-011
 194-094-002
 194-098-005
 194-094-005
 194-092-003
 194-094-007
 194-094-003
 194-094-008
 194-094-009
 PKCzI-diMeO (PKCzI3)
 194-094-010
 PKCzI-diCl 194-080-001

194-084-001

194-086-001

194-082-001

194-054-001

194-074-004

194-074-005

194-074-006

194-074-007

194-074-008

PKCzI-diMeO
(PKCzI3)

5132573

5632675

5311310

5635527

5627112

Apogee B

Apogee A

COMPOUNDS, FORMULATIONS, AND METHODS OF PROTEIN KINASE C INHIBITION

CROSS-REFERENCE TO RELATED APPLICATIONS

This application claims the benefit of priority under 35 U.S.C. §119(e) of U.S. Provisional Patent Application No. 61/480,848, filed Apr. 29, 2011. The disclosure of the priority application is incorporated herein by reference.

STATEMENT OF GOVERNMENT INTEREST

This invention was made with government support under EY012021 and EY016413 awarded by the National Institutes of Health. The government has certain rights in the invention.

OTHER FUNDING

This invention was made with support from Juvenile Diabetes Research Foundation International, grant entitled "Developing Atypical PKC Inhibitors to Treat Diabetic Retinopathy." This invention was also made with support from the Research to Prevent Blindness Foundation.

FIELD OF DISCLOSURE

This disclosure relates to compounds, compositions, and methods for regulating one or more isoforms of protein kinase C (PKC). The disclosure also relates to compounds, compositions, and methods for inhibiting or reducing vascular permeability.

BACKGROUND ON THE INVENTION

Increased vascular permeability contributes to a variety of ailments, including vision threatening retinopathies, such as diabetic retinopathy, macular edema, uveitis, and ischemic retinopathies. Changes in the permeability of the vascular bed in the central nervous system also contribute to the pathology of brain tumors and stroke. Vascular permeability is regulated, at least in part, by tight junctions, seams between cell membranes that form a barrier against passage of materials between cells. Post-translational modification of tight junction proteins, e.g., protein phosphorylation, plays a role in disease progression. For example, diabetes increases expression of vascular endothelial growth factor (VEGF), which alters vascular permeability. VEGF-induced permeability requires the phosphorylation, ubiquitination, and internalization of the tight junction protein occludin in a classical protein kinase C (PKC)-dependent manner.

PKC designates a class of kinases which play central roles in key cell signaling processes such as gene expression and regulation of cell growth. There are numerous isoforms of PKC typically classified as: 1) "calcium-dependent" conventional isoforms ("cPKC") which are regulated by both calcium and diacylglycerol (DAG), such as PKC-beta; 2) "calcium-independent" novel isoforms ("nPKC") which are regulated by DAG but do not require calcium, such as PKC-delta; and 3) "atypical" isoforms ("aPKC") which do not require calcium for activation and which are not regulated by DAG. Atypical PKC isoforms include PKC-zeta and PKC-iota (human) (also called PKC-lambda in mice), and generally consist of five functional domains: a Phox/Bem1 (PB1) domain at the N-terminus, an auto-inhibitory pseudosubstrate domain having 12 amino acids, a modified zinc finger-like C1 domain, an ATP binding domain, and a kinase domain at the C-terminus. The PB1 domain interacts with a variety of other proteins (e.g., partition defective homologue (PAR)-6 and mitogen-activated protein kinase kinase (MEK)) through an octicosapeptide repeat (OPR), Phox and CDC (PC) domain, or the aPKC-interacting domain, collectively termed the OPCA motif (Diaz-Meco et al., *Mol. Cell. Biol.*, 21:1218-1227 (2005); Ponting et al., *Trends Biochem. Sci.*, 27:10 (2002); and Berra et al., *EMBO J.*, 14:6157-6163 (1995))). The pseudosubstrate domain is similar to a PKC phosphorylation site but with an Ala substituted for a Ser which inhibits kinase activity until activation induces a conformational change displacing the auto-inhibitory region. Atypical PKCs function independently of DAG but retain a modified C1 domain containing a cluster of basic residues not seen in cPKCs. Additionally, two residues at the C-terminus, Thr410 for PKC-zeta (Thr412 for PKC-iota) and Thr560 for PKC-zeta (Thr555 for PKC-iota) are phosphorylation sites required for activity (Steinberg et al., *Physiol. Rev.*, 88:1341-1378 (2008)).

Atypical PKC represents a target for interfering with the cascade of events leading to vascular permeability induced by growth factors such as VEGF and inflammatory cytokines. The invention provides compounds, compositions, and methods for inhibiting or reducing vascular permeability and regulating aPKC activity.

SUMMARY OF THE INVENTION

Compositions and methods for inhibiting or reducing vascular permeability are provided. Compositions and methods for inhibiting protein kinase C (PKC) are further provided. In one aspect, the invention includes a method of inhibiting aPKC. A method according to the invention comprises administering to a subject a compound (or the pharmaceutically acceptable salt, hydrate, or prodrug thereof) having a structure selected from the group consisting of structural formula (I):

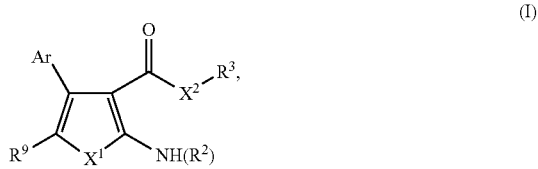

structural formula (II):

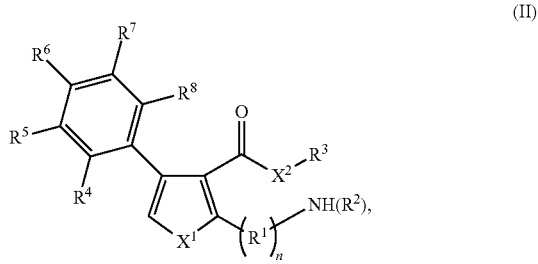

structural formula (III):

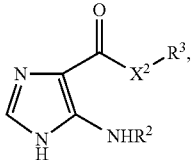

structural formula (IV):

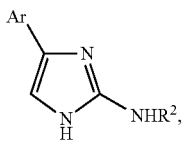

structural formula (V):

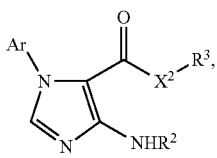

structural formula (VI):

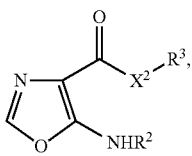

structural formula (VII):

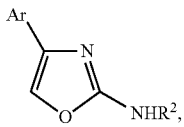

structural formula (VIII):

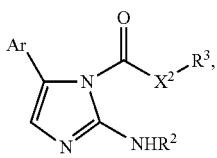

and structural formula (IX):

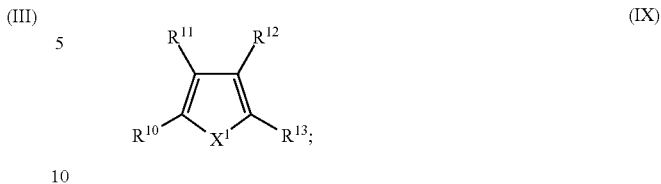

wherein $X^1$ is selected from the group consisting of O, S, NH, and NMe; wherein n has a value of zero (0), one (1), or two (2); wherein $R^1$ is selected from the group consisting of $CH_2$, $CH(CH_3)$, $C(CH_3)_2$, $C_2H_4$, and $C_2H_2$; wherein $R^2$ is selected from the group consisting of H, $CH_3$, $CH_2OH$, $C_2H_5$, $C_2H_5O$, $CH(CH_3)_2$, $C(CH_3)$, $CH_2CH(CH_3)_2$, and $CH_2C(CH_3)_3$; wherein $X^2$ is selected from the group consisting of O, S, NH and N; when $X^2$ is O, S, or NH, $R^3$ is selected from the group consisting of an aryl residue, an alkyl residue having 1 to 10 carbon atoms, an alkoxy residue having 1 to 10 carbon atoms, and a polyglycol residue having two to twelve carbon atoms; when $X^2$ is N, $R^3$ is either two independently selected residues each selected from the group consisting of an aryl residue, an alkyl residue having 1 to 10 carbon atoms, an alkoxy residue having 1 to 10 carbon atoms, and a polyglycol residue having two to twelve carbon atoms; or $X^2$ and $R^3$ are a cyclic group ($X^2$—$R^3$) having five or six members and optionally one or more additional heteroatoms; wherein $R^4$ and $R^8$ are individually selected from the group consisting of H, F, Cl, OH, and $OCH_3$; wherein $R^5$ and $R^7$ are individually selected from the group consisting of H, F, Cl, Br, $CH_3$, $C_2H_5$, OH, $OCH_3$, $OCH_2CH_3$, $OCH_2OCH_3$, $S(CH_3)_2^+$, and $N(alkyl)_3^+$; wherein $R^6$ is selected from the group consisting of H, F, Cl, Br, $CH_3$, $C_2H_5$, $NO_2$, OH, $OCH_3$, $OCH_2CH_3$, $OCH_2OCH_3$, $OCH_2CH_2OH$, $OCH_2CH_2OCH_3$, $OCH_2CH_2OCH_2CH_3$, polyglycol residue selected from the group consisting of methylene glycols, ethylene glycols, propylene glycols and mixtures thereof, and an aryl group; wherein Ar is selected from the group consisting of phenyl, napthyl, pyridyl, pyrrolidyl, furanyl, pyranyl, azepinyl, oxepinyl, imidizolyl, oxazolyl, pyrimidinyl, purinyl, and substituted groups thereof; wherein $R^9$ is selected from the group consisting of H, $CH_3$, $CH_2N(CH_3)_2$, and phenyl; wherein when either $R^5$ or $R^7$ is Cl and the other is H, $R^6$ is not Cl; wherein $R^{10}$ is selected from the group consisting of H, $CH_3$, $COCH_3$, and $C_5H_{10}N$; wherein $R^{11}$ is selected from the group consisting of phenyl, chlorophenyl, dichlorophenyl, dimethylaminophenyl, aminophenyl, piperonyl, dimethoxyphenyl, methoxyphenyl, acetamidophenyl, carbomoylphenyl, fluoromethoxyphenyl, napthyl, pyridyl, pyrrolidyl, furanyl, pyranyl, azepinyl, oxepinyl, imidizolyl, oxazolyl, pyrimidinyl, purinyl, and substituted groups thereof; wherein $R^{12}$ is selected from the group consisting of an aryl ester carboxylate, an alkyl ester carboxylate, an alkoxy ester carboxylate, an aryl carboxamide, an alkyl carboxamide, an alkoxy carboxamide, $C_2H_4NO$, and nitrile; wherein $R^{13}$ is selected from the group consisting of $NH_2$, $C_2H_3O$, $C_7H_4N_2O_3C_1$, $C_7H_4NOClF$, $C_6H_4N_2O_3Cl$, and $C_2H_4NO$; wherein when $R^{10}$ is $CH_3$, $R^{13}$ is not $C_2H_4NO$; wherein when $R^{12}$ is isopropyl carboxylate, $R^{11}$ is not 3,4-dichlorophenyl; and wherein the compound is not isopropyl 2-amino-4-(3,4-dichlorophenyl) thiophene-3-carboxylate.

The invention further includes a method of inhibiting or reducing vascular permeability. The method comprises administering to a subject a composition comprising a compound having a structure selected from the group consisting of structural formula (I) to (IX) in an amount effective to inhibit or reduce vascular permeability. The invention also provides a method of treating or preventing a disease or disorder characterized by abnormal vascular permeability in a subject. The method comprises administering a composition comprising a compound of any one of structural formulas (I) to (IX) to a subject in an amount effective to treat or prevent the disease or disorder. Optionally, the disease or disorder is a microvascular complication of a systemic condition in the subject, such as diabetes; a neoplastic disease or disorder; or a reperfusion injury, optionally preceded by an ischemic condition in which blood flow is severely reduced or blocked.

A method of inhibiting inflammation is also provided. The method comprises administering to a subject a composition comprising a compound of structural formula (I) to (IX) in an amount effective to inhibit inflammation. The invention further includes a method of inhibiting metabolic disorders. The method comprises administering to a subject a composition comprising a compound having a structure selected from the group consisting of structural formula (I) to (IX) in an amount effective to inhibit a metabolic disorder. A method of inhibiting angiogenesis in a subject is also provided. The method comprises administering to a subject a composition comprising a compound having a structure selected from the group consisting of structural formula (I) to (IX) in an amount effective to inhibit angiogenesis. The invention further includes a method of inhibiting cancer cell proliferation. The method comprises contacting a population of cancer cells with a compound having a structure selected from the group consisting of structural formula (I) to (IX) in an amount effective to inhibit cancer cell proliferation. In various embodiments, the method comprises administering a compound to a subject (e.g., a human) to inhibit cancer cell proliferation in vivo.

The use of a compound of any one of structural formulas (I) to (IX) in any of the methods disclosed herein or for preparation of medicaments for administration according to any of the methods disclosed herein is specifically contemplated. In this regard, the invention provides a compound of any one of structural formulas (I) to (IX) for use in a method of inhibiting an aPKC, wherein the method comprises contacting the aPKC with the compound. A compound of any one of structural formulas (I) to (IX)) for use in a method of treating or preventing a disease or disorder characterized by abnormal vascular permeability in a subject, a method of inhibiting or reducing vascular permeability, a method of inhibiting inflammation, a method of inhibiting metabolic disorders, a method of inhibiting angiogenesis, and a method of inhibiting cancer cell proliferation also are provided.

Further provided is a composition formulated for administration to a subject, the composition comprising a compound of any one of structural formulas (I) to (IX) and a pharmaceutically acceptable carrier.

Aspects of the invention are defined or summarized in the following numbered paragraphs:

1. A method of inhibiting or reducing vascular permeability, the method comprising administering to a subject a composition comprising an amount of a compound having a structure selected from the group consisting of structural formulas (I) to (VIII) effective to inhibit or reduce vascular permeability:

structural formula (I):

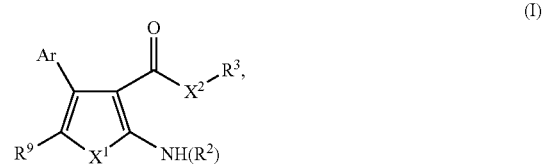

structural formula (II):

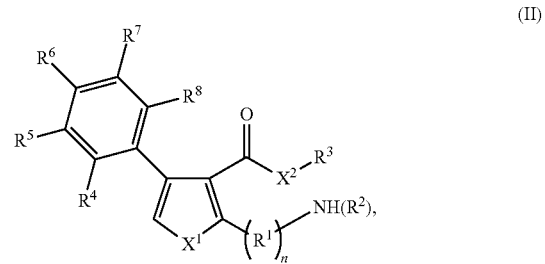

structural formula (III):

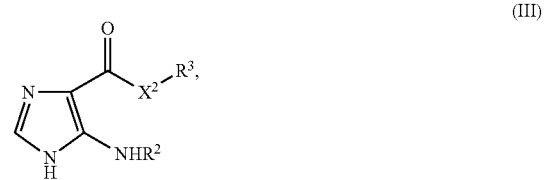

structural formula (IV):

structural formula (V):

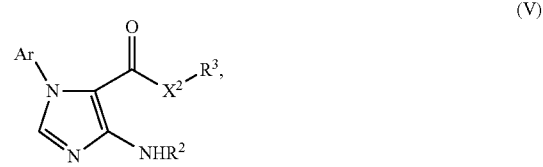

structural formula (VI):

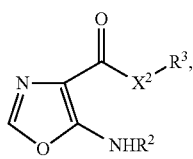

structural formula (VII):

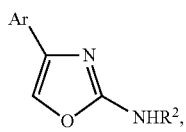

and structural formula (VIII):

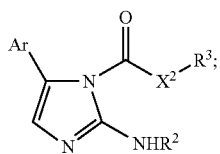

wherein $X^1$ is selected from the group consisting of O, S, NH, and NMe;
wherein n has a value of zero (0), one (1), or two (2);
wherein $R^1$ is selected from the group consisting of $CH_2$, $CH(CH_3)$, $C(CH_3)_2$, $C_2H_4$, and $C_2H_2$;
wherein $R^2$ is selected from the group consisting of H, $CH_3$, $CH_2OH$, $C_2H_5$, $C_2H_5O$, $CH(CH_3)_2$, $C(CH_3)$, $CH_2CH(CH_3)_2$, and $CH_2C(CH_3)_3$;
wherein $X^2$ is selected from the group consisting of O, S, NH and N; when $X^2$ is O, S, or NH, $R^3$ is selected from the group consisting of an aryl residue, an alkyl residue having 1 to 10 carbon atoms, an alkoxy residue having 1 to 10 carbon atoms, and a polyglycol residue having two to twelve carbon atoms; when $X^2$ is N, $R^3$ is either two independently selected residues each selected from the group consisting of an aryl residue, an alkyl residue having 1 to 10 carbon atoms, an alkoxy residue having 1 to 10 carbon atoms, and a polyglycol residue having two to twelve carbon atoms; or $X^2$ and $R^3$ are a cyclic group ($X^2$—$R^3$) having five or six members and optionally one or more additional heteroatoms;
wherein $R^4$ and $R^8$ are individually selected from the group consisting of H, F, Cl, OH, and $OCH_3$;
wherein $R^5$ and $R^7$ are individually selected from the group consisting of H, F, Cl, Br, $CH_3$, $C_2H_5$, OH, $OCH_3$, $OCH_2CH_3$, $OCH_2OCH_3$, $S(CH_3)_2^+$, and $N(alkyl)_3^+$;
wherein $R^6$ is selected from the group consisting of H; F; Cl; Br; $CH_3$; $C_2H_5$; $NO_2$; OH; $OCH_3$; $OCH_2CH_3$; $OCH_2OCH_3$; $OCH_2CH_2OH$; $OCH_2CH_2OCH_3$; $OCH_2CH_2OCH_2CH_3$; polyglycol residue selected from the group consisting of methylene glycols, ethylene glycols, propylene glycols and mixtures thereof; and an aryl group;

wherein Ar is selected from the group consisting of phenyl, napthyl, pyridyl, pyrrolidyl, furanyl, pyranyl, azepinyl, oxepinyl, imidizolyl, oxazolyl, pyrimidinyl, purinyl, and substituted groups thereof;
wherein $R^9$ is selected from the group consisting of H, $CH_3$, $CH_2N(CH_3)_2$, and phenyl;
wherein when either $R^5$ or $R^7$ is Cl and the other is H, $R^6$ is not Cl; and
wherein the compound is not isopropyl 2-amino-4-(3,4-dichlorophenyl)thiophene-3-carboxylate.

2. A method of inhibiting or reducing vascular permeability, the method comprising administering to a subject a composition comprising an amount of a compound having structural formula (IX) effective to inhibit or reduce vascular permeability:

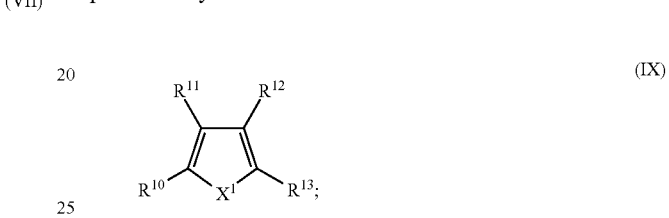

wherein $X^1$ is selected from the group consisting of O, S, NH, and NMe;
wherein $R^{10}$ is selected from the group consisting of H, $CH_3$, $COCH_3$, and $C_5H_{10}N$;
wherein $R^{11}$ is selected from the group consisting of phenyl, chlorophenyl, dichlorophenyl, dimethylaminophenyl, aminophenyl, piperonyl, dimethoxyphenyl, methoxyphenyl, acetamidophenyl, carbomoylphenyl, fluoromethoxyphenyl, napthyl, pyridyl, pyrrolidyl, furanyl, pyranyl, azepinyl, oxepinyl, imidizolyl, oxazolyl, pyrimidinyl, purinyl, and substituted groups thereof;
wherein $R^{12}$ is selected from the group consisting of an aryl ester carboxylate, an alkyl ester carboxylate, an alkoxy ester carboxylate, an aryl carboxamide, an alkyl carboxamide, an alkoxy carboxamide, $C_2H_4NO$, and nitrile;
wherein $R^{13}$ is selected from the group consisting of $NH_2$, $C_2H_3O$, $C_7H_4N_2O_3Cl$, $C_7H_4NOClF$, $C_6H_4N_2O_3Cl$, and $C_2H_4NO$;
wherein when $R^{10}$ is $CH_3$, $R^{13}$ is not $C_2H_4NO$; and
wherein when $R^{12}$ is isopropyl carboxylate, $R^{11}$ is not 3,4-dichlorophenyl.

3. A method of inhibiting aPKC comprising:
contacting an aPKC with a compound having a structure selected from the group consisting of
structural formula (I):

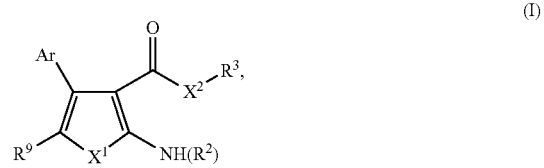

structural formula (II):

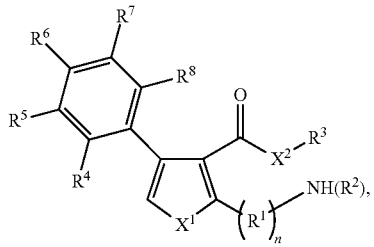

structural formula (III):

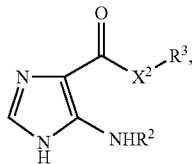

structural formula (IV):

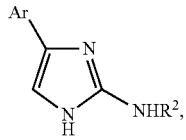

structural formula (V):

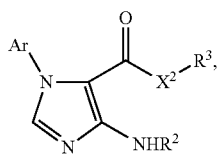

structural formula (VI):

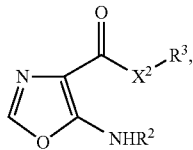

structural formula (VII):

and structural formula (VIII):

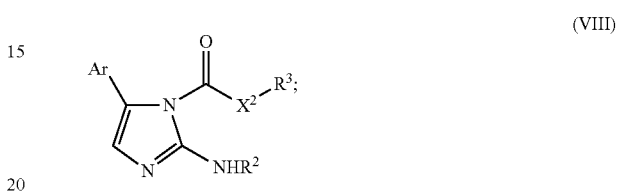

wherein $X^1$ is selected from the group consisting of O, S, NH, and NMe;

wherein n has a value of zero (0), one (1), or two (2);

wherein $R^1$ is selected from the group consisting of $CH_2$, $CH(CH_3)$, $C(CH_3)_2$, $C_2H_4$, and $C_2H_2$;

wherein $R^2$ is selected from the group consisting of H, $CH_3$, $CH_2OH$, $C_2H_5$, $C_2H_5O$, $CH(CH_3)_2$, $C(CH_3)$, $CH_2CH(CH_3)_2$, and $CH_2C(CH_3)_3$;

wherein $X^2$ is selected from the group consisting of O, S, NH and N; when $X^2$ is O, S, or NH, $R^3$ is selected from the group consisting of an aryl residue, an alkyl residue having 1 to 10 carbon atoms, an alkoxy residue having 1 to 10 carbon atoms, and a polyglycol residue having two to twelve carbon atoms; when $X^2$ is N, $R^3$ is either two independently selected residues each selected from the group consisting of an aryl residue, an alkyl residue having 1 to 10 carbon atoms, an alkoxy residue having 1 to 10 carbon atoms, and a polyglycol residue having two to twelve carbon atoms; or $X^2$ and $R^3$ are a cyclic group ($X^2$—$R^3$) having five or six members and optionally one or more additional heteroatoms;

wherein $R^4$ and $R^8$ are individually selected from the group consisting of H, F, Cl, OH, and $OCH_3$;

wherein $R^5$ and $R^7$ are individually selected from the group consisting of H, F, Cl, Br, $CH_3$, $C_2H_5$, OH, $OCH_3$, $OCH_2CH_3$, $OCH_2OCH_3$, $S(CH_3)_2^+$, and $N(alkyl)_3^+$;

wherein $R^6$ is selected from the group consisting of H; F; Cl; Br; $CH_3$; $C_2H_5$; $NO_2$; OH; $OCH_3$; $OCH_2CH_3$; $OCH_2OCH_3$; $OCH_2CH_2OH$; $OCH_2CH_2OCH_3$; $OCH_2CH_2OCH_2CH_3$; polyglycol residue selected from the group consisting of methylene glycols, ethylene glycols, propylene glycols and mixtures thereof; and an aryl group;

wherein Ar is selected from the group consisting of phenyl, napthyl, pyridyl, pyrrolidyl, furanyl, pyranyl, azepinyl, oxepinyl, imidizolyl, oxazolyl, pyrimidinyl, purinyl, and substituted groups thereof;

wherein $R^9$ is selected from the group consisting of H, $CH_3$, $CH_2N(CH_3)_2$, and phenyl;

wherein when either $R^5$ or $R^7$ is Cl and the other is H, $R^6$ is not Cl; and wherein the compound is not isopropyl 2-amino-4-(3,4-dichlorophenyl)thiophene-3-carboxylate.

4. A method of inhibiting aPKC comprising:

contacting an aPKC with a compound having structural formula (IX):

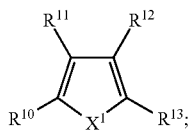

wherein $X^1$ is selected from the group consisting of O, S, NH, and NMe;

wherein $R^{10}$ is selected from the group consisting of H, $CH_3$, $COCH_3$, and $C_5H_{10}N$;

wherein $R^{11}$ is selected from the group consisting of phenyl, chlorophenyl, dichlorophenyl, dimethylaminophenyl, aminophenyl, piperonyl, dimethoxyphenyl, methoxyphenyl, acetamidophenyl, carbomoylphenyl, fluoromethoxyphenyl, napthyl, pyridyl, pyrrolidyl, furanyl, pyranyl, azepinyl, oxepinyl, imidizolyl, oxazolyl, pyrimidinyl, purinyl, and substituted groups thereof;

wherein $R^{12}$ is selected from the group consisting of an aryl ester carboxylate, an alkyl ester carboxylate, an alkoxy ester carboxylate, an aryl carboxamide, an alkyl carboxamide, an alkoxy carboxamide, $C_2H_4NO$, and nitrile;

wherein $R^{13}$ is selected from the group consisting of $NH_2$, $C_2H_3O$, $C_7H_4N_2O_3Cl$, $C_7H_4NOClF$, $C_6H_4N_2O_3Cl$, and $C_2H_4NO$;

wherein when $R^{10}$ is $CH_3$, $R^{13}$ is not $C_2H_4NO$; and wherein when $R^{12}$ is isopropyl carboxylate, $R^{11}$ is not 3,4-dichlorophenyl.

5. The method of any one of paragraphs 1-4, wherein the method comprises administering to a subject a composition comprising the compound in an amount effective to inhibit vascular permeability, inflammation, metabolic disorders, cancer cell proliferation, or angiogenesis.

6. The method of any one of paragraphs 3-5, wherein the method comprises administering to a subject a composition comprising the compound in an amount effective to inhibit or reduce vascular permeability.

7. The method of paragraphs 1-6, wherein the vascular permeability is associated with a disease or disorder characterized by abnormal vascular permeability.

8. The method of paragraph 7, wherein the disease or disorder is macular edema, diabetic retinopathy, retinopathy of prematurity, age-related macular degeneration, uveitis, branch retinal vein occlusion, central retinal vein occlusion, ischemia-reperfusion injury, neoplasic disease, or brain edema.

9. The method of any one of paragraphs 1-5, wherein the method comprises administering to a subject a composition comprising the compound in an amount effective to inhibit inflammation.

10. The method of any one of paragraphs 1-5, wherein the method comprises administering to a subject a composition comprising the compound in an amount effective to inhibit a metabolic disorder selected from the group consisting of diabetes, insulin resistance, obesity, impaired insulin signaling, hyperglycemia, hyperinsulinemia, hepatosteatosis, hypertriglyceridemia, hypercholesterolemia and metabolic syndrome.

11. The method of any one of paragraphs 1-5, wherein the method comprises contacting a population of cancer cells with the compound in an amount effective to inhibit cancer cell proliferation.

12. The method of any one of paragraphs 1-5, wherein the method comprises administering to a subject a composition comprising the compound in an amount effective to inhibit angiogenesis.

13. The method of any one of paragraphs 1, 3, and 5-12, wherein $X^1$ is S; $X^2$ is O; n has a value of zero (0); and $R^2$ is H.

14. The method of any one of paragraphs 1, 3, and 5-13, wherein $R^3$ is an aryl residue or an alkyl residue having 1 to 10 carbons; and $R^4$ and $R^8$ are H.

15. The method of any one of paragraphs 1, 3, and 5-14, wherein $R^7$ is H; and $R^5$ is selected from the group consisting of H, F, Cl, Br, $CH_3$, $C_2H_5$, OH, $OCH_3$, $OCH_2CH_3$, $OCH_2OCH_3$, $S(CH_3)^+$, and $N(alkyl)_3^+$.

16. The method of any one of paragraphs 1, 3, and 5-15, wherein $R^6$ is selected from the group consisting of H, F, Cl, Br, $CH_3$, $C_2H_5$, $NO_2$, OH, $OCH_3$, $OCH_2CH_3$, $OCH_2CH_2OH$, $OCH_2CH_2OCH_3$, and $OCH_2CH_2OCH_2CH_3$.

17. The method of any one of paragraphs 1, 3, and 5-16, wherein $R^5$ is selected from the group consisting of H, $OCH_3$, and $OCH_2CH_3$; $R^6$ is selected from the group consisting of OH, $OCH_3$, $OCH_2CH_3$, $OCH_2CH_2OH$, $OCH_2CH_2OCH_3$, and $OCH_2CH_2OCH_2CH_3$; and $R^7$ is H.

18. The method of any one of paragraphs 1, 3, and 5-17, wherein $R^5$ is $OCH_3$; $R^6$ is $OCH_3$; and $R^7$ is H.

19. The method of any one of paragraphs 1, 3, and 5-18, wherein $R^9$ is selected from the group consisting of H, $CH_3$, and $CH_2N(CH_3)_2$.

20. The method of any one of paragraphs 1, 3, and 5-19, wherein Ar is selected from the group consisting of phenyl, dimethoxyphenyl, chlorophenyl, dichlorophenyl, bromophenyl, hydroxyphenyl, trimethylphenyl, fluorophenyl, nitrophenyl, methoxyphenyl, dihydrobenzopyran, or pyridine.

21. The method of any one of paragraphs 1, 3, and 5-19, wherein Ar is selected from the group consisting of dimethyl aminophenyl, aminophenyl, piperonyl, fluoromethoxyphenyl, acetamidophenyl, and carbomoylphenyl.

22. The method of paragraph 20, wherein $R^3$ is $CH(CH_3)_2$, $R^9$ is H, and Ar is a dimethoxyphenyl group.

23. The method of paragraph 21, wherein $R^3$ is $CH_2CH_3$, $R^9$ is H, and Ar is a piperonyl group.

24. The method of any one of paragraphs 1-12, wherein the compound has a structural formula selected from the group consisting of:

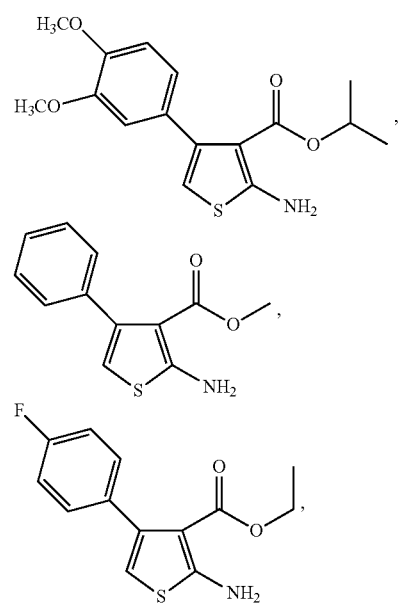

-continued
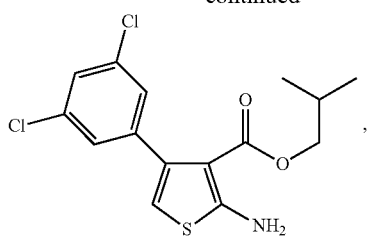
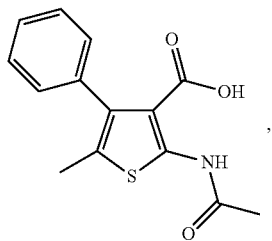
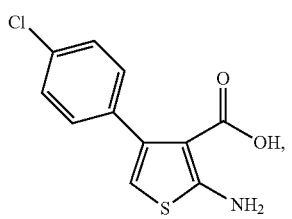
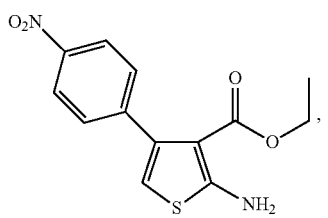
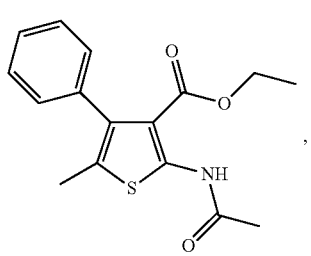
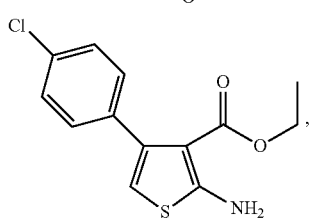
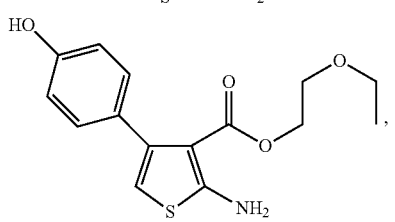
-continued
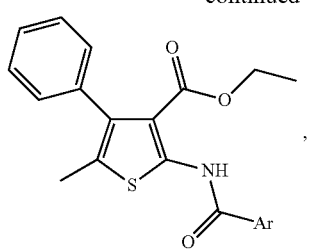
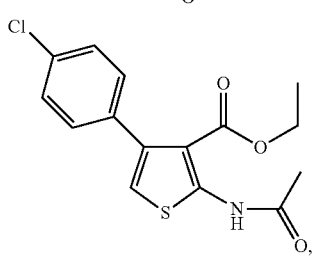
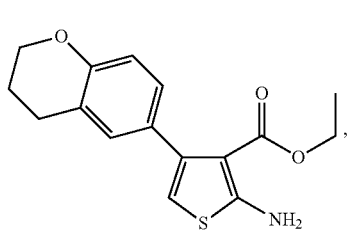
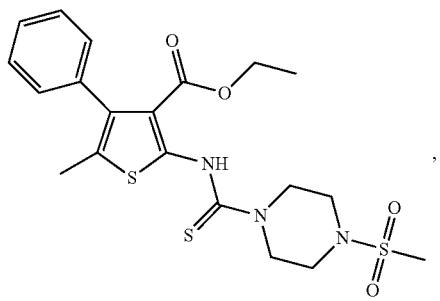
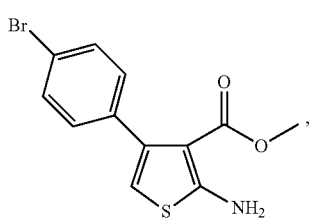
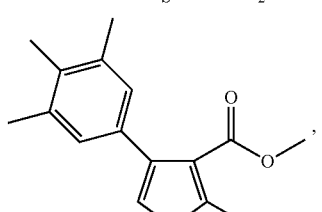
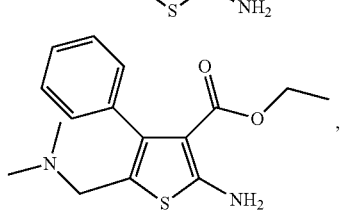

-continued
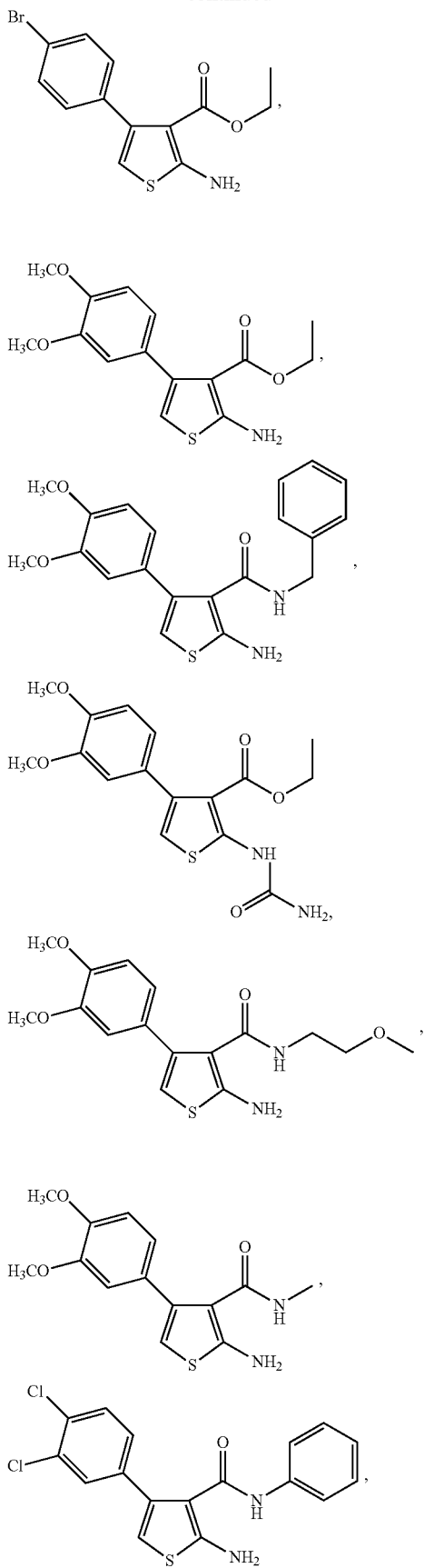
-continued
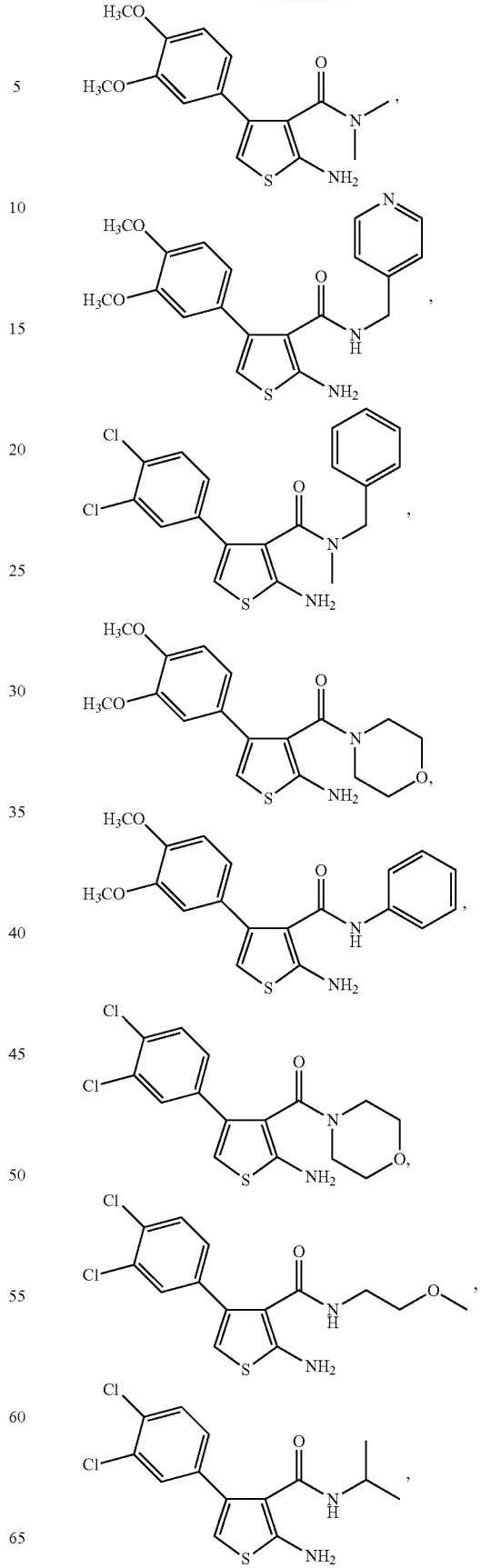

-continued
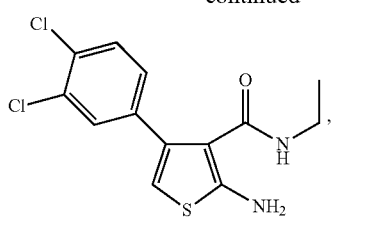
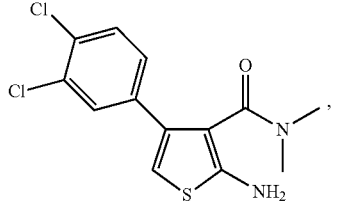
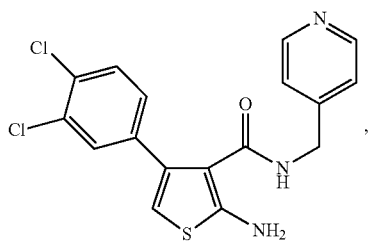
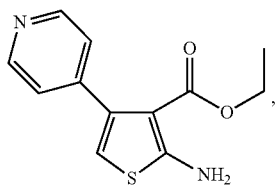
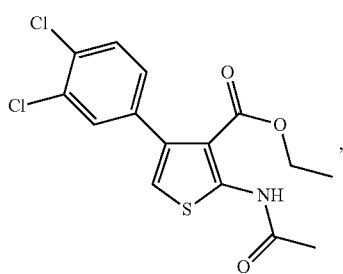
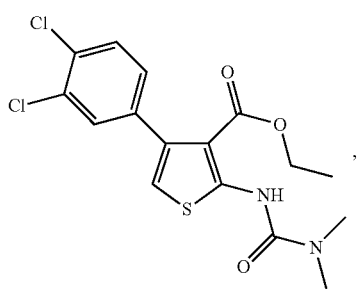
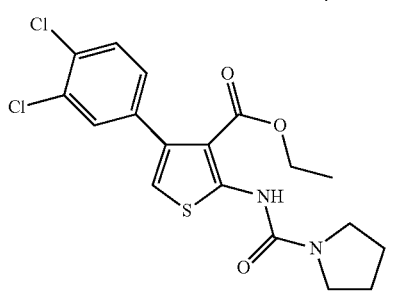
and
-continued
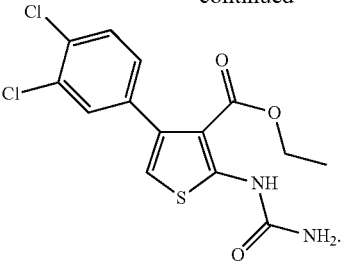
25. The method of any one of paragraphs 1-12, wherein the compound has a structural formula selected from the group consisting of:
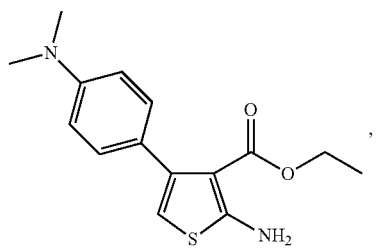
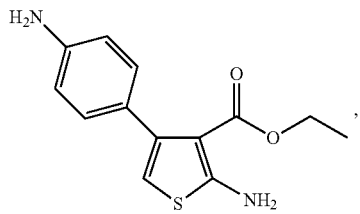
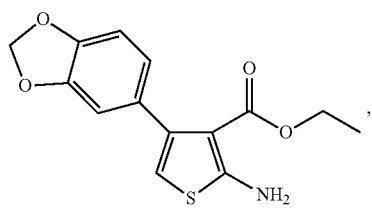
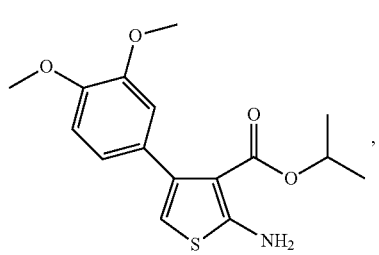
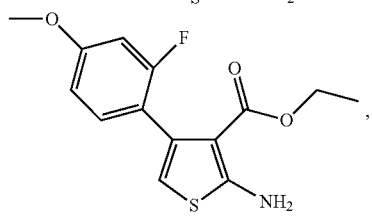

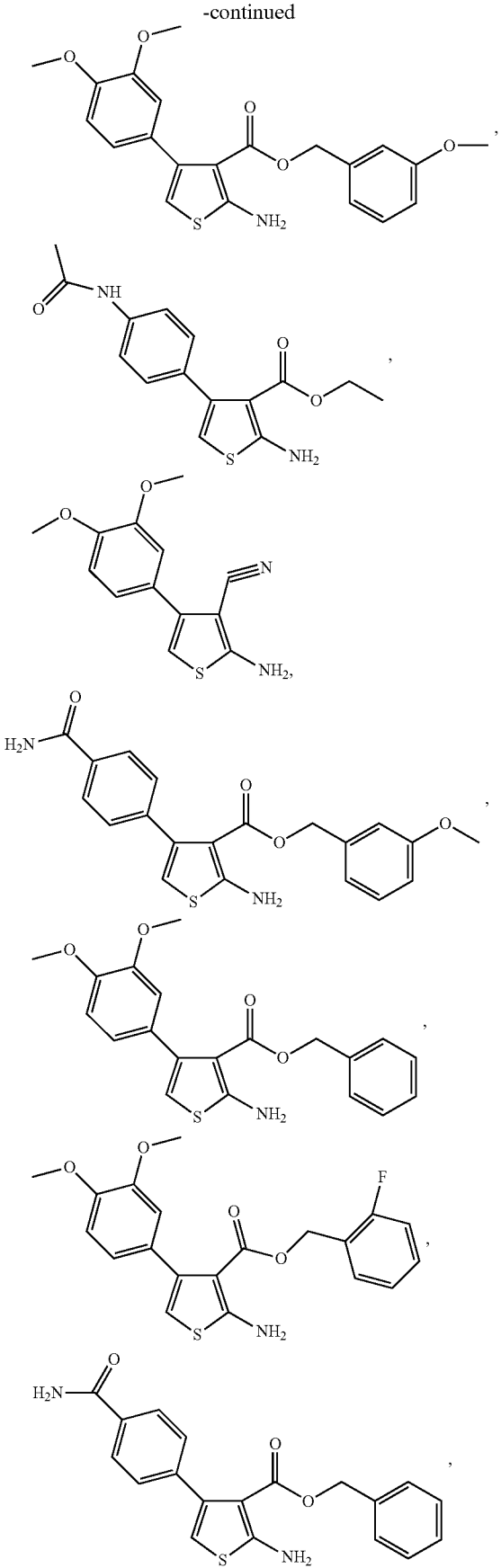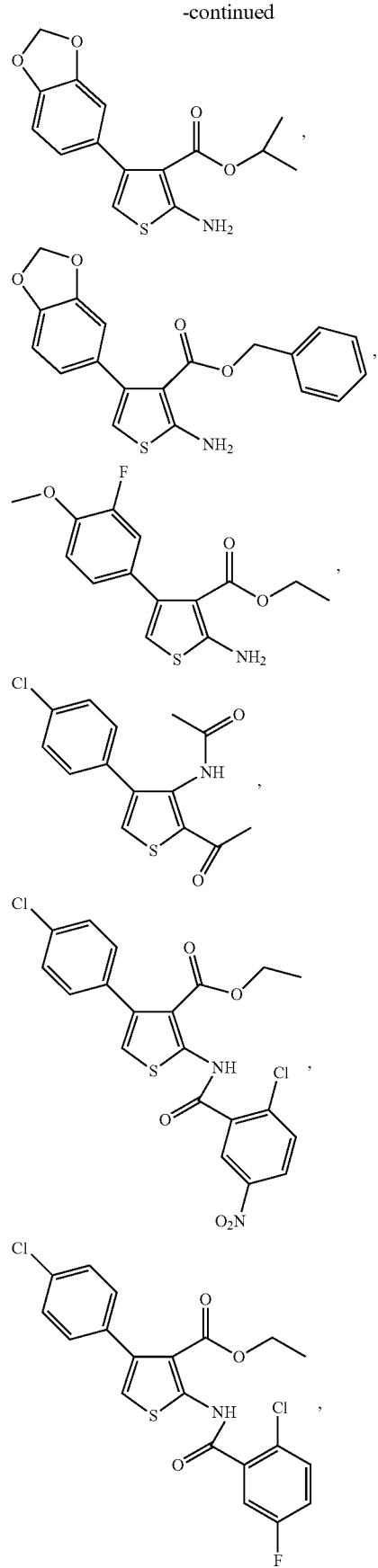

-continued
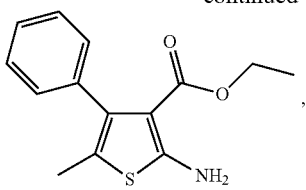,
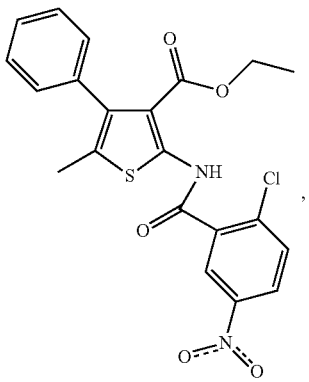,
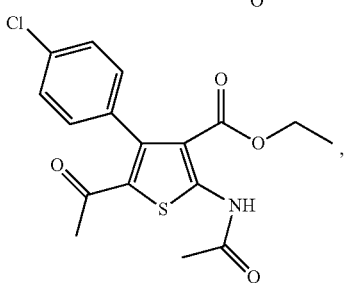,
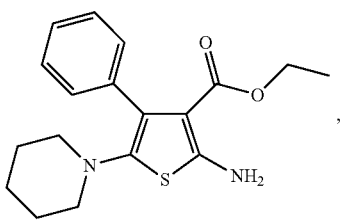,
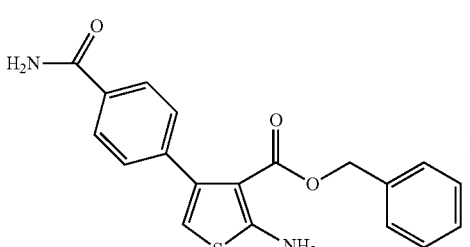,
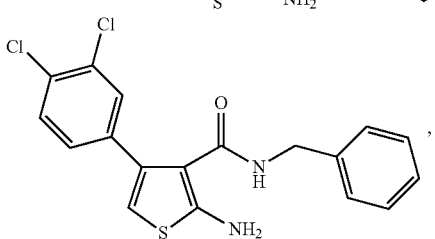,
-continued
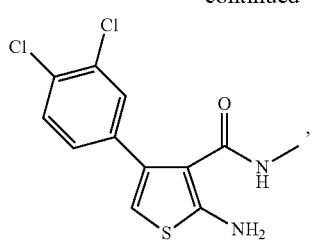,
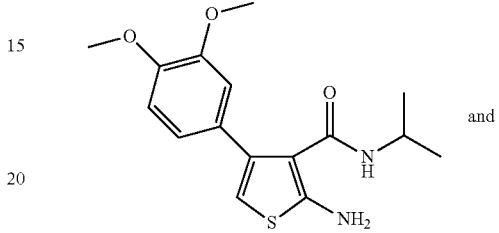 and
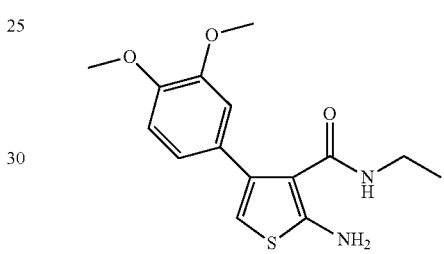.
26. A formulation for oral, subcutaneous, topical, or intraocular administration comprising:
   a pharmaceutically acceptable excipient; and
   a compound having a structure selected from the group consisting of structural formulas (I) to (VIII):
   structural formula (I):
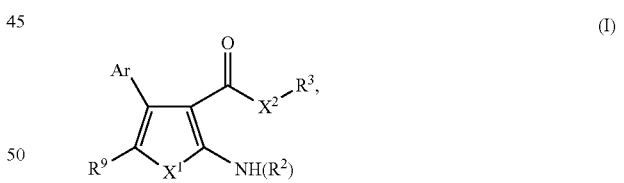
structural formula (II):
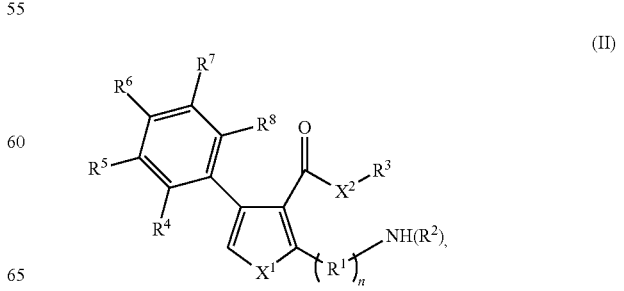

structural formula (III):

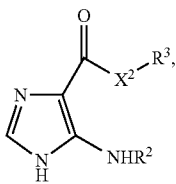

structural formula (IV):

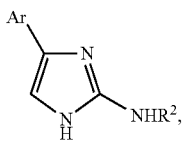

structural formula (V):

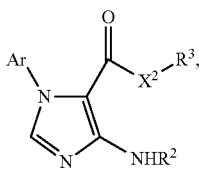

structural formula (VI):

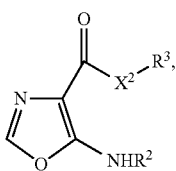

structural formula (VII):

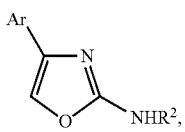

and structural formula (VIII):

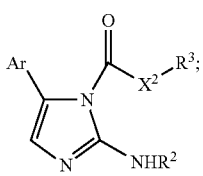

wherein $X^1$ is selected from the group consisting of O, S, NH, and NMe;

wherein n has a value of zero (0), one (1), or two (2);

wherein $R^1$ is selected from the group consisting of $CH_2$, $CH(CH_3)$, $C(CH_3)_2$, $C_2H_4$, and $C_2H_2$;

wherein $R^2$ is selected from the group consisting of H, $CH_3$, $CH_2OH$, $C_2H_5$, $C_2H_5O$, $CH(CH_3)_2$, $C(CH_3)$, $CH_2CH(CH_3)_2$, and $CH_2C(CH_3)_3$;

wherein $X^2$ is selected from the group consisting of O, S, NH and N; when $X^2$ is O, S, or NH, $R^3$ is selected from the group consisting of an aryl residue, an alkyl residue having 1 to 10 carbon atoms, an alkoxy residue having 1 to 10 carbon atoms, and a polyglycol residue having two to twelve carbon atoms; when $X^2$ is N, $R^3$ is either two independently selected residues each selected from the group consisting of an aryl residue, an alkyl residue having 1 to 10 carbon atoms, an alkoxy residue having 1 to 10 carbon atoms, and a polyglycol residue having two to twelve carbon atoms; or $X^2$ and $R^3$ are a cyclic group ($X^2$—$R^3$) having five or six members and optionally one or more additional heteroatoms;

wherein $R^4$ and $R^8$ are individually selected from the group consisting of H, F, Cl, OH, and $OCH_3$;

wherein $R^5$ and $R^7$ are individually selected from the group consisting of H, F, Cl, Br, $CH_3$, $O_2H_5$, OH, $OCH_3$, $OCH_2CH_3$, $OCH_2OCH_3$, $S(CH_3)_2^+$, and $N(alkyl)_3^+$;

wherein $R^6$ is selected from the group consisting of H; F; Cl; Br; $CH_3$; $O_2H_5$; $NO_2$; OH; $OCH_3$; $OCH_2CH_3$; $OCH_2OCH_3$; $OCH_2CH_2OH$; $OCH_2CH_2OCH_3$; $OCH_2CH_2OCH_2CH_3$; polyglycol residue selected from the group consisting of methylene glycols, ethylene glycols, propylene glycols and mixtures thereof; and an aryl group;

wherein Ar is selected from the group consisting of phenyl, napthyl, pyridyl, pyrrolidyl, furanyl, pyranyl, azepinyl, oxepinyl, imidizolyl, oxazolyl, pyrimidinyl, purinyl, and substituted groups thereof;

wherein $R^9$ is selected from the group consisting of H, $CH_3$, $CH_2N(CH_3)_2$, and phenyl;

wherein when either $R^5$ or $R^7$ is Cl and the other is H, $R^6$ is not Cl; and wherein the compound is not isopropyl 2-amino-4-(3,4-dichlorophenyl)thiophene-3-carboxylate.

27. A formulation for oral, subcutaneous, topical, or intraocular administration comprising:

a pharmaceutically acceptable excipient; and a compound having structural formula (IX):

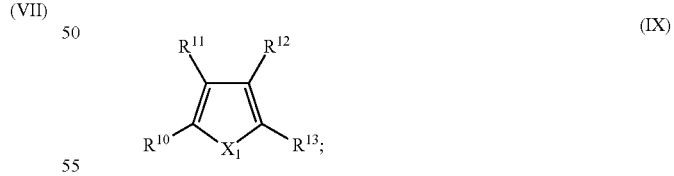

wherein $X^1$ is selected from the group consisting of O, S, NH, and NMe;

wherein $R^{10}$ is selected from the group consisting of H, $CH_3$, $COCH_3$, and $C_5H_{10}N$;

wherein $R^{11}$ is selected from the group consisting of phenyl, chlorophenyl, dichlorophenyl dimethylaminophenyl, aminophenyl, piperonyl, dimethoxyphenyl, methoxyphenyl, acetamidophenyl, carbomoylphenyl, fluoromethoxyphenyl, napthyl, pyridyl, pyrrolidyl, furanyl, pyranyl, azepinyl, oxepinyl, imidizolyl, oxazolyl, pyrimidinyl, purinyl, and substituted groups thereof;

wherein $R^{12}$ is selected from the group consisting of an aryl ester carboxylate, an alkyl ester carboxylate, an alkoxy ester carboxylate, an aryl carboxamide, an alkyl carboxamide, an alkoxy carboxamide, $C_2H_4NO$, and nitrile;

wherein $R^{13}$ is selected from the group consisting of $NH_2$, $C_2H_3O$, $C_7H_4N_2O_3Cl$, $C_7H_4NOClF$, $C_6H_4N_2O_3Cl$, and $C_2H_4NO$;

wherein when $R^{10}$ is $CH_3$, $R^{13}$ is not $C_2H_4NO$; and wherein when $R^{12}$ is isopropyl carboxylate, $R^{11}$ is not 3,4-dichlorophenyl.

28. The formulation of paragraph 26, wherein $X^1$ is S; $X^2$ is O; n has a value of zero (0); and $R^2$ is H.

29. The formulation of paragraph 26 or 28, wherein $R^3$ is an aryl residue or an alkyl residue having 1 to 10 carbons; and $R^4$ and $R^8$ are H.

30. The formulation of any one of paragraphs 26, 28, and 29, wherein $R^7$ is H; and $R^5$ is selected from the group consisting of H, F, Cl, Br, $CH_3$, $C_2H_5$, OH, $OCH_3$, $OCH_2CH_3$, $OCH_2OCH_3$, $S(CH_3)^+$, and $N(alkyl)_3^+$.

31. The formulation of any one of paragraphs 26 and 28-30, wherein $R^6$ is selected from the group consisting of H, F, Cl, Br, $CH_3$, $C_2H_5$, $NO_2$, OH, $OCH_3$, $OCH_2CH_3$, $OCH_2CH_2OH$, $OCH_2CH_2OCH_3$, and $OCH_2CH_2OCH_2CH_3$.

32. The formulation of any one of paragraphs 26 and 28-31, wherein $R^5$ is selected from the group consisting of H and $OCH_3$, and $OCH_2CH_3$; $R^6$ is selected from the group consisting of OH, $OCH_3$, $OCH_2CH_3$, $OCH_2CH_2OH$, $OCH_2CH_2OCH_3$, and $OCH_2CH_2OCH_2CH_3$; and $R^7$ is H.

33. The formulation of any one of paragraphs 26 and 28-32, wherein $R^5$ is selected from the group consisting of H and $OCH_3$, and $OCH_2CH_3$; $R^6$ is selected from the group consisting of $OCH_3$, $OCH_2CH_3$, $OCH_2CH_2OCH_3$, and $OCH_2CH_2OCH_2CH_3$; and $R^7$ is H.

34. The formulation of any one of paragraphs 26 and 28-33, wherein $R^5$ is $OCH_3$; $R^6$ is $OCH_3$; and $R^7$ is H.

35. The formulation of any one of paragraphs 26 and 28-34, wherein $R^9$ is selected from the group consisting of H, $CH_3$, and $CH_2N(CH_3)_2$.

36. The formulation of any one of paragraphs 26 and 28-35, wherein Ar is selected from the group consisting of phenyl, dimethoxyphenyl, chlorophenyl, bromophenyl, hydroxyphenyl, trimethylphenyl, fluorophenyl, nitrophenyl, methoxyphenyl, dihydrobenzopyran, or pyridine.

37. The formulation of any one of paragraphs 26 and 28-35, wherein Ar is selected from the group consisting of dimethyl aminophenyl, aminophenyl, piperonyl, fluoromethoxyphenyl, acetamidophenyl, and carbomoylphenyl.

38. The formulation of paragraph 36, wherein $R^3$ is $CH(CH_3)_2$, $R^9$ is H, and Ar is a dimethoxyphenyl group.

39. The formulation of paragraph 37, wherein $R^3$ is $CH_2CH_3$, $R^9$ is H, and Ar is a piperonyl group.

40. The formulation of paragraph 26, wherein the compound has a structural formula selected from the group consisting of:

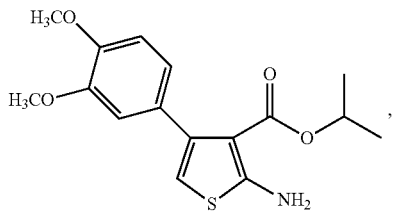

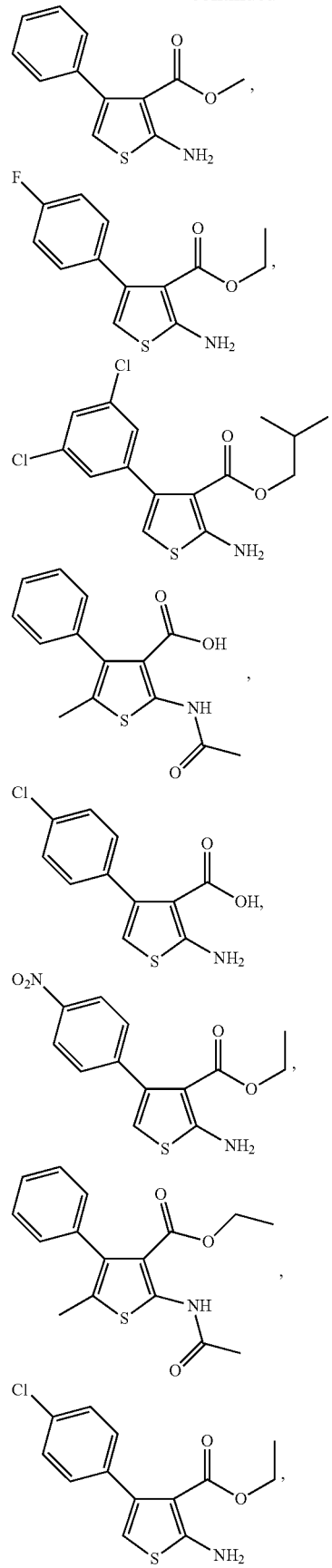

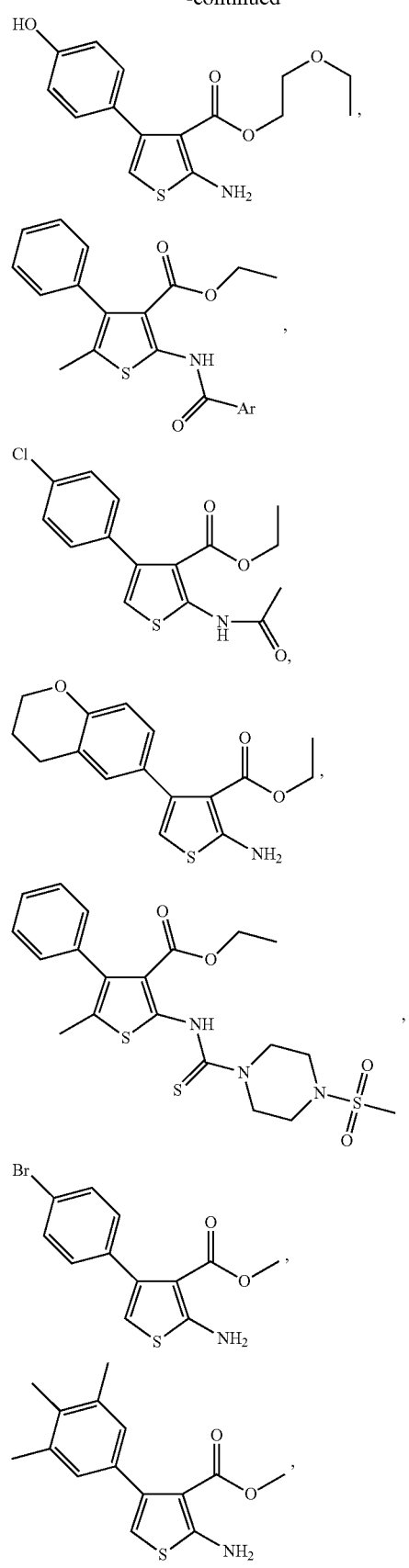
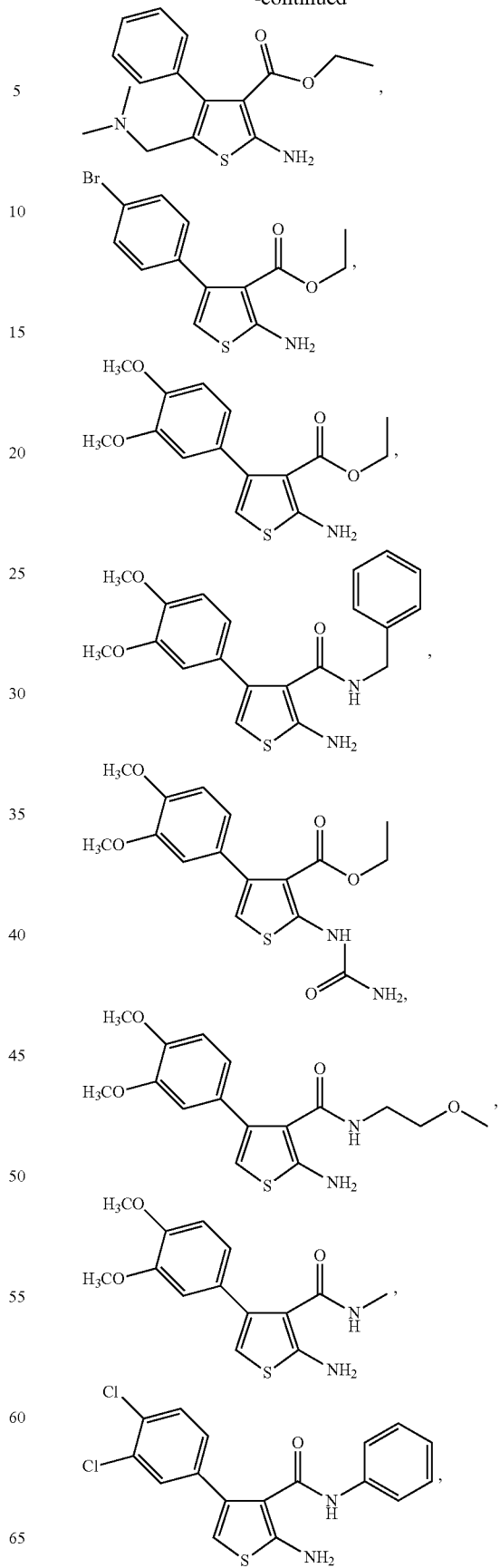

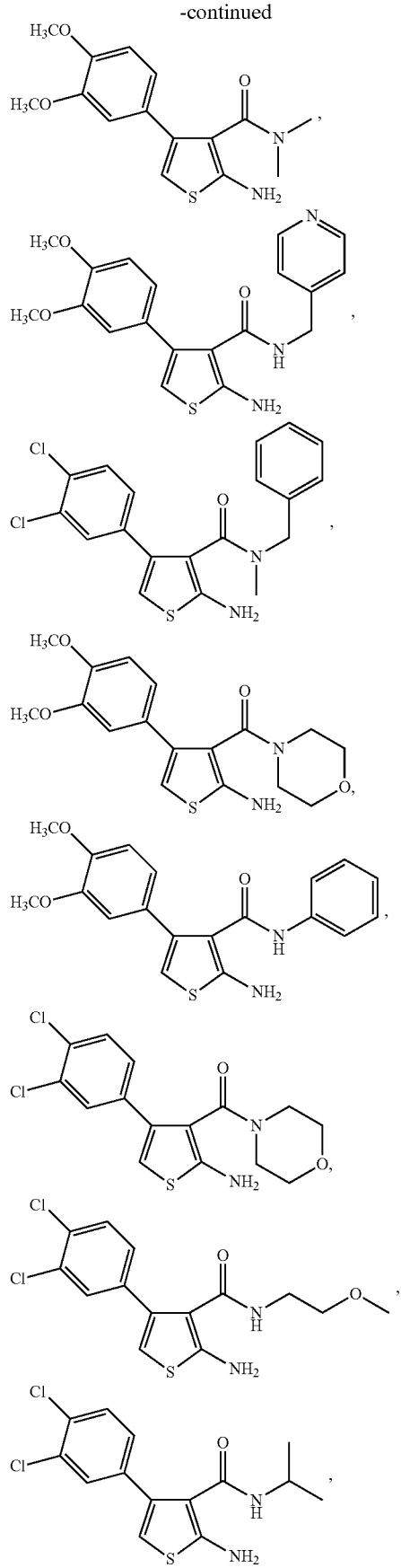

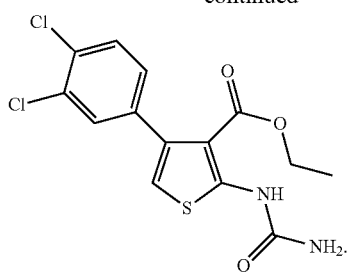
41. The formulation of paragraph 27, wherein the compound has a structural formula selected from the group consisting of:
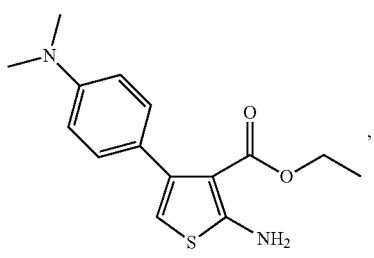
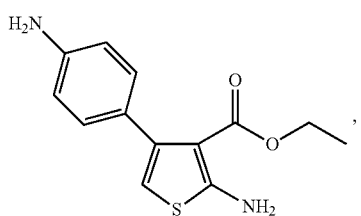
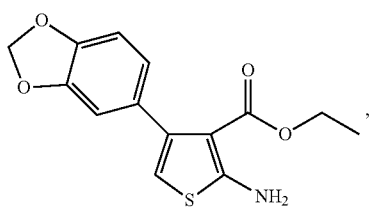
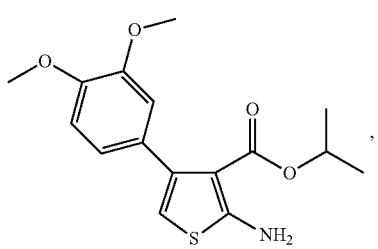
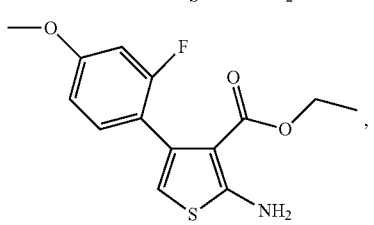
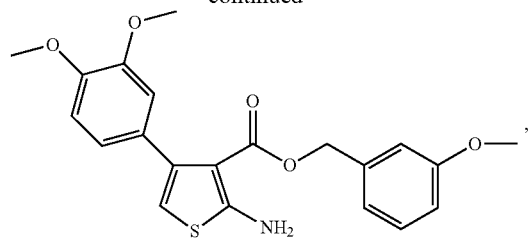
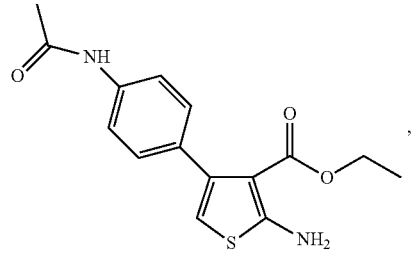
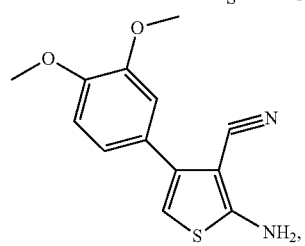
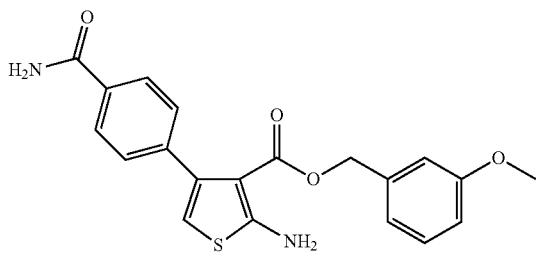
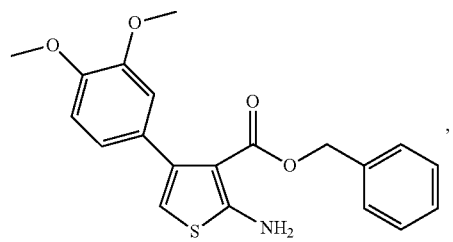
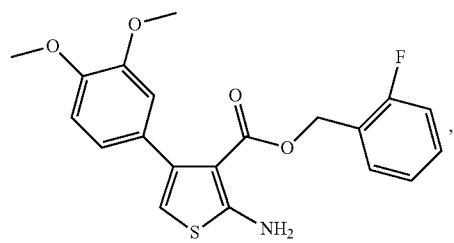
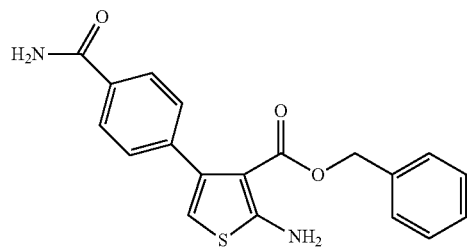

33
-continued
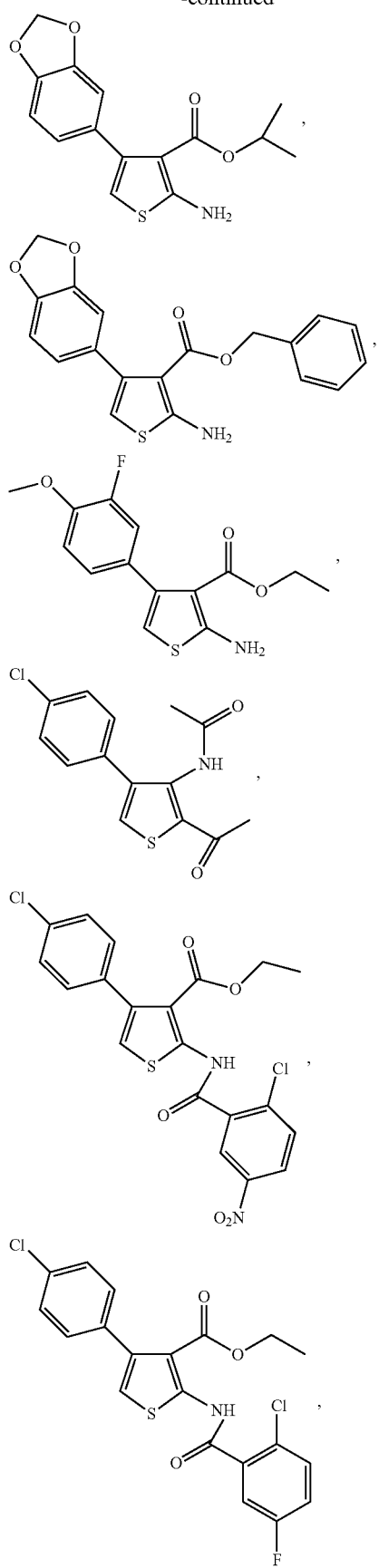
34
-continued
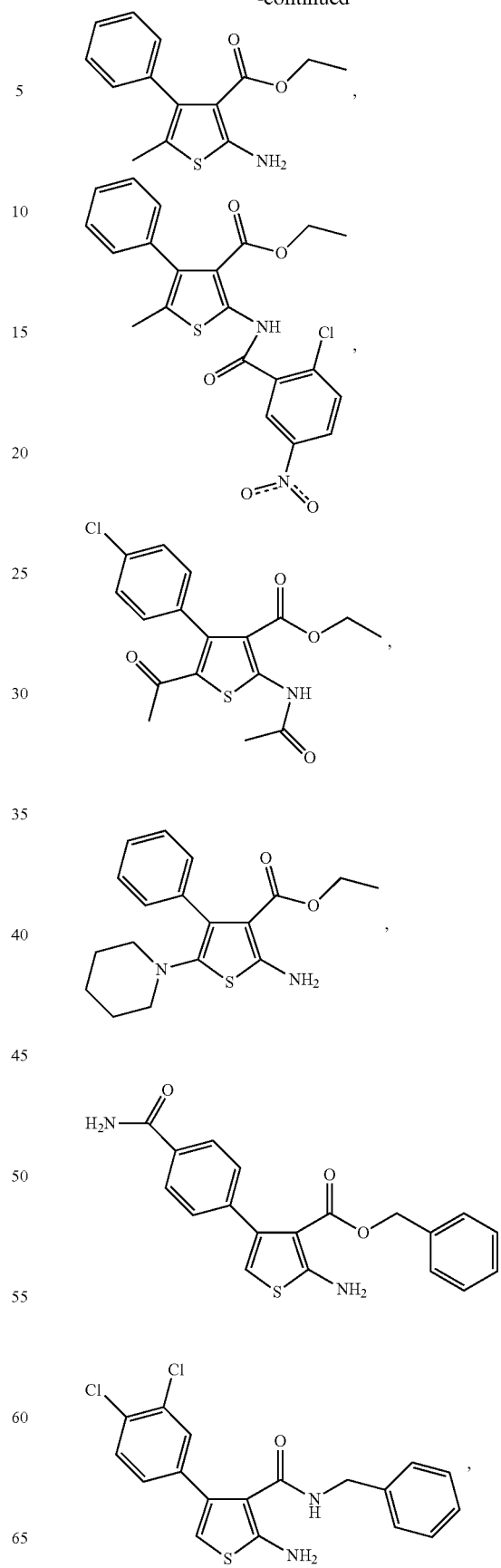

-continued

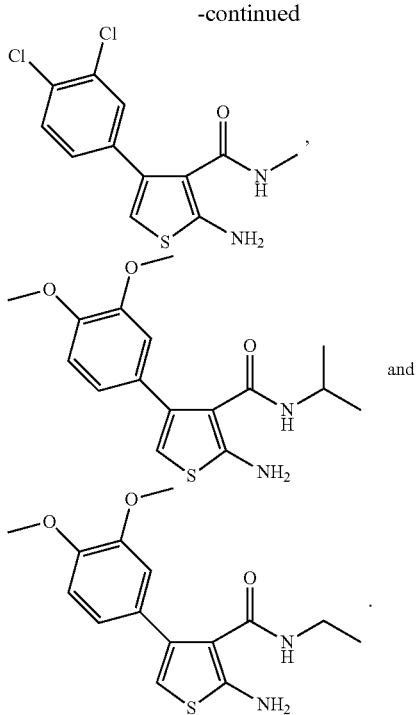

and

BRIEF DESCRIPTION OF THE FIGURES

In FIG. 2A, compound designations are provided on the X-axis, and velocity (RFU/minute) is provided on the Y-axis. In FIG. 2B, compound designations are provided on the X-axis, and % kinase activity is provided on the Y-axis. The control reaction comprising vehicle was designated as 100% kinase activity.

In FIG. 4A, compound designations are provided on the X-axis, and velocity (RFU/minute) is provided on the Y-axis. In FIG. 4B, compound designations are provided on the X-axis, and enzyme velocity relative to vehicle (% of vehicle) is provided on the Y-axis. The control reaction comprising vehicle was designated as 100% kinase activity.

In FIG. 5A, compound amount is provided on the X-axis, and relative enzyme velocity (% of vehicle) is provided on the Y-axis. In FIG. 5B, compound amount is provided on the X-axis, and relative enzyme velocity (% of vehicle) is depicted on the Y-axis.

In FIG. 8A, ATP competition was assayed using excess CREBtide substrate. In FIG. 8B, ATP competition was assayed using excess ATP.

DETAILED DESCRIPTION OF THE INVENTION

Figure 1:
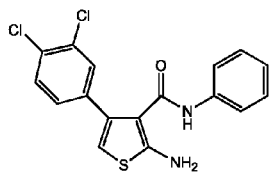
FIG. 1 depicts chemical structures of compounds assayed for aPKC inhibitory activity.
Figure 1:
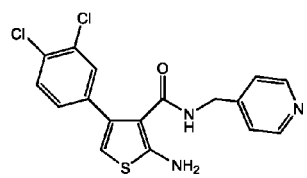
Figure 1:
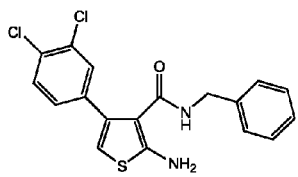
Figure 1:
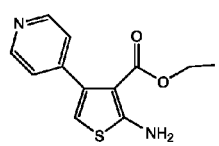
Figure 1:
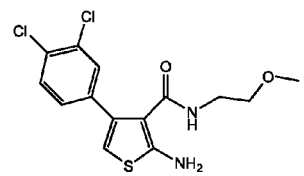
Figure 1:
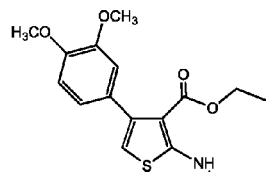
Figure 1:
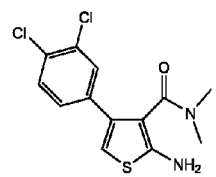
Figure 1:
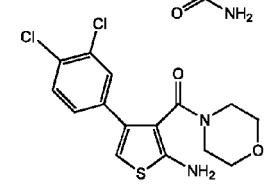
Figure 1:
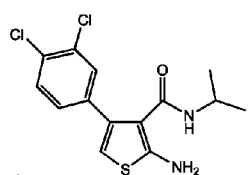
Figure 1:
Figure 1:
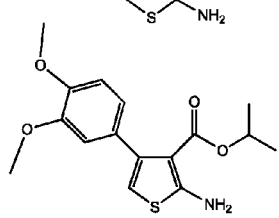
Figure 1:
Figure 1:
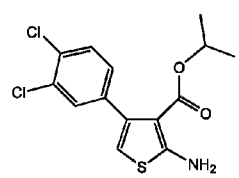
Figure 2A:
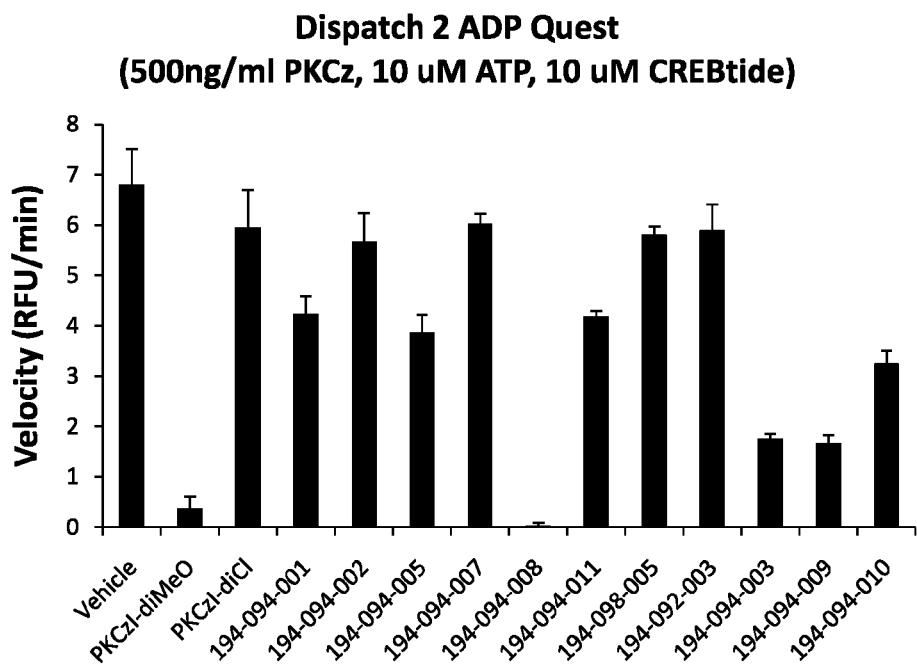
FIGS. 2A and 2B are bar graphs illustrating ADP Quest™ test results for the compounds of FIG. 1.
Figure 2B:
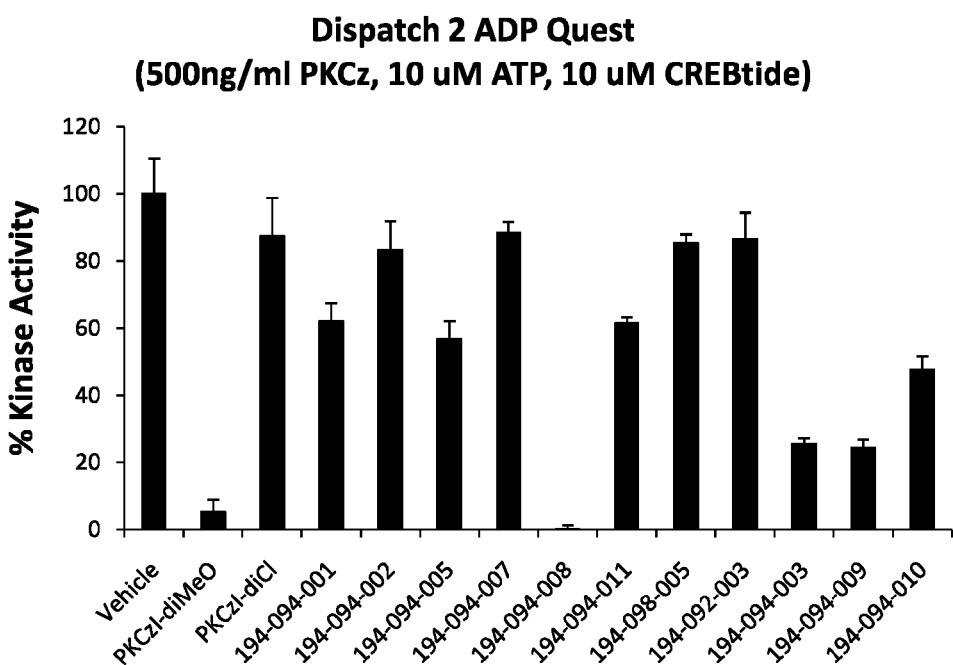

The invention provides compounds, methods, and compositions for inhibiting or reducing vascular permeability. The invention further provides compounds, methods, and compositions for inhibiting atypical protein kinase C (aPKC). Atypical PKC is a subfamily of kinases and includes at least isoforms aPKC-lambda (aPKCλ), aPKC-iota (aPKCι), and aPKC-zeta (aPKCζ). Atypical PKCζ and aPKCι have been cloned, and the nucleic acid and amino acid sequences are known. For example, the sequence of human aPKC-zeta is described in, e.g., Kochs et al., *Eur. J. Biochem.*, 216(2):597-606 (1993). The aPKC isoforms are structurally related; the amino acid sequences of aPKCζ and aPKCλ, have 72% overall amino acid identity. See, e.g., Moscat et al., *EMBO Rep.*, 1(5):399-403 (2000).

In one aspect, the invention provides a method of inhibiting or reducing vascular permeability. The method comprises, in various embodiments, administering to a subject a composition comprising an amount of a compound of structural formula (I):

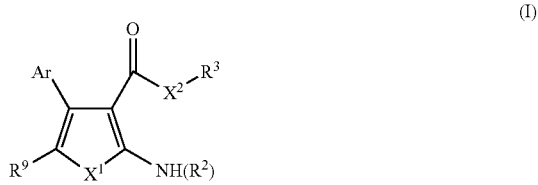

(I)

In structural formula (I), $X^1$ is selected from the group consisting of O, S, NH, and NMe. Preferably, $X^1$ is O, $X^1$ is S, or $X^1$ is NH.

In structural formula (I), $R^2$ is selected from the group consisting of H, $CH_3$, $CH_2OH$, $C_2H_5$, $C_2H_5O$, $CH(CH_3)_2$, $C(CH_3)_3$, $CH_2CH(CH_3)_2$, and $CH_2C(CH_3)_3$. Preferably, $R^2$ is selected from the group consisting of H, $CH_3$, $CH_2OH$, and $C_2H_5$, more preferably $R^2$ is H.

In structural formula (I), $X^2$ is selected from the group consisting of O, S, NH and N; preferably $X^2$ is O. When $X^2$ is O, S or NH; $R^3$ is selected from the group consisting of an aryl residue, an alkyl residue having 1 to 10 carbon atoms, an alkoxy residue having 1 to 10 carbon atoms, and a polyglycol residue having two to twelve carbon atoms. The structure of the alkyl residue can be linear, branched or cyclic. The structure of the alkoxy residue can be linear, branched or cyclic. The polyglycol residue is preferably a linear polyglycol residue, for example, methylene glycols, ethylene glycols, propylene glycols, and mixtures thereof. When $X^2$ is N; $R^3$ can be two independently selected residues each selected from the group consisting of an aryl residue, an alkyl residue having 1 to 10 carbon atoms, an alkoxy residue having 1 to 10 carbon atoms, and a polyglycol residue having two to twelve carbon atoms. When $X^2$ is N, $X^2$ and $R^3$ can be a cyclic group ($X^2$—$R^3$) having five or six members and optionally one or more additional heteroatoms. Examples of the $X^2$—$R^3$ cyclic group include but are not limited to pyrrolidinyls (including pyrrolidonyls), piperidinyls (including piperidinonyls), and morpholinyls.

In structural formula (I), Ar is selected from the group consisting of phenyl, napthyl, pyridyl, pyrrolidyl, furanyl, pyranyl, azepinyl, oxepinyl, imidizolyl, oxazolyl, pyrimidinyl, purinyl, and substituted groups thereof. For example, Ar can be phenyl, dimethoxyphenyl, chlorophenyl, dichlorophenyl, bromophenyl, hydroxyphenyl, trimethylphenyl, fluorophenyl, nitrophenyl, methoxyphenyl, dihydrobenzopyran, pyridine, dimethyl aminophenyl, aminophenyl, piperonyl, fluoromethoxyphenyl, acetamidophenyl, or carbomoylphenyl.

In structural formula (I), $R^9$ is selected from the group consisting of H, $CH_3$, $CH_2N(CH_3)_2$, and phenyl.

In still another embodiment of structural formula (I), $X^2$ is O and $R^3$ is a polyglycol residue (e.g., methylene glycol, ethylene glycol and/or propylene glycol). Preferably, the polyglycol residue ($R^3$) has a molecular weight of less than about 500 Daltons.

In one embodiment of structural formula (I), when $X^1$ is S, $X^2$ is O, $R^2$ is H, $R^3$ is $CH(CH_3)_2$, and $R^9$ is H, Ar is not 3,4-dichlorophenyl, i.e., the compound is not isopropyl 2-amino-4-(3,4-dichlorophenyl)thiophene-3-carboxylate (PKCzl-diCl).

In another embodiment, the compound has structural formula (II):

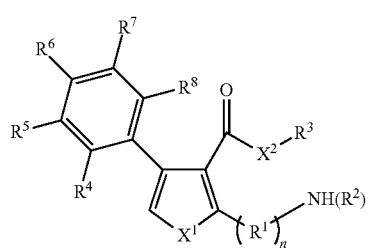

In structural formula (II), $X^1$ is selected from the group consisting of O, S, NH, and NMe. Preferably, $X^1$ is selected from the group consisting of O, S, and NH; more preferably $X^1$ is O, $X^1$ is S, or $X^1$ is NH.

In structural formula (II), n has a value of zero (0), one (1), or two (2). Preferably, n has a value of zero or one, more preferably n is equal to zero. When n is a value greater than zero, $R^1$ is selected from the group consisting of $CH_2$, $CH(CH_3)$, $C(CH_3)_2$, $C_2H_4$, and $C_2H_2$.

In structural formula (II), $R^2$ is selected from the group consisting of H, $CH_3$, $CH_2OH$, $C_2H_5$, $C_2H_5O$, $CH(CH_3)_2$, $C(CH_3)$, $CH_2CH(CH_3)_2$, and $CH_2C(CH_3)_3$. Preferably, $R^2$ is selected from the group consisting of H, $CH_3$, $CH_2OH$, and $C_2H_5$, more preferably $R^2$ is H.

In structural formula (II), $X^2$ is selected from the group consisting of O, S, NH and N; preferably $X^2$ is O. When $X^2$ is O, S or NH; $R^3$ is selected from the group consisting of an aryl residue, an alkyl residue having 1 to 10 carbon atoms, an alkoxy residue having 1 to 10 carbon atoms, and a polyglycol residue having two to twelve carbon atoms. The structure of the alkyl reside can be linear, branched or cyclic. The structure of the alkoxy residue can be linear, branched or cyclic. The polyglycol residue is preferably a linear polyglycol residue, for example, methylene glycols, ethylene glycols, propylene glycols, and mixtures thereof. When $X^2$ is N; $R^3$ can be two independently selected residues each selected from the group consisting of an aryl residue, an alkyl residue having 1 to 10 carbon atoms, an alkoxy residue having 1 to 10 carbon atoms, and a polyglycol residue having two to twelve carbon atoms. When $X^2$ is N, $X^2$ and $R^3$ can be a cyclic group ($X^2$—$R^3$) having five or six members and optionally one or more additional heteroatoms. Examples of the $X^2$—$R^3$ cyclic group include but are not limited to pyrrolidinyls (including pyrrolidonyls), piperidinyls (including piperidinonyls), and morpholinyls.

In structural formula (II), $R^4$ and $R^8$ are individually selected from the group consisting of H, F, Cl, OH, and $OCH_3$. Preferably, $R^4$ and $R^8$ are H.

In structural formula (II), $R^5$ and $R^7$ are individually selected from the group consisting of H, F, Cl, Br, $CH_3$, $C_2H_5$, OH, $OCH_3$, $OCH_2CH_3$, $OCH_2OCH_3$, $S(CH_3)_2^+$, and $N(alkyl)_3^+$. Preferably, one of $R^5$ and $R^7$ is H and the other is selected from the group consisting of F, Cl, Br, OH, $OCH_3$, $OCH_2CH_3$, $OCH_2OCH_3$, $S(CH_3)_2^+$, and $N(alkyl)_3^+$. In an alternative, $R^5$ and $R^7$ are the same and selected from the group consisting of H, F, Cl, Br, OH, $OCH_3$, $OCH_2CH_3$, $OCH_2OCH_3$, $S(CH_3)_2^+$, and $N(alkyl)_3^+$, preferably selected from the group consisting of H, F, Cl, Br, OH, $OCH_3$, $OCH_2CH_3$, $OCH_2OCH_3$, more preferably, selected from the group consisting of H, F, Cl, Br, OH, and $OCH_3$.

In structural formula (II), $R^6$ is selected from the group consisting of H, F, Cl, Br, $CH_3$, $C_2H_5$, $NO_2$, OH, $OCH_3$, $OCH_2CH_3$, $OCH_2OCH_3$, $OCH_2CH_2OH$, $OCH_2CH_2OCH_3$, $OCH_2CH_2OCH_2CH_3$, polyglycol residue selected from the group consisting of methylene glycols, ethylene glycols, propylene glycols and mixtures thereof, and an aryl group. Preferably, $R^6$ is selected from the group consisting of H, OH, $OCH_3$, $OCH_2CH_3$, $OCH_2OCH_3$, $OCH_2CH_2OH$, $OCH_2CH_2OCH_3$, $OCH_2CH_2OCH_2CH_3$, polyglycol, and an aryl group, more preferably, from the group consisting of OH, $OCH_3$, $OCH_2CH_3$, $OCH_2OCH_3$, $OCH_2CH_2OH$, $OCH_2CH_2OCH_3$, $OCH_2CH_2OCH_2CH_3$, and an aryl group, and even more preferably, from the group consisting of OH, $OCH_3$, $OCH_2CH_3$, $OCH_2OCH_3$.

In one embodiment of formula (II), when either $R^5$ or $R^7$ is Cl and the other is H, $R^6$ is not Cl. In another embodiment of formula (II), when either $R^5$ or $R^7$ is $OCH_3$ and the other is H, $R^6$ is not $OCH_3$. In still another embodiment of formula (II), when either $R^5$ or $R^7$ is Cl and the other is H, $R^6$ is not Cl; and when either $R^5$ or $R^7$ is $OCH_3$ and the other is H, $R^6$ is not $OCH_3$.

In still another embodiment, $X^2$ is O and $R^3$ is a polyglycol residue. Preferably, the polyglycol residue ($R^3$) is a methylene glycol, ethylene glycol and/or propylene glycol and has a molecular weight of less than about 500 Daltons.

In yet another embodiment, $X^2$ is O and $R^3$ is an alkyl group having a molecular weight in a range of 56 Daltons (D) to 170 D, 70 D to 170 D, or 84 D to 170 D. The alkyl group can be linear, branched, and/or cyclic. The selection from the groups, preferably, provide increased efficacy and increased solubility of the compound in physiologically acceptable solutions, e.g., physiologically acceptable saline solution. For example, when $X^1$ is S; $X^2$ is O; n is zero; $R^2$, $R^4$, $R^7$, and $R^8$ are H; the compound has increased solubility when $R^3$ is $C_3H_7$ and $R^5$ and $R^6$ are $OCH_3$. Alternatively, the increased solubility can be obtained when $R^3$ is polyglycol residue. Alternatively, the increased solubility can be obtained when $R^6$ is a polyglycol residue.

In still another embodiment, the compound is selected from the group of compounds having structural formula (III), structural formula (IV), structural formula (V), structural formula (VI), structural formula (VII), and structural formula (VIII):

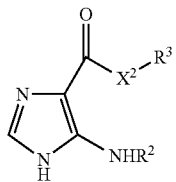
(III)

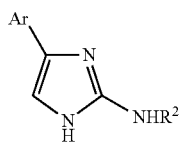
(IV)

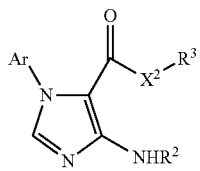
(V)

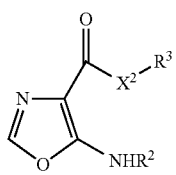
(VI)

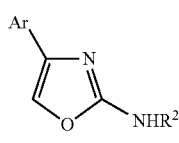
(VII)

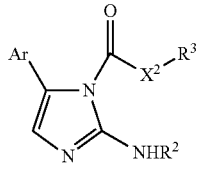
(VIII)

In structural formula (III) through structural formula (VIII), $R^2$ is selected from the group consisting of H, $CH_3$, $CH_2OH$, $C_2H_5$, $C_2H_5O$, $CH(CH_3)_2$, $C(CH_3)$, $CH_2CH(CH_3)_2$, and $CH_2C(CH_3)_3$. Preferably, $R^2$ is selected from the group consisting of H, $CH_3$, $CH_2OH$, and $C_2H_5$, more preferably $R^2$ is H.

In structural formula (III) through structural formula (VIII), $X^2$ is selected from the group consisting of O, S, NH and N; preferably $X^2$ is O. When $X^2$ is O, S or NH, $R^3$ is selected from the group consisting of an aryl residue, an alkyl residue having 1 to 10 carbon atoms, an alkoxy residue having 1 to 10 carbon atoms, and a polyglycol residue having two to twelve carbon atoms. The structure of the alkyl residue can be linear, branched or cyclic. The structure of the alkoxy residue can be linear, branched or cyclic. The polyglycol residue is preferably a linear polyglycol residue, for example, methylene glycols, ethylene glycols, propylene glycols, and mixtures thereof. When $X^2$ is N, $R^3$ can be two independently selected residues each selected from the group consisting of an aryl residue, an alkyl residue having 1 to 10 carbon atoms, an alkoxy residue having 1 to 10 carbon atoms, and a polyglycol residue having two to twelve carbon atoms. When $X^2$ is N, $X^2$ and $R^3$ can be a cyclic group ($X^2$—$R^3$) having five or six members and optionally one or more additional heteroatoms. Examples of the $X^2$—$R^3$ cyclic group include but are not limited to pyrrolidinyls (including pyrrolidonyls), piperidinyls (including piperidinonyls), and morpholinyls.

In structural formula (III) through structural formula (VIII), Ar is selected from the group consisting of phenyl, napthyl, pyridyl, pyrrolidyl, furanyl, pyranyl, azepinyl, oxepinyl, imidizolyl, oxazolyl, pyrimidinyl, purinyl, and substituted groups thereof.

In another embodiment, the compound has structural formula (IX):

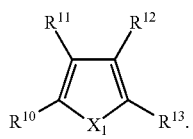
(IX)

In structural formula (IX), $X^1$ is selected from the group consisting of O, S, NH, and NMe. Preferably, $X^1$ is selected from the group consisting of O, S, and NH; more preferably $X^1$ is O, $X^1$ is S, or $X^1$ is NH.

In structural formula (IX), $R^{10}$ is selected from the group consisting of H, $CH_3$, $COCH_3$, and $C_5H_{10}N$.

In structural formula (IX), $R^{11}$ is selected from the group consisting of phenyl, chlorophenyl, dichlorophenyl, dimethylaminophenyl, aminophenyl, piperonyl, dimethoxyphenyl, methoxyphenyl, acetamidophenyl, carbomoylphenyl, fluoromethoxyphenyl, napthyl, pyridyl, pyrrolidyl, furanyl, pyranyl, azepinyl, oxepinyl, imidizolyl, oxazolyl, pyrimidinyl, purinyl, and substituted groups thereof.

In structural formula (IX), $R^{12}$ is selected from the group consisting of an aryl ester carboxylate, an alkyl ester carboxylate, an alkoxy ester carboxylate, an aryl carboxamide, an alkyl carboxamide, an alkoxy carboxamide, $C_2H_4NO$, and nitrile. For example, $R^{12}$ can be benzyl ester carboxylate, fluoro benzyl ester carboxylate, methoxy benzyl ester carboxylate, ethyl ester carboxylate, isopropyl ester carboxylate, benzyl carboxamide, methyl carboxamide, ethyl carboxamide, isopropyl carboxamide, $C_2H_4NO$, or nitrile.

In structural formula (IX), $R^{13}$ is selected from the group consisting of $NH_2$, $C_2H_3O$, $C_7H_4N_2O_3C_1$, $C_7H_4NOClF$, $C_6H_4N_2O_3Cl$, and $C_2H_4NO$. In one embodiment of structural formula (IX), when $R^{10}$ is $CH_3$, $R^{13}$ is not $C_2H_4NO$. In another embodiment of structural formula (IX), when $R^{12}$ is isopropyl carboxylate, $R^{11}$ is not 3,4-dichlorophenyl.

Examples of specific embodiments are provided by the following formulas:

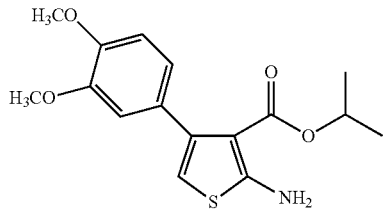

41
-continued
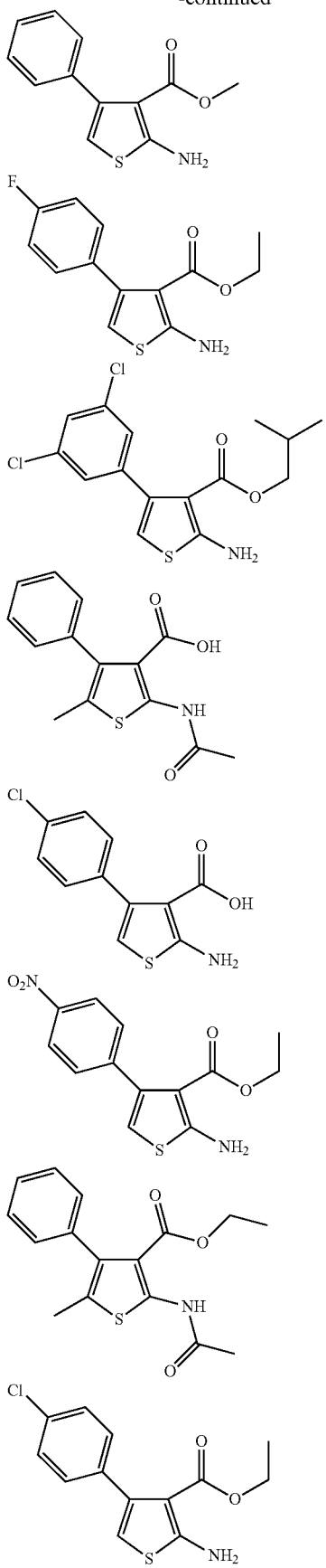
42
-continued
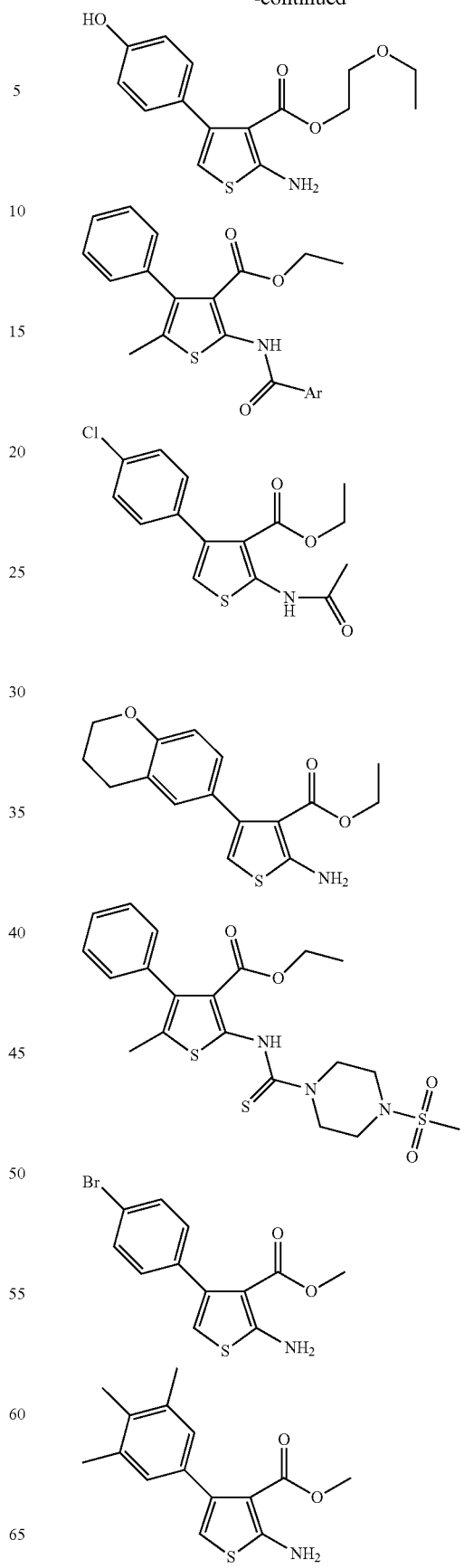

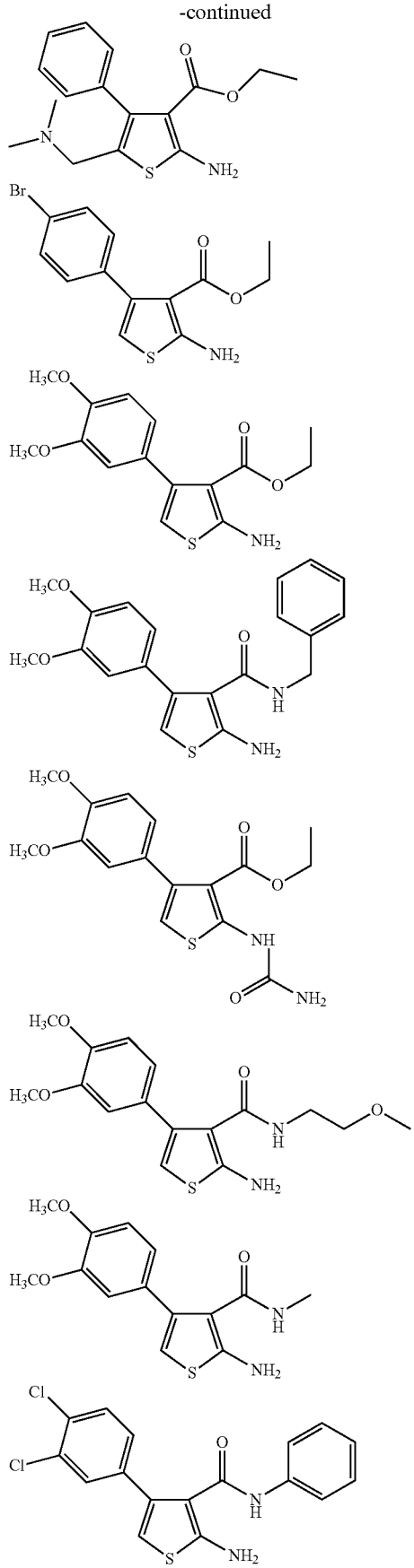
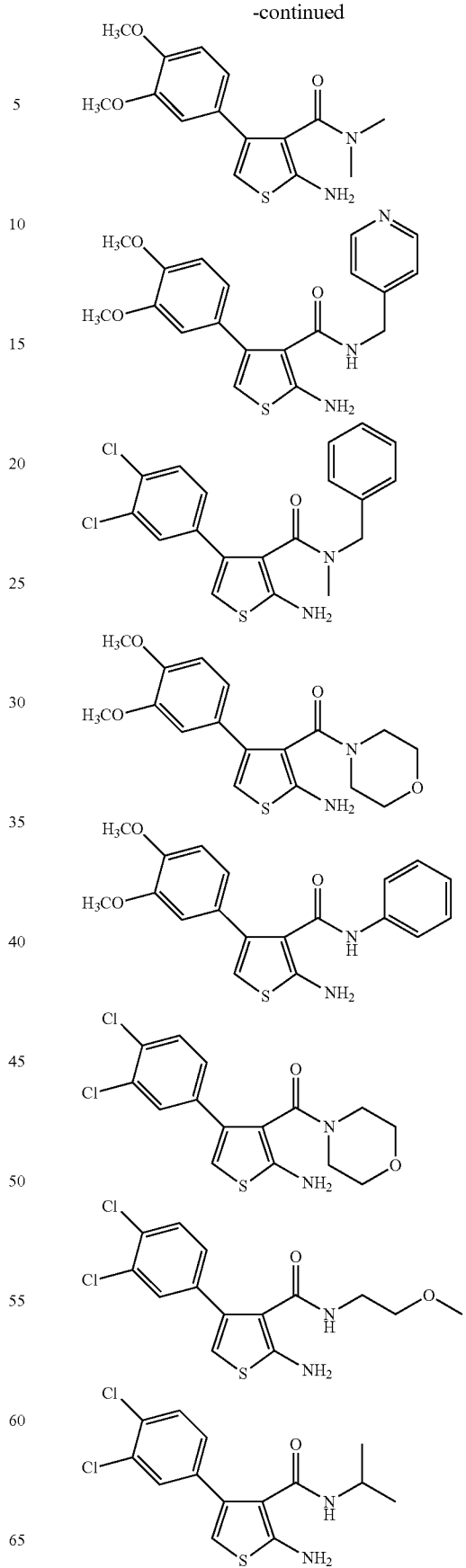

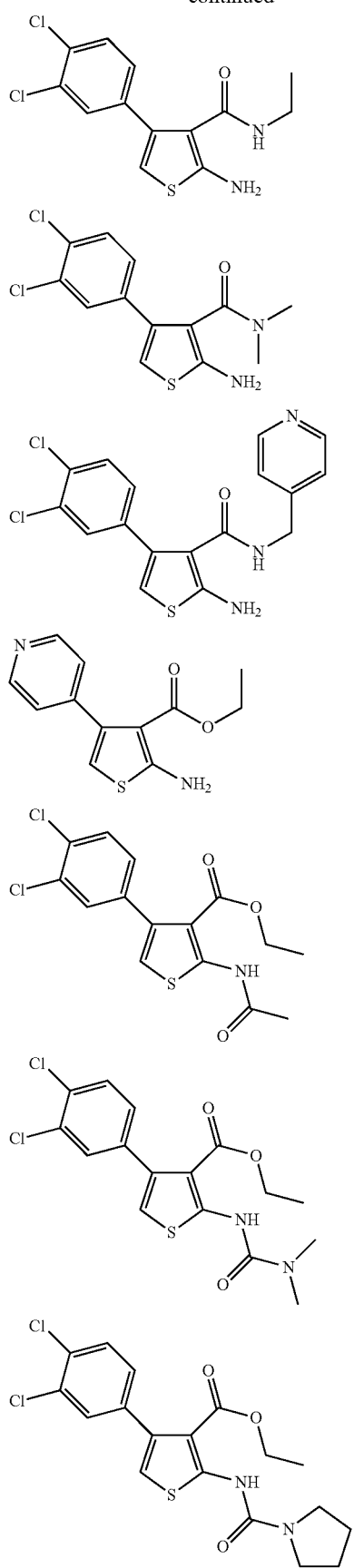
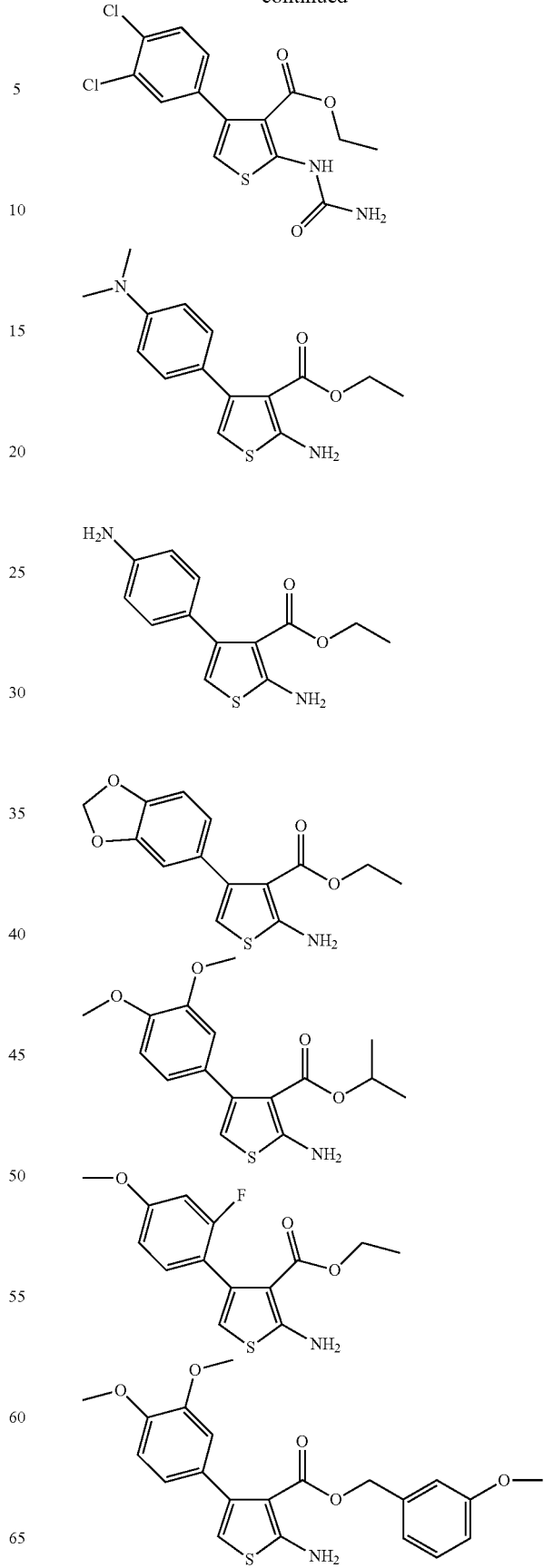

47
-continued
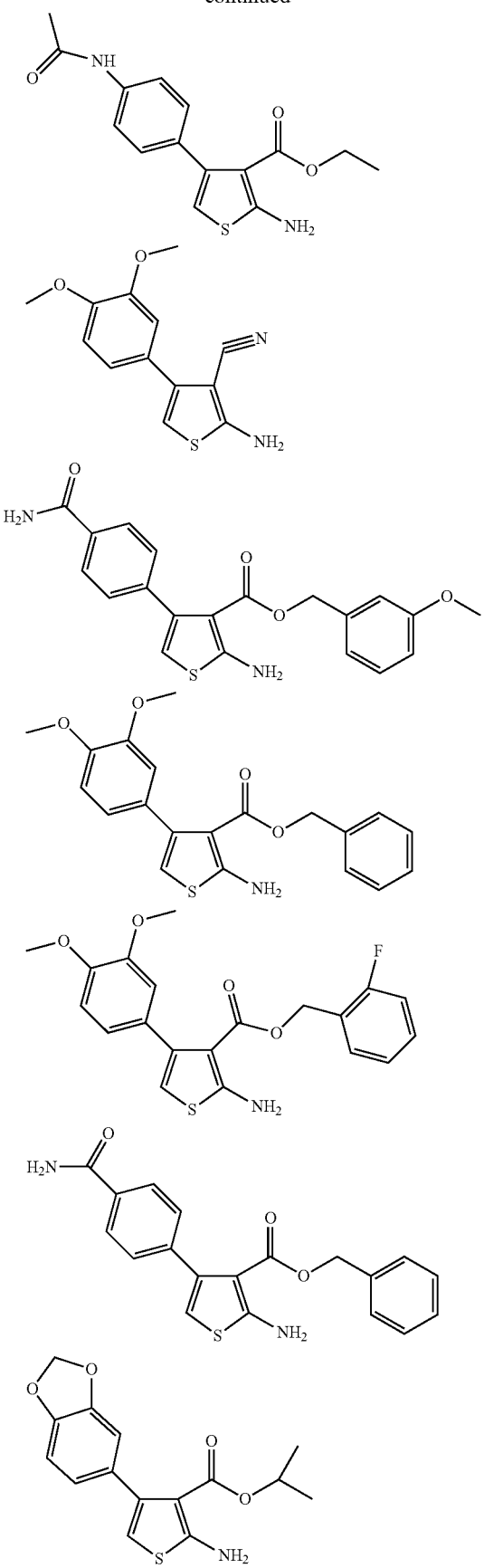
48
-continued
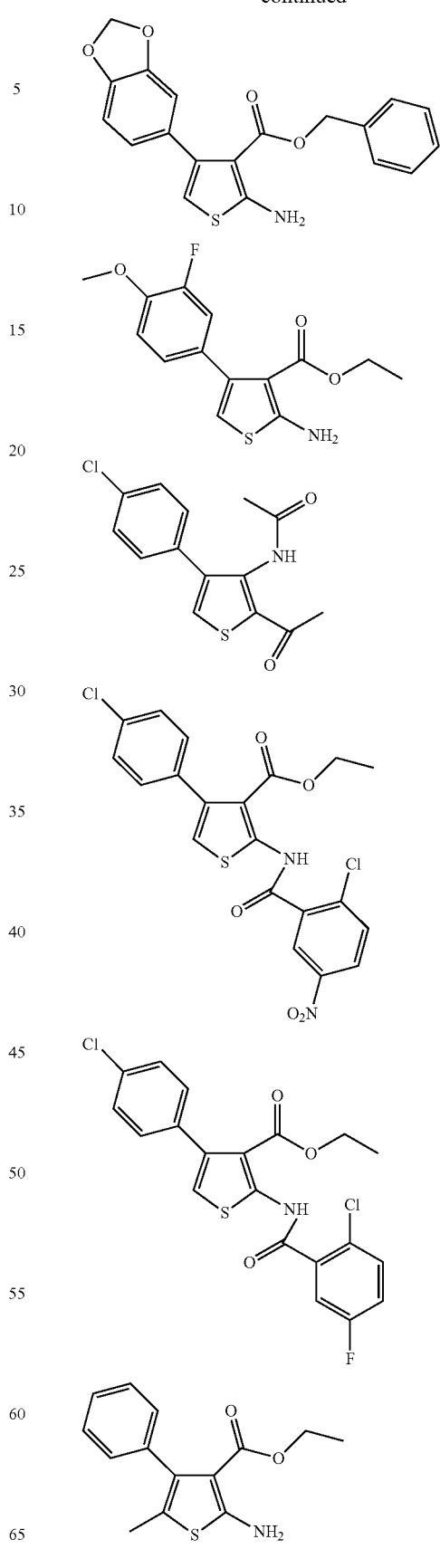

-continued

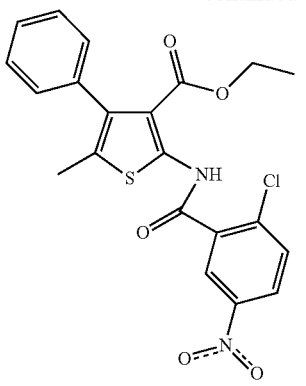

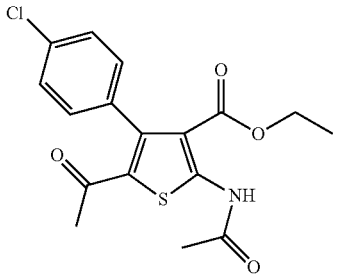

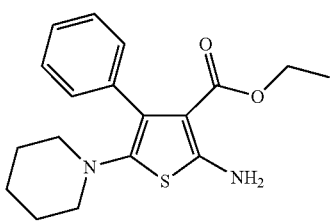

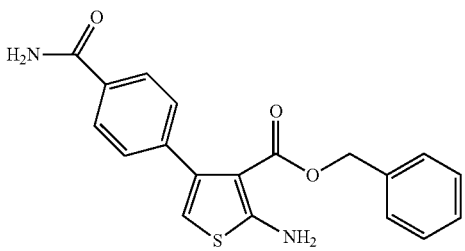

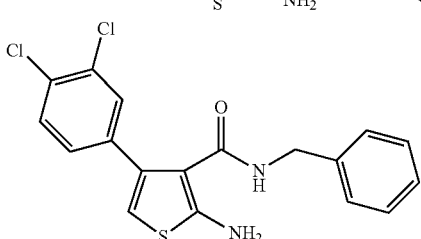

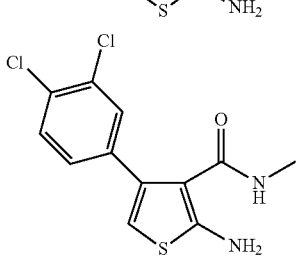

-continued

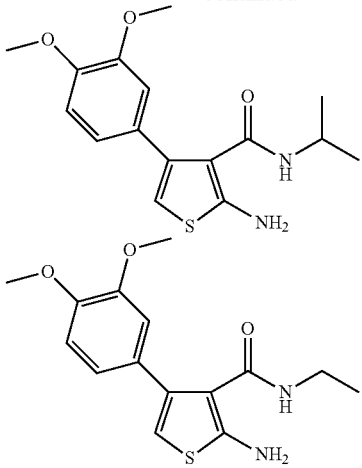

The method of inhibiting or reducing vascular permeability comprises administering to a subject a composition comprising an amount of a compound having any one of structural formulas (I) to (IX) effective to inhibit or reduce vascular permeability. As such, the vascular permeability may be associated with a disease or disorder characterized by abnormal vascular permeability in a subject. In one aspect, the method comprises administering to a subject in need thereof a composition comprising a compound having any one of structural formulas (I) to (IX) in an amount effective to treat or prevent the disease or disorder. In various embodiments, the subject is suffering from the disease or disorder and the composition is administered to reduce vascular permeability or slow the progress of vascular permeability (i.e., slow the deterioration of the microvascular barrier). Alternatively, in one aspect, the subject is at risk for a disease or disorder characterized by abnormal vascular permeability, and the composition is administered to prevent abnormal vascular permeability or slow the onset of vascular permeability. It will be appreciated that complete reversal or prevention of vascular permeability (or a disease or disorder characterized by abnormal vascular permeability) is not required to achieve a beneficial effect in a subject. Any degree of amelioration of the unwanted effects of vascular permeability, and any degree of inhibition of vascular permeability, is contemplated.

As used herein, "abnormal vascular permeability" is a physiological state characterized by increased passage of material across a vascular barrier (e.g., the blood-retinal barrier or blood-brain barrier) compared to that observed in a healthy subject. Optionally, the abnormal vascular permeability is induced by cytokines (e.g., VEGF or TNF) or other mode of aPKC activation leading to vascular permeability. Abnormal vascular permeability is assessed clinically, for example, by observing vascular leakage or detecting metabolites generally not found in a particular location in the body. Abnormal vascular permeability also is determined by, e.g., administering to a subject a substance known to be prevented from passing across a physiological barrier (e.g., a vascular barrier comprising tight junctions) and detecting the presence or absence of the substance in a location from which it is generally excluded in normal vasculature. Other methods of detecting and quantifying vascular permeability are known in the art.

In various embodiments, the vascular permeability and/or disease or disorder is associated with rearrangement or alteration of tight junctions within physiological barriers, such as the blood-brain barrier, blood-nerve barrier, and/or blood-retina barrier. Accordingly, in one aspect of the invention, the compound inhibits or reduces vascular permeability of the blood-brain barrier and/or the blood-retina barrier. Diseases or disorders associated with abnormal vascular permeability of the blood-retinal barrier include, but are not limited to, age-related macular degeneration (AMD), retinopathy of prematurity, macular edema (e.g., diabetic macular edema), diabetic retinopathy (proliferative and non-proliferative), uveitis (optionally caused by uveal infection), branch retinal vein occlusion, central retinal vein occlusion, ocular ischemic syndrome, and ocular reperfusion injury.

Diseases or disorders associated with abnormal vascular permeability of the blood-brain barrier include, but are not limited to, ischemia-reperfusion injury, neoplastic diseases, and brain edema. For example, ischemia-reperfusion injury is commonly associated with a stroke. Abnormal vascular permeability in stroke patients is often observed during release of a vessel obstruction and subsequent reperfusion. Ischemic conditions also stem from stenosis.

Neoplastic diseases and disorders have been observed to be associated with abnormal permeability of tight junctions. See, e.g., Soler et al., *Carcinogenesis,* 20(8); 1425-31 (1999). Neoplastic diseases and disorders include, but are not limited to, adenocarcinomas, arrhenoblastomas, astrocytomas, basal cell carcinomas, bladder carcinomas, breast carcinomas, cervical carcinomas, choriocarcinoma, colorectal carcinomas, endometrial carcinoma, endometrial hyperplasia, esophageal carcinomas, fibrosarcomas, gastric carcinomas, glioblastomas, carcinomas of the head and neck, hemangiomas, hemangioblastomas, hepatoblastomas, Kaposi's sarcoma, kidney carcinomas, laryngeal carcinomas, leiomyosarcomas, leukemias, liver carcinomas, lung carcinomas, lymphomas, medulloblastomas, melanomas, nasopharyngeal carcinomas, neuroblastomas, oligodendrogliomas, osteogenic sarcomas, ovarian carcinomas, pancreas carcinomas, prostate carcinomas, renal cell carcinoma, retinoblastomas, rhabdomyosarcomas, Schwannomas, squamous cell carcinomas, thecomas, thyroid carcinomas urinary tract carcinomas and uterine carcinomas. In one aspect, the disease or disorder is a brain tumor (e.g., a primary or a secondary brain tumor). Inhibiting or reducing vascular permeability associated with a brain tumor, in various aspects, inhibits leakage into the brain (brain edema) and/or spread of cancerous cells.

Optionally, the disease or disorder is a microvascular complication of a systemic condition in the subject, such as diabetes. The methods described herein optionally comprise administering the composition comprising a compound having any one of structural formulas (I) to (IX) soon after a disease or disorder (e.g., the systemic condition giving rise to the microvascular complication) is diagnosed. For example, the high blood glucose level in diabetics causes an increase in growth factors in their eyes. This condition is known as the "pre-diabetic retinopathy stage" and can lead to retinopathy, if not prophylactically treated. Thus, in one aspect, the composition is administered as soon as a pre-diabetic retinopathy state is detected as a prophylactic measure. Similarly, if the disease or disorder is cancer, as described below, the composition is administered as soon as cancer markers or a tumor is detected.

The invention also provides a method of inhibiting aPKC. The activity of a compound against aPKC is determined using any suitable assay, such as an assay that measures PKC-mediated phosphorylation of a synthetic and/or natural substrate for the PKC enzyme. The PKC enzyme can be synthetic, recombinant, or naturally occurring. PKC assays may be performed on a biological sample containing PKC, cultured primary cells and/or tissues, or cell lines. Exemplary assays for characterizing the inhibitory activity of a compound are further described herein and in, e.g., Sando et al., "Enzyme Assays for Protein Kinase C Activity," in *Methods of Molecular Biology*, Alexandra Newton, Ed., Chapter 6, Volume 233, Humana Press, Totowa, N.J. (2003). In various embodiments, the compound of the invention inhibits aPKC-lambda, aPKC-iota, aPKC-zeta, or a combination of any of the foregoing. For example, in one aspect of the invention, the compound inhibits aPKC-iota. Alternatively or in addition, the compound inhibits aPKC-zeta. It will be appreciated that complete inhibition of aPKC is not required. Optionally, the compound has an $IC_{50}$ of about 50 µM or less, about 25 µM or less, about 20 µM or less, about 15 µM or less, about 10 µM or less, about 5 µM or less, or about 1 µM or less. In one aspect, the compound is selective for aPKC (and/or selective for one of the three aPKC isoforms), or inhibits aPKC activity better than activities of other PKC subfamilies. In various aspects, the compound has an $IC_{50}$ for aPKC that is five-fold or more less (e.g., 10-fold or more less, 20-fold or more less, or 50-fold or more less) than the $IC_{50}$ for other PKC families. For example, in one aspect, the compound exhibits an $IC_{50}$ of 10 µM for PKC-zeta, while having an $IC_{50}$ of greater than 100 µM for PKC-delta and/or PKC-beta. In various aspects, the compound inhibits growth factor-induced phosphorylation of a tight junction protein (e.g., occludin) by aPKC.

The method of inhibiting aPKC comprises contacting an aPKC (e.g., aPKC-iota or aPKC-zeta) with a compound (or multiple compounds) having the structural formula described herein. The aPKC is, in various embodiments, in vitro, in a cell or tissue, or in vivo. Optionally, the aPKC is present in cells collected from a biological sample, such as a tissue biopsy or bodily fluid (e.g., blood, plasma, serum, saliva, mucous, semen, tears, an ocular exudate, a tumor exudate, ascites fluid, lymph and urine).

In another aspect of the invention, the invention includes a method of treating or preventing inflammation. The method comprises administering to a subject a composition comprising a compound having any one of structural formulas (I) to (IX) in an amount effective to inhibit inflammation. The compounds described herein are potent aPKCζ inhibitors. Atypical PKCζ plays a critical role in activation of the NF-kB pathway. See, e.g., Leitges et al., *Mol. Cell,* 8:771-780 (2001) and Martin et al., *EMBO J.,* 21: 4049-4057 (2002). NF-kB activation mediates a host of cellular responses, including immunity and inflammation, and aberrant NF-kB function has been linked to cancer, autoimmune disease, septic shock, and viral infection. The invention includes a method of treating and preventing inflammation and associated diseases in a subject in need thereof. Diseases and disorders characterized by inflammation include, but are not limited to, allergic disorders, arthritis (e.g., rheumatoid arthritis), asthma, sepsis, chronic obstructive pulmonary disease, bronchopulmonary dysplasia, cystic fibrosis, interstitial lung disease, ear nose and throat diseases, conjunctivitis, skin diseases, rheumatic diseases, vasculitis, cardiovascular diseases, gastrointestinal diseases (e.g., inflammatory bowel disease), urologic diseases, diseases of the central nervous system, endocrine diseases, urticaria, anaphylaxis, angioedema, dysmenorrhoea, multiple trauma, pain, bacterial infections, fungal infections, viral infections, sickle cell anemia, and hypereosinofilic syndrome. The ability of a compound to reduce or inhibit inflammation can be determined using any suitable assay, including assays known in the art. Exemplary inflammation assays are described in the Example. Inflammation in vivo is determined by, for example, measuring inflammatory markers, such as C-Reactive Protein (CRP), fibrinogen, interleukins (e.g., IL-6), and erythrocyte sedimentation rate. Inflammation also is evaluated using magnetic resonance imaging (MRI).

The invention further includes a method for treating or preventing (in whole or in part) metabolic disorders (or symptoms thereof). Atypical PKC, e.g., aPKC regulates lipogenic and gluconeogenic pathways and is activated by insulin in the liver. See, e.g., Sajan et al., *Diabetologia,* 52:1197-1207 (2009). Suppression of aPKC activity to reduce kinase hyperactivity can treat lipid and carbohydrate abnormalities. Metabolic disorders include, but are not limited to, diabetes, insulin resistance, obesity, impaired insulin signaling, hyperglycemia, hyperinsulinemia, hepatosteatosis, hypertriglyceridemia, hypercholesterolemia and metabolic syndrome, all of which are associated with aberrant aPKC function. See, e.g., Farese et al., *J. Clin. Invest.,* 117:2289-301 (2007)

The invention also includes a method of inhibiting cancer cell proliferation. The method comprises contacting a population of cancer cells with a compound having a structure selected from the group consisting of structural formula (I) to (IX) in an amount effective to inhibit cancer cell proliferation. When the cancer cells are present in a subject (e.g., a mammalian (human or non-human subject)), the population of cancer cells is contacted by administering the compound (generally in the form of a composition) to the subject. The cancer cell is, in various embodiments, a transformed cell of any of the neoplastic diseases identified herein. In one aspect, the cancer cell is part of a tumor, e.g., a solid tumor or a tumor associated with soft tissue (i.e., soft tissue sarcoma). The tumor can be associated with cancers of (i.e., located in) the oral cavity and pharynx, the digestive system, the respiratory system, bones and joints (e.g., bony metastases), soft tissue, the skin (e.g., melanoma), breast, the genital system, the urinary system, the eye and orbit, the brain and nervous system (e.g., glioma), or the endocrine system (e.g., thyroid) and is not necessarily the primary tumor. Tissues associated with the oral cavity include, but are not limited to, the tongue and tissues of the mouth. Cancer can arise in tissues of the digestive system including, for example, the esophagus, stomach, small intestine, colon, rectum, anus, liver, gall bladder, and pancreas. Cancers of the respiratory system can affect the larynx, lung, and bronchus and include, for example, non-small cell lung carcinoma. Tumors can arise in the uterine cervix, uterine corpus, ovary vulva, vagina, prostate, testis, and penis, which make up the male and female genital systems, and the urinary bladder, kidney, renal pelvis, and ureter, which comprise the urinary system. The cancer cell also may be associated with lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like).

In various embodiments, the compound inhibits tumor cell proliferation, inhibits tumor vascularization, inhibits tumor growth, and/or promotes reduction in the size of at least one tumor. Methods of identifying and quantifying cancer cell proliferation are known in the art and described in, e.g., U.S. Patent Application Publication No. 20110092566. Animal models of cancer also are known in the art and include, e.g., the mouse melanoma metastasis model (Lee et al., *Cancer Chemother. Pharmacol.,* 57(6): 761-71 (2006)) and the canine model of human invasive urinary bladder cancer (Mohammed et al., *Mol. Cancer Ther.,* 2(2): 183-188 (2003)). Tumor growth can be ascertained using any suitable method, such as those methods currently used in the clinic to track tumor size and cancer progress. Tumor size can be figured using any suitable technique, such as measurement of dimensions, or estimation of tumor volume using available computer software. Tumor size is determined by tumor visualization using, for example, CT, ultrasound, SPECT, spiral CT, MRI, photographs, and the like. Measurement of tumor size, detection of new tumors, tumor antigens, or markers (e.g., CEA, PSA, or CA-125), biopsy, surgical downstaging, PET scans, and the like can point to the overall progression (or regression) of cancer in a human. Radioimmunodetection (RAID) is used to locate and stage tumors using serum levels of markers (antigens) produced by and/or associated with tumors ("tumor markers"), e.g., carcinembryonic antigen (CEA), and can be useful as both a pre-treatment diagnostic predicate and a post-treatment diagnostic indicator of recurrence.

Thus, the invention includes a method of inhibiting invasion, ingrowth, and/or metastasis of cancer cells. The method comprises administering to a subject a compound of any one of structural formulas (I) to (IX) in an amount effective to inhibit invasion, ingrowth, and/or metastasis of cancer cells. In various embodiments, the compound inhibits or slows the ingrowth of cancer cells into surrounding tissue or collagen or fibrin-rich interstitial and temporary matrixes. "Inhibiting" cancer cell invasion does not require a 100% abolition of invasion or metastasis. Any decrease in cancer cell invasion constitutes a beneficial biological effect in a subject.

The invention further includes a method of inhibiting angiogenesis in a subject. The method comprises administering to a subject in need thereof a compound of any one of structural formulas (I) to (IX) in an amount effective to inhibit angiogenesis. Numerous assays are known in the art for evaluating the ability of a compound to inhibit angiogenesis. Ocular neovascularization, for instance, can be detected using fluorescein angiography, color Doppler imaging, and by clinical examination. Additional examples of methods for detecting and quantifying angiogenesis are described in, e.g., U.S. Patent Application Publication No. 20090258006.

"Inhibiting" angiogenesis or cell proliferation does not require a 100% abolition of blood vessel formation or cell proliferation. Any decrease in unwanted angiogenesis constitutes a beneficial biological effect in a subject. In this regard, the invention reduces the formation of new blood vessels or blood vessel growth by, e.g., at least about 5%, at least about 10% or at least about 20% compared to levels observed in the absence of the inventive method (e.g., in a biologically-matched control subject or specimen that is not exposed to the compound of the inventive method). In some embodiments, the formation of new blood vessels or blood vessel growth is reduced by at least about 30%, at least about 40%, at least about 50%, or at least about 60%. In some embodiments, the inventive method inhibits angiogenesis by at least about 70%, at least about 80%, at least about 90%, or more (about 100%) compared to new blood vessel formation in the absence of the compound of the inventive method. Similarly, the compound, in various aspects, inhibits cancer cell proliferation by at least about 5%, at least about 10%, at least about 20%, at least about 30%, at least about 40%, at least about 50%, at least about 60%, at least about 70%, at least about 80%, or at least about 90%.

The inventive method includes any clinically-acceptable route of administration of the composition to the subject (e.g., mammalian subject, such as humans, non-human primates, cats, dogs, cows, horses, rodents, pigs, and sheep). In various aspects, the route of administration is systemic, e.g., oral or by injection. A composition may be administered intravenously, intraperitoneally, subcutaneously, intrathecally, intramuscularly, or intraportally. Alternatively or in addition, the route of administration is local, e.g., topical, intra-tumor, peri-tumor, intraocular, periocular (e.g., subTenon's capsule), intravitreal, subconjunctival, subretinal, suprachoroidal, otic, or retrobulbar. The manner in which the composition is administered is dependent, in part, upon the cause and/or location of, e.g., the abnormal vascular permeability or angiogenesis. For example, to prevent or slow the onset of vascular permeability or disorders resulting therefrom (e.g., retinopathy) linked to systemic conditions (e.g., diabetes), the composition is administered systemically, e.g., orally or by injection. Alternatively or in addition, in various aspects, the composition is administered locally, at, or near a site of abnormal vascular permeability. For example, the composition is administered locally, e.g., via eye drops or intraocular injection, to one or both eyes of a subject having or at risk of having macular edema associated with diabetic retinopathy. Routes of local administration to the central nervous system include epidural, intracerebral, and intracerebroventricular administration, optionally via injection or sustained administration via a shunt.

The method includes administering an effective amount of the compound (or composition comprising the compound) to achieve a desired biological response, e.g., an amount effective to alleviate, ameliorate, or prevent, in whole or in part, a symptom of a condition to be treated, e.g., abnormal vascular permeability, metabolic disorders, inflammation, cancer cell proliferation, or angiogenesis. In various aspects, the amount of the compound of any one of structural formulas (I) to (IX) administered is about 0.001 mg/kg to about 100 mg/kg body weight (e.g., about 0.01 mg/kg to about 10 mg/kg or about 0.1 mg/kg to about 5 mg/kg). The compound or composition of the invention may be manufactured and/or administered in single or multiple unit dose forms.

The invention further comprises a composition comprising the compound of any one of structural formulas (I) to (IX) and a pharmaceutically-acceptable carrier, e.g., a pharmaceutically-acceptable excipient, carrier, binder, and/or diluent. Optionally, the composition includes a free acid, free base, salt (e.g., an acid or base addition salt), hydrate or prodrug of the compound in any one of structural formulas (I) to (IX). The prodrug is a material that includes the compound in any one of structural formulas (I) to (IX) covalently bound to a carrier moiety. The carrier moiety can be released from the compound in any one of structural formulas (I) to (IX) in vitro or in vivo to yield compound in any one of structural formula (I) to (IX). Prodrug forms are well known in the art as exemplified in Sloan, K. B., *Prodrugs*, M. Dekker, New York, 1992; and Testa, B. and Mayer, J. M., *Hydrolysis in drug and prodrug metabolism: chemistry, biochemistry, and enzymology*, Wiley-VCH, Zurich, 2003.

Optionally, the composition comprises one or more additional therapeutic agents. Similarly, in various aspects of the invention, the method comprises administering one or more additional therapeutic agents, which may be present in the composition comprising the compound of any one of structural formulas (I) to (IX) or administered in a separate composition. For example, the composition may include more than one aPKC inhibitor, such as two or more non-peptide inhibitors of aPKC (e.g., two or more compounds selected from any of structural formulas (I) to (IX)). Alternatively or in addition, the composition includes a non-peptide aPKC (e.g., aPKCι or aPKCζ) inhibitor and a peptide inhibitor of aPKC. In another embodiment, the composition includes one or more inhibitors of a "calcium-dependent" isoform of PKC, also called conventional or cPKC isoforms (e.g., PKCα, PKCβ, and/or PKCγ); and/or an inhibitor of a "calcium-independent" isoform, also called novel or nPKC isoforms (e.g., PKCδ, PKCε and/or PKCη). Examples of suitable inhibitors of cPKC include, but are not limited to, bisindoylmaleimides, such as bisindoylmaleimide I. Bisindoylmaleimide I is known in the art and obtained by standard organic synthetic methods or obtained commercially, such as from Calbiochem Corp., La Jolla, Calif. Exemplary inhibitors of PKCβ include, but are not limited to, Bisindoylmaleimide I, LY379196, and ruboxistaurin and salt forms thereof such as ruboxistaurin mesylate, also known as LY333531.

In one aspect, the method comprises administering an antineoplastic agent, which may be present in the compound composition or provided in a separate composition using the same or a different route of administration. Antineoplastic therapeutic agents include, but are not limited to, alkylating agents, antibiotics, folate inhibitors, purine analogs, pyrimidine analogs, and radiosensitizing compounds. Specific antineoplastic therapeutic agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, droloxifene, dromostanolone, duazomycin, edatrexate, eflornithine, elsamitrucin, enloplatin, enpromate, epipropidine, epirubicin, erbulozole, esorubicin, estramustine, estramustine, etanidazole, etoposide, etoposide, etoprine, fadrozole, fazarabine, fenretinide, floxuridine, fludarabine, fluorouracil, fluorocitabine, fosquidone, fostriecin, fulvestrant, gemcitabine, gemcitabine, hydroxyurea, idarubicin, ifosfamide, ilmofosine, interleukin II (IL-2, including recombinant interleukin II or rIL2), interferon alpha-2a, interferon alpha-2b, interferon alpha-n1, interferon alpha-n3, interferon beta-1a, interferon gamma-I b, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, methotrexate, metoprine, meturedepa, mitindomide, mitocarcin, mitocromin, mitogillin, mitomalcin, mitomycin, nitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, puromycin, pyrazofurin, riboprine, rogletimide, safingol, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, torernifene, trestolone, triciribine, triethylenemelamine, trimetrexate, triptorelin, tubulozole, uracil mustard, uredepa, vapreotide, verteporlin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin. These and other antineoplastic therapeutic agents are described, for example, in *Goodman & Gilman's The Pharmacological Basis of Therapeutics*, McGraw-Hill Professional, 10th ed., 2001.

Other exemplary additional therapeutic agents include, but are not limited to, glucocorticoids, kallikrein inhibitors, corticosteroids (e.g., prednisone, methylprednisolone, dexamethasone, or triamcinalone acetinide), anti-inflammatory agents (such as noncorticosteroid anti-inflammatory compounds (e.g., ibuprofen or flubiproben)), vitamins and minerals (e.g., zinc), and anti-oxidants (e.g., carotenoids (such as a xanthophyll carotenoid like zeaxanthin or lutein)). Other examples of anti-inflammatory agents include agents that inhibit tumor necrosis factor (TNF) activity, such as adalimumab (HUMIRA®), infliximab (REMICADE®), certolizumab (CIMZIA®), golimumab (SIMPONI®), and etanercept (ENBREL®). Neutralizing proteins to growth factors, such as a monoclonal antibody that is specific for a given growth factor, e.g., VEGF (for an example, see Aiello et al., *PNAS USA*, 92: 10457-10461 (1995)), or phosphotyrosine (Dhar et al., *Mol. Pharmacol*, 37: 519-525 (1990)), are suitable for co-administration or incorporation into a composition, if desired. Other various additional therapeutic compounds include cytokine modulators, an endothelial cell-specific inhibitor of proliferation (e.g., thrombospondin), an anti-proliferative peptide (e.g., SPARC and prolferin-like peptides), a glutamate receptor antagonist, aminoguanidine, an angiotensin-converting enzyme inhibitor (e.g., angiotensin II), an angiogenesis inhibitor, a sulphonylurea oral hypoglycemic agent (e.g., gliclazide (non-insulin-dependent diabetes)), aspirin, aldose reductase inhibitors (such as tolrestat, SPR-210, or sorbinil), and retinoic acid and analogues thereof. Subjects exhibiting systemic fluid retention, such as that due to cardiovascular or renal disease and severe systemic hypertension, can be additionally treated with diuresis, dialysis, cardiac drugs and antihypertensive agents. The additional therapeutic agent may be a pharmaceutically acceptable salt, ester, amide, hydrate, and/or prodrug of any of these or other therapeutic agents.

The composition according to the invention includes about 0.1 wt. % to 99 wt. % of the compound of any one of structural formulas (I) to (IX). For example, in various aspects, the composition includes a compound of any one of structural formulas (I) to (IX) or a mixture thereof in an amount less than about 100 wt. % and greater than or equal to about 5 wt. %, about 10 wt. %, about 15 wt. %, about 20 wt. %, about 25 wt. %, about 30 wt. %, about 35 wt. %, about 40 wt. %, about 45 wt. %, about 50 wt. %, about 55 wt. %, about 60 wt. %, about 65 wt. %, about 70 wt. %, about 75 wt. %, about 80 wt. %, about 85 wt. %, about 90 wt. %, or about 95 wt. % of the composition.

A composition according to the invention may be formulated in various forms. In this regard, the invention includes a formulation for oral, subcutaneous, topical, or intraocular administration comprising a pharmaceutically-acceptable excipient and a compound of any one of structural formulas (I) to (IX). Optionally, the formulation further comprises a delayed release agent. The invention also provides a method of preparing the formulation comprising admixing the pharmaceutically acceptable excipient and the compound of any one of structural formulas (I) to (IX), and lyophilizing the admixture.

A composition formulated for oral administration may be a solid, semi-solid or liquid formulation prepared according to methods known in the art. Solid dosage forms for oral administration include capsules, tablets, pills, powders, and granules. In such solid dosage forms, the compound is admixed with at least one pharmaceutically acceptable carrier such as a filler or extender, e.g., starches, lactose, sucrose, glucose, mannitol, and silicic acid; a binder, e.g., carboxymethylcellulose, alginates, gelatin, polyvinylpyrrolidone, sucrose, and acacia; a humectant, e.g., glycerol; a disintegrating agent, e.g., agar-agar, calcium carbonate, plant starches such as potato or tapioca starch, alginic acid, certain complex silicates, and sodium carbonate; a solution retarder, e.g., paraffin; an absorption accelerator, e.g., quaternary ammonium compounds; a wetting agent, e.g., cetyl alcohol, glycerol monostearate, and glycols; an adsorbent, e.g., kaolin and bentonite; a buffering agent, e.g., sodium citrate and dicalcium phosphate; and/or a lubricant, e.g., talc, calcium stearate, magnesium stearate, solid polyethylene glycols and sodium lauryl sulfate.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions include, but are not limited to, polymeric substances and waxes.

The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied with a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the invention to achieve delivery of the active to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as, but not limited to, hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers (e.g., formed from acrylic acid), methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. Examples of enteric coating material are acrylic acid polymers and copolymers available under the trade name EUDRAGIT®, Roehm Pharma (Germany). The EUDRAGIT® series L, L-30D S copolymers, and cross-linked polymers, see for example U.S. Pat. No. 6,136,345, are insoluble in the stomach and dissolve in the intestine. The enteric coating optionally contains a plasticizer to prevent the formation of pores and cracks that allow the penetration of the gastric fluids into the solid dosage. In particular, a coating composed of an anionic carboxylic acrylic polymer typically contains approximately 10% to 25% by weight of a plasticizer, particularly dibutyl phthalate, polyethylene glycol, triethyl citrate and/or triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

Liquid dosage forms for oral administration include, e.g., emulsions, solutions, suspensions, syrups, or elixirs. In addition to the compound of any one of structural formulas (I) to (IX), the liquid dosage forms optionally contain one or more pharmaceutically acceptable carriers, such as water or other solvents, solubilizing agents and emulsifiers, such as, for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and/or other such conventional pharmaceutical ingredients. A composition formulated for oral administration also may include adjuvants, such as wetting agents, emulsifying and suspending agents, sweetening, flavoring, and perfuming agents.

In various embodiments, the composition including one or more compounds of any one of structural formula (I) to (IX) is formulated as a physiologically acceptable sterile solution, dispersion, suspension, emulsion, or sterile powder for reconstitution into a sterile solution or dispersion. Sterile solutions or dispersions are suitable for injection (e.g., subcutaneous, intramuscular, intravenous, intracerebral, or intraocular injection). Sterile solutions or dispersions also are suitable for topical application to, e.g., the eye. Exemplary formulations include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, corn, olive, petrolatum, and mineral.

The composition alternatively is formulated as an intraocular formulation, sustained-release formulation, or formulated for delivery via a device (see, e.g., U.S. Pat. No. 5,378,475). For example, gelatin, chondroitin sulfate, a polyphosphoester, such as bis-2-hydroxyethyl-terephthalate (BHET), or a polylactic-glycolic acid (in various proportions) is used to formulate sustained-release formulations. Implants (see, e.g., U.S. Pat. Nos. 5,443,505, 4,853,224 and 4,997,652), devices (see, e.g., U.S. Pat. Nos. 5,554,187, 4,863,457, 5,098,443 and 5,725,493), such as an implantable device, e.g., a mechanical reservoir, an intraocular device or an extraocular device with an intraocular conduit (e.g., 100 m-1 mm in diameter), or an implant or a device comprised of a polymeric composition as described above, are suitable for use.

The process of formulating the composition can include admixing a pharmaceutically acceptable excipient and the compound having a structure selected from the group consisting of structural formulas (I) to (IX). The compound can first be admixed with a solvent capable of dissolving or dispersing the compound, or the admixture of the excipient and the compound can be admixed with the solvent. Lyophilizable materials (e.g., solvents) can be removed from the admixture of the excipient and the compound by lyophilization. The resulting materials can be a solid formulation of the excipient and the compound.

The invention is further described in the following example. The example serves only to illustrate the invention and is not intended to limit the scope of the invention in any way.

EXAMPLE

This example describes a method of identifying an aPKC inhibitor and characterizing activity of a compound against aPKC isoforms. The example further illustrates a method of inhibiting or reducing vascular permeability using a compound of the invention.

Reagents and Methods

Reagents

Recombinant human $VEGF_{165}$ was purchased from R&D Systems (Minneapolis, Minn., USA). LY294002 and PKCζ myristoylated pseudosubstrate inhibitor (PKCζ-PS) were purchased from Calbiochem (Gibbstown, N.J., USA). Candidate compounds and raw materials were purchased from ChemBridge Corporation (San Diego, Calif., USA) and Sigma-Aldrich (St. Louis, Mo., USA) or synthesized by Apogee, Inc. (Hershey, Pa., USA) or Evotec, Inc. (San Francisco, Calif., USA). Candidate compounds were synthesized using standard organic synthetic methods according to the general schemes described in, e.g., U.S. Pat. No. 7,585,865, the entire disclosure of which is incorporated herein by reference, particularly with respect to compound synthesis methods, and Rannard and Davis, *Organic Letters*, 2:2117-2120 (2000). Complete protease inhibitor cocktail tablets from Roche (Indianapolis, Ind., USA) were used. All other chemical reagents were obtained from Sigma-Aldrich (St. Louis, Mo., USA).

Primary Retinal Endothelial Cell (REC) Culture

Primary bovine retinal endothelial cells (BREC) were isolated from fresh bovine eye tissue. Human retinal endothelial cells (HREC) were from Cell Systems (Krikland, Wash., USA). Cells were grown in MCDB-131 complete media (Sigma-Aldrich, Mo., USA) containing 10% fetal bovine serum, 10 ng/ml epidermal growth factor, 200 μg/ml Endogro (Vec Technologies, Rensselaer, N.Y., USA), 90 μg/ml heparin, antibiotics and antimycotics. For experimentation, cells were grown to confluence and serum starved for 24 hours with 100 nM hydrocortisone and treated with VEGF at 50 ng/ml where indicated. All experiments were performed with cells at passage 5-8.

In Vitro Permeability Assay

RECs were plated onto 0.4 μm Transwell filters (Corning Costar, Acton, Mass., USA) and grown to confluence. Following treatments, 70 kDa rhodamine β isothiocyanate-dextran (RITC-Dextran) was added to the apical chamber and samples were collected from the basolateral chamber at 30 minute intervals for 4 hours. The rate of flux of the substrate, Po, was calculated over the 4 hour time course from the following formula.

$$P_o = [(F_L/\Delta t)V_A]/(F_A A)$$

where $P_o$ is in centimeters per second; $F_L$ is basolateral fluorescence; $F_A$ is apical fluorescence; $\Delta t$ is change in time; A is the surface area of the filter (in square centimeters); and $V_A$ is the volume of the basolateral chamber (in cubic centimeters).

Over Expression of Pkcζ in Primary Retinal Endothelial Cells

BREC were transfected with the PKCζ expression plasmid pCMV-PKCζWT, using the nuclefection technique (AMAXA Biosystems, Gaithersburg, Md., USA) with the HCAEC kit conditions. Cells were plated onto 0.4 µm Transwell filters (Corning Costar, Acton, Mass., USA) and medium changed at 16 hours. Alternatively, BREC were infected at 90% confluence on Transwell filters with AdGFP, wildtype PKCζ (AdWTPKCζ), kinase-dead PKCζ (AdKD-PKCζ) and constitutively active PKCζ (AdCAaPKCζ), at a MOI of about 10,000 to 20,000 for 6 hours followed by serum starvation for 24 hours. Cells were allowed to grow to confluence and permeability assays were performed as described above.

Cell Lysis and Immunoblot Analysis

Cells were harvested in extraction buffer containing 100 mM NaCl, 1% Triton X-100, 0.5% Sodium Deoxycholate, 0.2% SDS, 2 mM EDTA, 10 mM HEPES (pH 7.5), 1 mM sodium orthovanadate, 10 mM sodium fluoride, 10 mM sodium pyrophosphate, 1 mM benzamadine, 1 complete protease inhibitor tablet, 10 µM LR-microcystin. Following protein extraction, Western blot utilizing the NuPAGE system (Invitrogen, Carlsbad, Calif., USA) was performed. Protein content was determined using DC protein assay (BioRad, Hercules, Calif., USA) and equal amounts of protein were loaded in 4-12% Bis-Tris gradient gels. Following electrophoresis and transferring to nitrocellulose, membranes were blocked in milk with 5% Tris-buffered saline with 0.1% Tween 20. Membranes were immunoblotted using anti-Flag (Cell Signaling, Danvers, Mass., USA), anti-HA (Cell Signaling, Danvers, Mass., USA), anti-phospho ERK1/2 (Cell Signaling, Danvers, Mass., USA), anti-total ERK1/2 (Cell Signaling, Danvers, Mass., USA), anti-phospho aPKC (Cell Signaling, Danvers, Mass., USA), total PKCζ (Santa Cruz, Santa Cruz, Calif., USA), and anti-actin (Millipore, Billerica, Mass., USA) antibodies. Primary antibodies were detected by horseradish peroxidase-conjugated anti-rabbit and chemiluminescence with ECL Advance (GE Healthcare, Piscataway, N.J., USA) or anti-mouse IgG alkaline phosphatase with ECF (GE Healthcare, Piscataway, N.J., USA).

Immunoprecipitation

Male Sprague-Dawley rats (Charles River Laboratories, Wilmington, Mass., USA) were anesthetized with ketamine and xylazine (66.7 mg and 6.7 mg/kg body weight, intramuscular), and a 32-gauge needle was used to create a hole for an intra-vitreal injection (2.5 µl/eye) using a 5-µl Hamilton syringe. Animals received an intra-vitreal injection of either vehicle (0.1% BSA/PBS) or VEGF (50 ng) for the time indicated. Retinas were excised and lysed in 1% Nonidet P-40, 10% glycerol, 50 mm Tris, pH 7.5, 150 mm NaCl, 2 mm EDTA, 1 mm NaVO4, 10 mm sodium fluoride, 10 mm sodium pyrophosphate, 1 mm benzamidine, complete protease inhibitor mixture. The lysate was centrifuged at 14,000×g for 10 minutes, and the supernatant was transferred to another microcentrifuge tube. Protein (750 µg) was subjected to a preclear with 100 µl of 1:1 slurry of Protein G-Sepharose™ 4 Fast Flow (GE Healthcare, Pittsburgh, Pa., USA) for one hour, after brief micro-centrifugation the supernatant was incubated with 5 µg aPKC Ab (C-20) for two hours. Protein G beads were added, followed by further incubation for one hour. The beads were recovered by centrifugation at 1500×g for 1 minute and washed four times with 1 ml of lysis buffer. Proteins bound to Protein G were eluted by boiling in Laemmli buffer for five minutes then used to Western blot, as described above.

In Vivo Permeability Assay

Male Sprague-Dawley rats (Charles River Laboratories, Wilmington, Mass., USA) weighing 150 to 175 g were used to evaluate retinal vascular permeability and tight junction proteins localization in retinal blood vessels. Animals were housed under a 12-hour light/dark cycle with free access to water and a standard rat chow. All experiments were conducted in accordance with the Association for Research in Vision and Ophthalmology (ARVO) Statement for the Use of Animals in Ophthalmic and Vision Research, and were approved and monitored by the Institutional Animal Care and Use Committee (IACUC) at the Penn State College of Medicine. Rats were anesthetized with ketamine and xylazine (66.7 mg and 6.7 mg/kg body weight, intramuscular), and a 32-gauge needle was used to create a hole for an intra-vitreal injection (2.5 µl/eye) using a 5-µl Hamilton syringe. Animals received an intra-vitreal injection of either vehicle (PBS), VEGF (50 ng), PKC-zeta inhibitor pro-drug (PKCζI-PD) at 103.8 ng or 259.5 ng to yield an estimated final vitreous concentration of 10 µM or 25 µM, assuming 30 µl vitreous volume, or a dichloro-substituted PKC-zeta inhibitor (PKCζI-diCl) at 247.5 ng to yield 25 µM estimated vitreous concentration. Experimental groups received both inhibitor and VEGF simultaneously. The animals recovered for 3 hours and then were anesthetized again for permeability assay. Blood-retinal barrier permeability was assessed by measuring retinal Evan's Blue dye accumulation. Animals received femoral vein injection of 45 mg/kg body weight of Evans blue in sterile PBS. After 2 hours, the animals were anesthetized and the abdominal cavity was opened and 1 ml blood was drawn from the inferior vena cava to obtain plasma Evans blue concentration. Animals were perfused for 2 minutes through the heart with citrate buffer (50 mM, pH 3.5, 37° C.) containing 1% paraformaldehyde. Retinas were harvested from both eyes and dried overnight in a Savant Speed-Vac. Retinas were weighed and Evans blue was extracted with 150 µl formamide at 70° C. overnight. The extract was transferred to an Ultrafree-MC filter tube and centrifuged at 5,000×g for 2 hours at 4° C. Absorbances were measured with a Beckman DU640B spectrophotometer and background-subtracted absorbance of Evans blue was obtained by subtracting the minimum absorbance (740 nm) from the maximum absorbance (620 nm). The concentration of Evans blue was determined from a standard curve of Evans blue in formamide. Retinal permeability was calculated and expressed in µl plasma/g dry retina weight/hr circulation.

Library Screen for PKCζ Inhibitors and In Vitro High-Throughput (HT) Kinase Assay The DIVERSet collection of 50,000 compounds from Chembridge (San Diego, Calif.) was screened for PKCζ inhibition using recombinant human PKCζ from Enzo Life Sciences (Plymouth Meeting, Pa.), CREBtide from Enzo Life Sciences (Plymouth Meeting, Pa.) as a substrate and a final concentration of 100 µM for each candidate compound. The Kinase-Glo luminescence kit from Promega (Madison, Wis.) was used to measure residual ATP levels following three hours at room temperature kinase reaction. Hits were defined as compounds that inhibited PKCζ activity by at least 50%, and these were further characterized in dose-response assays to determine their potencies. Further structure-activity relationships (SAR) were performed using Kinase-Glo® luminescence kit (Promega, Madison, Wis. USA) with PKCζ (125 ng/ml), ATP (0.1 µM), and CREBtide (25 µM). Specificity profiling was performed by Millipore Corporation, using a $^{32}P$ radio-labeled kinase assay at the $Km_{app}$ ATP for all human kinase isoforms.

Enzyme Kinetic Studies

ADP Quest™ assay (Discover Rx, Fremont, Calif., USA) was used to determine inhibitor mechanism of action. Briefly, for ATP competition, candidate compounds were serially diluted and incubated for 1 hour at 30° C. with 500 ng/ml PKCζ, 100 µM CREBtide, in the presence of a serial dilution of ATP. Substrate competition was performed using similar conditions with a serial dilution of candidate compound and 250 µM ATP, 500 ng/ml PKCζ and a serial dilution of CREBtide. In both competition assays ADP formation was measured by the addition of ADP reagent A and reagent B and read on SpectraMax M5 (Molecular Devices, Sunnyvale, Calif., USA) in kinetic mode reading fluorescence at excitation/emission 530/590 every 2.5 minutes. The signal obtained was converted to rate ($[RFU-RFU_{control}]$/time) and plotted against substrate concentration. $RFU_{control}$ is the signal obtained in the absence of kinase at the respective substrate competition. The data were fitted to the Michaelis-Menten equation using Prism software (Graphpad Software, La Jolla, Calif., USA) to obtain $K_m$ values: Rate=$V_{max}$*[S]/S+$K_m$. The results of ADP Quest™ assays are illustrated in FIGS. 2A, 2B, 4A, 4B, 5A, and 5B.

Immuno-Cytochemistry and Confocal Microscopy

Tight junction cellular localization was assessed by immunocytochemistry. Cells were grown to confluence on plastic coverslips then placed in step down media with Endogro (ZO-1) or without Endogro (occludin) for 24 hours. Cells were treated as indicated then fixed with 1% paraformaldehyde for 10 minutes at room temperature, followed by permeabilization with 0.2% Triton X-100 for ZO-1 or pre-extracted with high sucrose buffer fixed with ethanol on ice for 30 minutes for occludin. Following blocking with 10% goat serum (ZO-1) or 10% BSA (occludin) in 0.1% TritonX-100, cells were stained with a rat monoclonal ZO-1 antibody for 24 hours or occludin for 2 days. Cells were washed and incubated for 60 minutes with a goat anti-rat Alexa-fluor 647 (Invitrogen, Carlsbad, Calif., USA)-conjugated secondary antibody (ZO-1) or Cy3 donkey anti rabbit (occludin) for 24 hours. Imaging was accomplished using a Leica confocal microscope (TCS SP2 AOBS; Leica; Wetzlar, Germany) and image processing was achieved using Leica imaging software (Leica Microsystems, Buffalo Grove, Ill., USA). Occludin localization in retinal vessels was assessed by immunohistochemistry in whole retinas. The retinas were incubated with monoclonal anti-occludin (1:50) for three days at 4° C. Primary antibodies were detected with Cy2-conjugated anti-mouse IgG (Jackson Immunoresearch Laboratories, West Grove, Pa., USA) for 24 hours at 4° C. After incubation, retinas were washed, mounted in slides with Aqua Poly/Mount and analyzed on a Leica TCS SP2 AOBS confocal microscope and displayed as collapsed serial images.

Assessment of Cell Viability

The LIVE/Dead viability kit (Invitrogen, Carlsbad, Calif., USA) was used to assess cell viability, according to manufacturer's instructions. Briefly, cells were exposed to candidate compound for 24 hours and 48 hours then incubated with 1 µM calcein-acetoxymethyl ester (calcein AM) and 2 µM ethidium homodimer (EthD-1) for 30 minutes at room temperature. The membrane-permeant calcein AM is cleaved only by live cells to yield green fluorescence, while EthD-1 only enters damaged membranes and undergoes a 40-fold enhancement of fluorescence upon binding to DNA. The fluorescence was measured in a SpectraMax M5 (Molecular Devices, Sunnyvale, Calif., USA) with calcein AM ex/em at 494/517 and EthD-1 ex/em at 528/617 nm.

Statistical Analysis of Data

Experiments were performed in duplicate or triplicate with the indicated sample number (n) indicated. Statistical analysis was carried out using Prism software from Graphpad using one-way analysis of variance (ANOVA) with the Tukey post test. A p-value of less than 0.05 was considered statistically significant. $IC_{50}$ values were calculated using variable slope Sigmoidal Dose-Response curve. $K_i$ values were derived by plotting the effect of varying substrate concentration on enzyme activity in the presence of varying concentrations of inhibitor [I]. The data was fitted using global nonlinear regression for noncompetitive inhibition with the following equations:

$$Rate = V\text{max app}*[S]/(Km+[S])$$

$$V\text{max app} = V\text{max}/(1+[I]/K_i)$$

TNF/VEGF Permeability Assay

BREC were plated onto 0.4 µm Transwell filters (Corning Costar, Acton, Mass., USA) and grown to confluence. Following 30 minutes of pretreatment with candidate compound, cells were subjected to 5 ng/ml TNFα (R&D Systems, Minneapolis, Minn., USA) for one hour, then 50 ng/ml VEGF (R&D Systems) for 30 minutes. Following treatments, 70 kDa Rhodamine β isothiocyanate-dextran (RITC-Dextran) was added to the apical chamber, and samples were collected from the basolateral chamber at 30 minute intervals for four hours. The rate of flux of the substrate, Po, was calculated over the four-hour time course from the following formula:

$$Po = [FL/\text{delta}(t))VA]/(FAA)$$

where Po is in centimeters per second; FL is basolateral fluorescence; FA is apical fluorescence; delta(t) is change in time; A is the surface area of the filter (in square centimeters); and VA is the volume of the basolateral chamber (in cubic centimeters).

TNF-Induced NF-kB Activation Assay $HEK_{293}pNF$-kBluc cells (Panomics, Fremont, Calif., USA) were cultured according to the manufacturer's protocol. Cells were seeded onto 96-well plates in phenol red-free DMEM containing high glucose (Sigma) for 24 hours prior to assay. Cells were exposed to a candidate compound for three hours. Following treatment, cells were stimulated with 5 ng/ml TNF (R&D Systems) for five hours. Cells were then lysed with Bright-Glo™ luciferase reagent (Promega, Madison, Wis., USA) and luminescent values were obtained using a GloMax® instrument using standard protocol for Bright-Glo™ luciferase reagent. Values were background corrected and normalized to TNF treatment alone and represented as % NF-kB activity.

Results aPKC Isoforms Contribute to VEGF-Induced Retinal Endothelial Permeability To directly determine if PKCζ contributes to VEGF-induced permeability, BREC were treated with VEGF and western blotting was performed over a time course to determine activation utilizing a phospho-specific antibody to pThr403/410 to monitor PKCζ activation. VEGF activates aPKC isoforms by inducing phosphorylation of aPKC at Thr403/Thr410 in its activation loop. Normal VEGF signaling was verified in these cells as demonstrated by a robust increase in phosphorylated ERK1/2. Expression plasmid for FLAG-tagged wild-type PKCζ was transfected into BREC, and the cells were grown to confluence on 0.4 μm Transwell filters. VEGF treatment of control cells increased the permeability of the monolayer to 70 kDa RITC-Dextran approximately 1.5-2.0-fold, an effect that was significantly potentiated with the overexpression of wild-type PKCζ. Furthermore, BREC were transduced with recombinant adenoviruses containing a wild-type PKCζ (AdWTPKCζ), kinase-dead PKCζ mutant (AdDNPKCζ), and a constitutively active mutant of PKCζ (AdCAPKCζ). Adenovirus-mediated overexpression of AdDNPKCζ completely prevented the VEGF-induced permeability to 70 kDa RITC-Dextran in primary cell culture. In addition, AdCAPKCζ alone increased basal permeability in BREC demonstrating that overexpression of active PKCζ is sufficient to alter permeability in retinal endothelial cells. In order to investigate if aPKC isoforms contribute to VEGF-induced retinal permeability in vivo, Sprague-Dawley rats were intra-vitreally injected with VEGF and retinas were excised and probed for autophosphorylation of aPKC at Thr560/Thr555. Bovine retinal endothelial cells express PKCι, but do not express PKCζ. VEGF induced aPKC autophosphorylation within 15 minutes and was maximal at 30 minutes with an approximately three-fold increase relative to control. The aPKC phosphorylation site, Thr410, was probed using a phospho-specific antibody to pThr412 PKCζ. VEGF increased phosphorylation of this residue within 15 minutes and returned to basal following longer time points.

Peptide Inhibition of aPKC Isoforms Prevents VEGF-Induced Retinal Endothelial Permeability To determine if aPKC kinase activity is essential for the VEGF-induced increase in endothelial permeability, a pseudosubstrate (PS), peptide inhibitor of PKCζ (PKCζ-PS) was used to block the kinase activity of the enzyme. PKCζ-PS is a myristoylated peptide corresponding to the auto-inhibitory pseudosubstrate domain of aPKC isoforms. BREC were grown to confluence on Transwell filters, and cells were treated with the indicated dose of PKCζ-PS for 30 minutes prior to VEGF treatment. Permeability to 70 kDa RITC-Dextran was measured over 4 hours, starting 30 minutes following addition of VEGF. Dose-response of PKCζ-PS administration was performed. At 50 nM, the PKCζ inhibitor was able to significantly reduce the VEGF-induction of BREC permeability.

Identification and Characterization of Small Molecule Inhibitors of aPKC

To identify small molecule inhibitors of aPKC, a 50,000 member chemical library from Chembridge was screened for compounds that inhibit aPKCζ kinase activity in an in vitro assay. Initially, a library screen of compounds was performed at a concentration of 100 μM using purified recombinant aPKCζ and 25 μM CREBtide as a PKC substrate. The Kinase-Glo® luminescence kit was used to measure residual ATP levels following 3 hour room temperature incubation. "Hits" were defined as compounds that inhibited aPKCζ activity by at least 50%, and these were further characterized in dose-response assays to determine their potencies and specificities. A total of 14 compounds with $IC_{50}$ values of 100 μM or less were identified representing a 0.03% hit rate, and a group of compounds with molecular weights below 500 that showed structural similarity were identified. A number of the compounds contained a phenyl-thiophene core structure. Screening was focused on phenyl-thiophene derivatives and additional compounds were synthesized.

Figure 3:
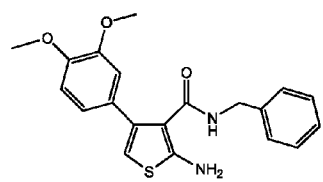
FIG. 3 depicts chemical structures of compounds assayed for aPKC inhibitory activity.
Figure 3:
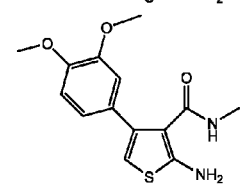
Figure 3:
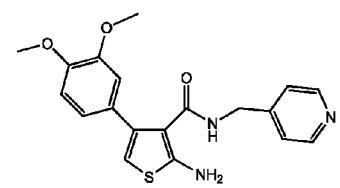
Figure 3:
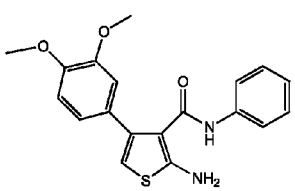
Figure 3:
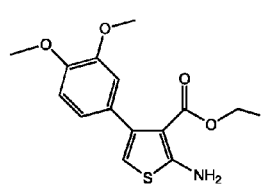
Figure 3:
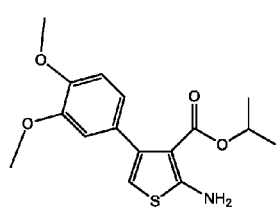
Figure 3:
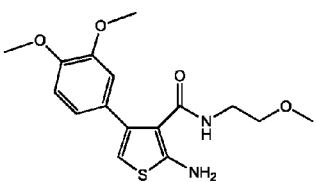
Figure 3:
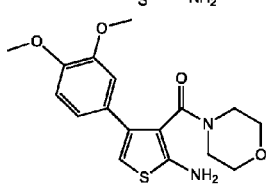
Figure 3:
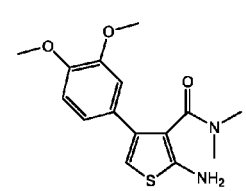
Figure 3:
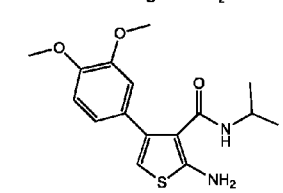
Figure 3:
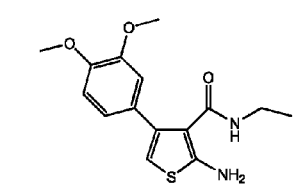
Figure 4A:
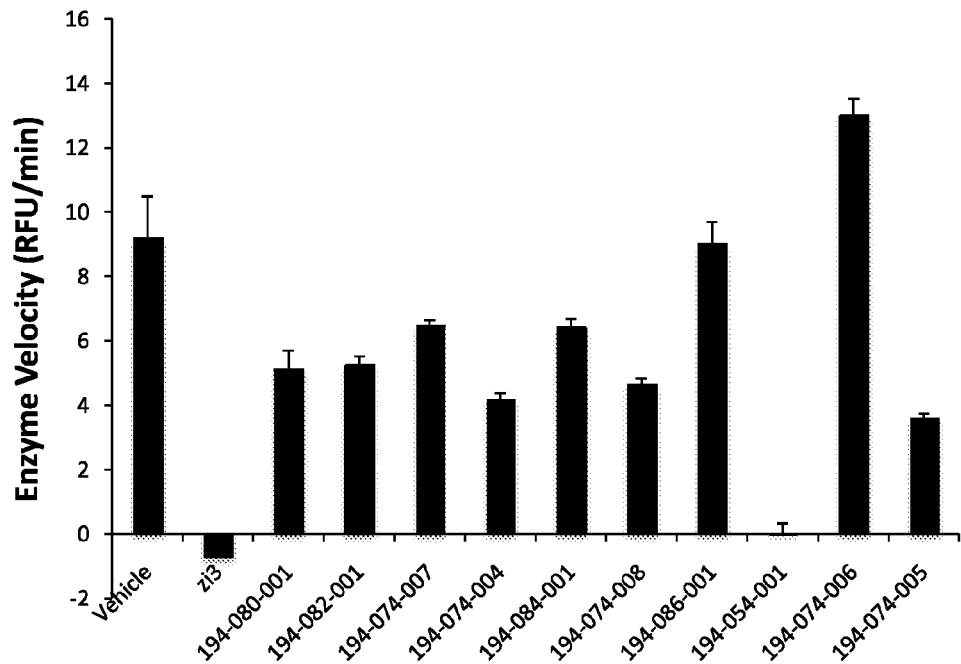
FIGS. 4A and 4B are bar graphs illustrating ADP Quest™ test results for the compounds of FIG. 3.
Figure 4B:
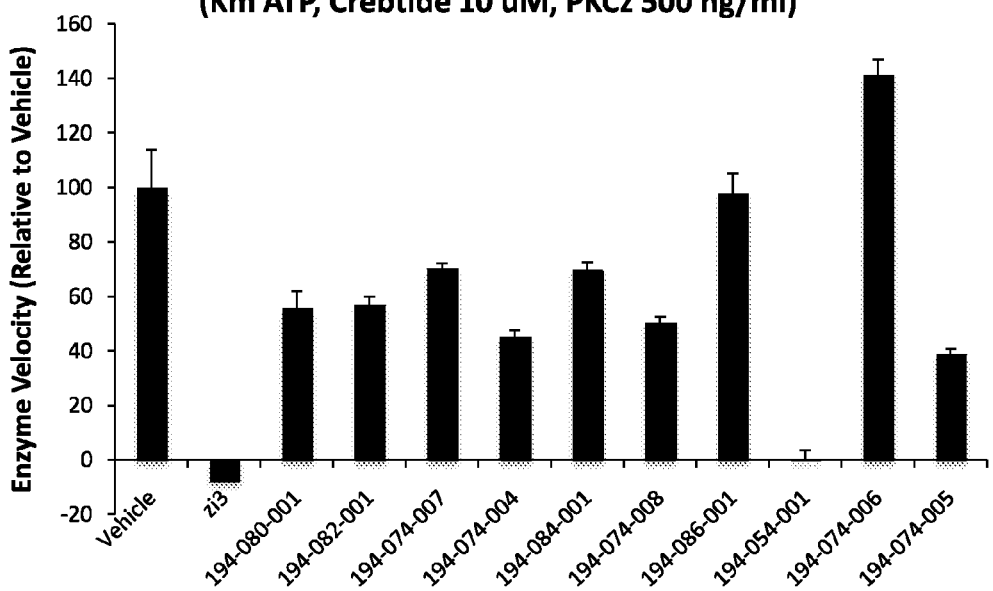
Figure 5A:
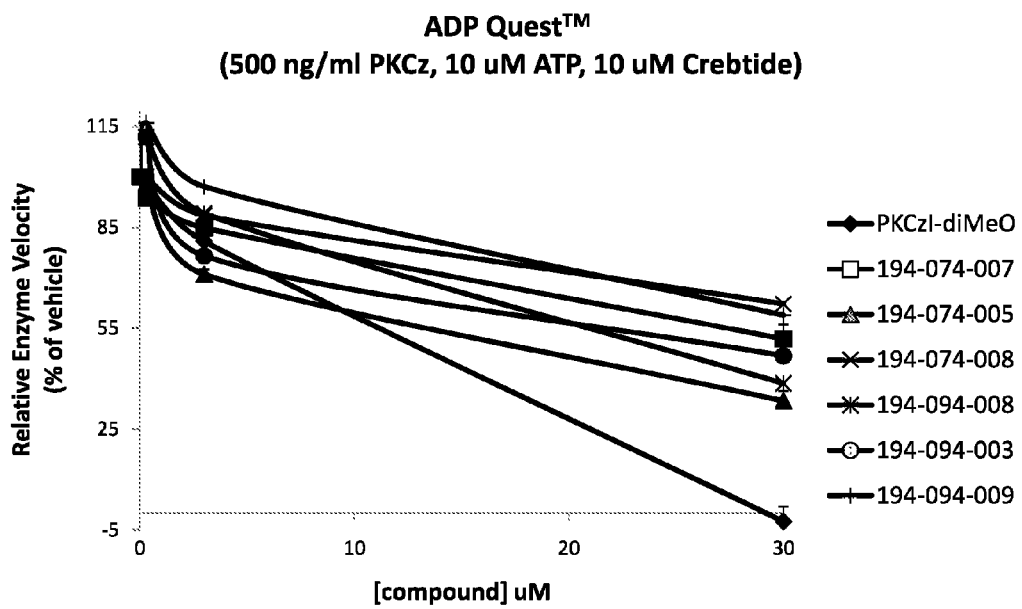
FIGS. 5A and 5B are line graphs illustrating ADP Quest™ test results for select compounds of FIGS. 1 and 3.
Figure 5B:
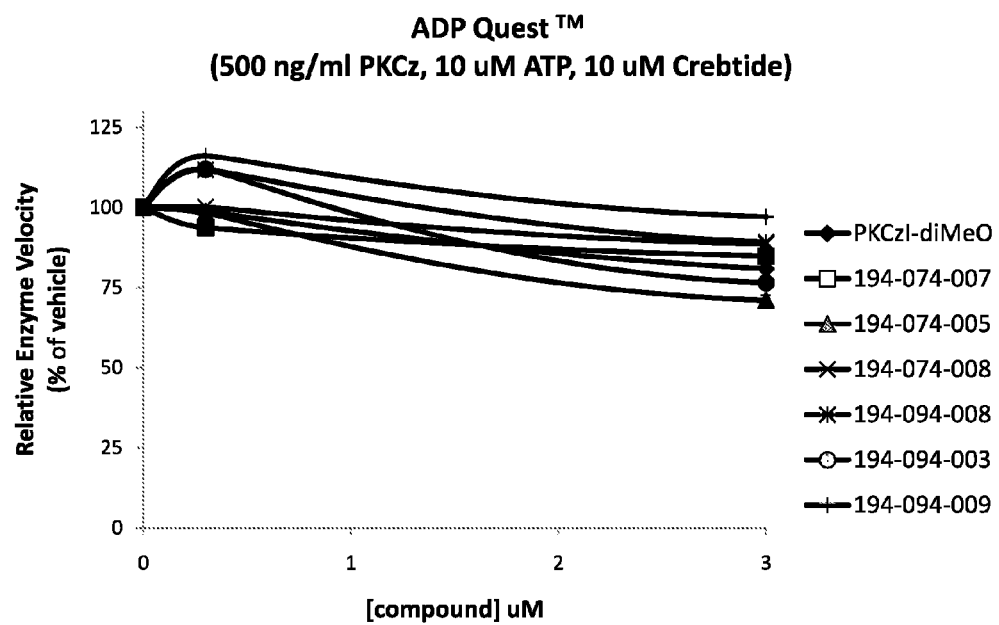
Figure 7:
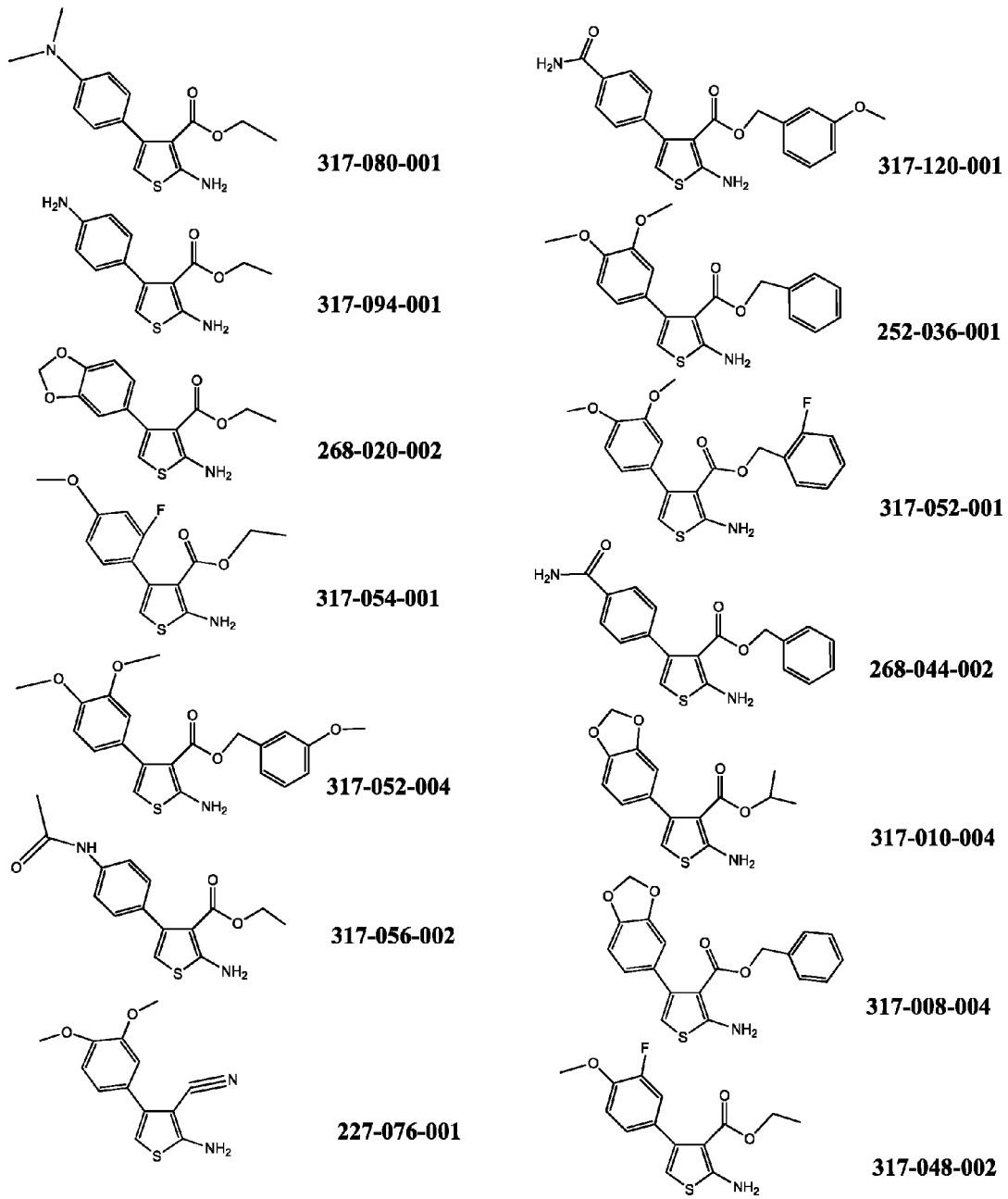
FIG. 7 depicts chemical structures of compounds assayed for aPKC inhibitory activity.

$IC_{50}$ values were determined using an in vitro luminescence-based kinase assay against aPKCζ to elucidate a pharmacophore. The $IC_{50}$ values determined for isopropyl 2-amino-4-(3,4-dimethoxyphenyl)thiophene-3-carboxylate (also referred to as PKCl-diMeO, PKCζl-diMeO, or PKCzl3), and compounds described herein and illustrated in FIGS. 1, 3, and 7 are described in Table 1. The $IC_{50}$ values were determined using an ADP Quest™ assay with 500 ng/ml aPKCζ, 10 μM CREBtide, and 10 μM ATP. In PKCζ kinase activity assays using 30 μM of candidate compound, PKCl-diMeO and the compounds illustrated in FIG. 7 resulted in a 55-100% inhibition in kinase activity.

TABLE 1

| COMPOUND | $IC_{50}$ (μM) |
|---|---|
| PKCzI-diMeO | 6 |
| 317-080-001 | 1 |
| 317-094-001 | 2 |
| 268-020-002 | 2 |
| 317-054-001 | 4 |
| 317-052-004 | 5 |
| 317-056-002 | 6 |
| 317-120-001 | 6 |
| 252-036-001 | 6 |
| 227-076-001 | 7 |
| 317-052-001 | 7 |
| 268-044-002 | 11 |
| 317-010-004 | 21 |
| 317-008-004 | 20 |
| 317-048-002 | 17 |
| 194-074-007 | 35 |
| 194-074-005 | 4 |
| 194-074-008 | 4 |
| 194-094-008 | 5 |
| 194-094-003 | 3 |
| 194-094-009 | 5 |

Figure 6:
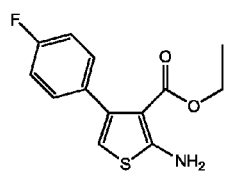
FIG. 6 depicts chemical structures of compounds assayed for aPKC inhibitory activity.
Figure 6:
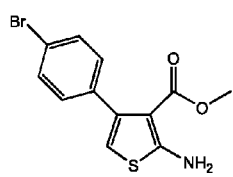
Figure 6:
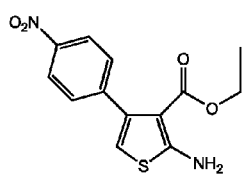
Figure 6:
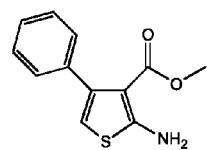
Figure 6:
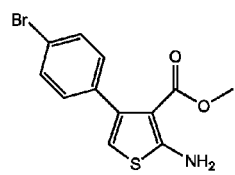
Figure 6:
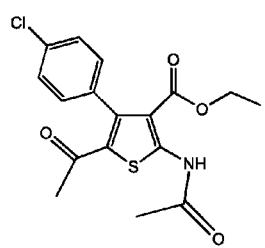
Figure 6:
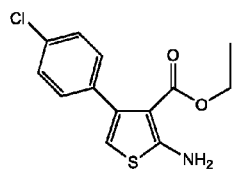

The $IC_{50}$ values for PKCl-diMeO and compounds described herein and illustrated in FIG. 6 are described in Table 2. The $IC_{50}$ values were determined using a Kinase-Glo® end-point assay with 125 ng/ml aPKCζ, 25 μM CREBtide, and 0.1 μM ATP.

TABLE 2

| COMPOUND | $IC_{50}$ (μM) |
|---|---|
| PKCl-diMeO | 20 |
| 5132573 | 26 |
| 5311310 | 41 |
| 5627112 | 28 |
| APOGEE A | 39 |
| 5632675 | 24 |
| 5635527 | 62 |
| APOGEE B | 71 |

Figure 8A:
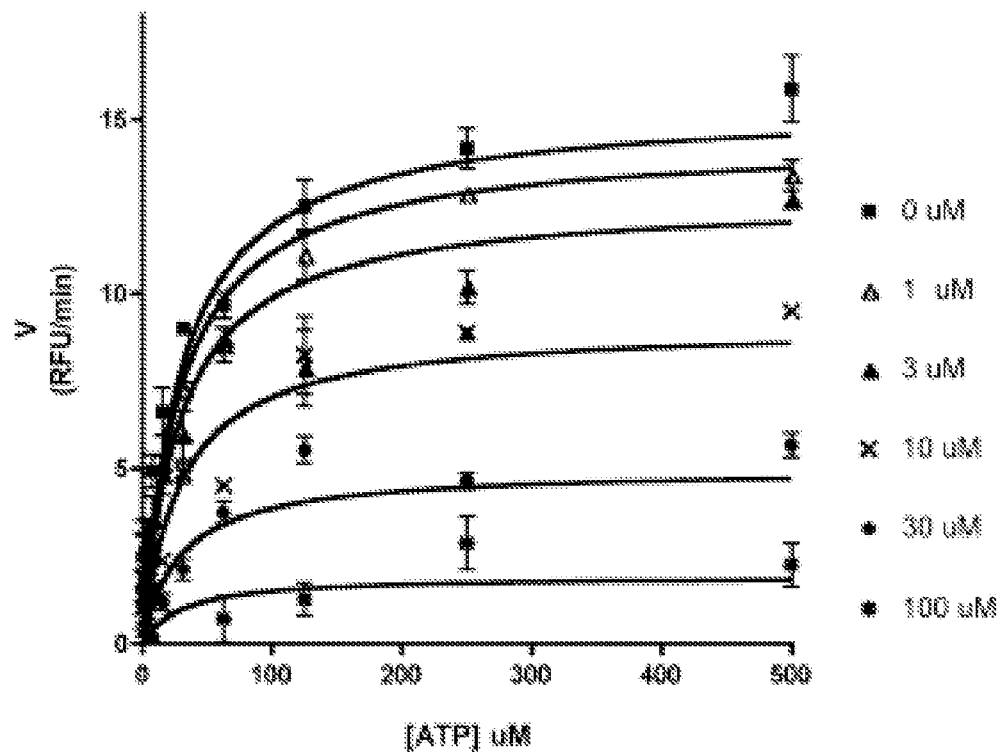
FIGS. 8A and 8B are graphs summarizing ADP Quest™ test results for PKCl-diMeO in ATP competition assays. Concentrations of Crebtide substrate or ATP are provided on the X-axis, and velocity (RFU/minute) is provided on the Y-axis. PKCl-diMeO was tested at concentrations from 0 µM to 30 µM.
Figure 8B:
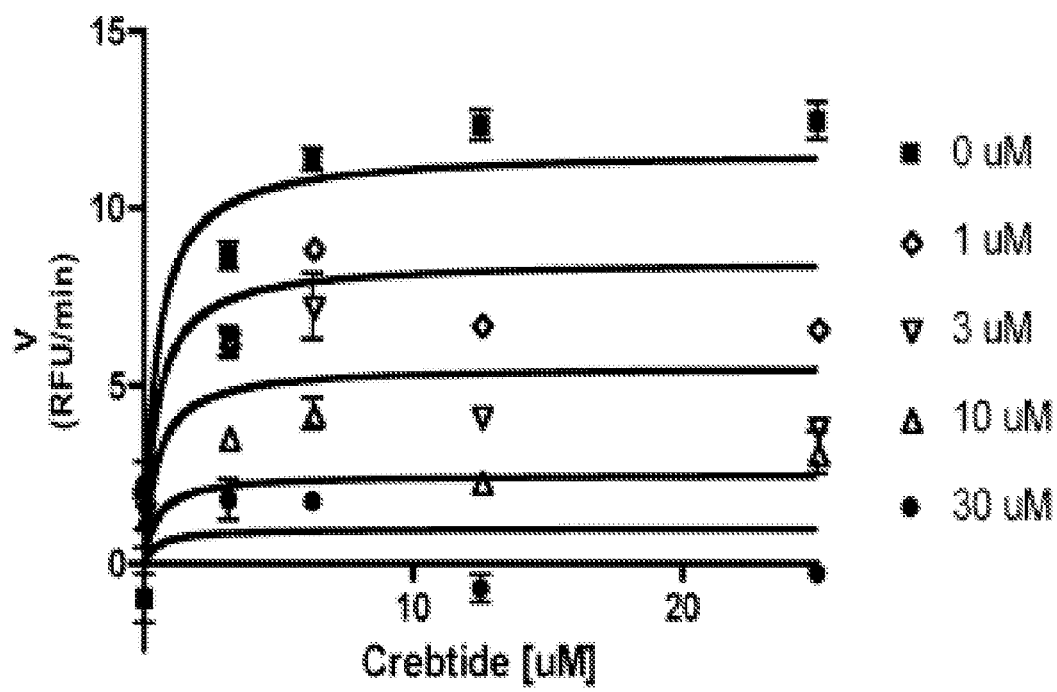

PKCl-diMeO was selected for competition assays to determine the mechanism of action due to the compound's improved solubility in aqueous environments. By measuring ADP formation under increasing ATP concentrations at various doses of inhibitor, it was determined that PKCl-diMeO significantly altered $V_{max}$ without affecting $K_m$ with a $K_i$ of about 7±5 μM (FIG. 8A). Furthermore, a similar competition assay was performed against CREBtide, a short peptide mimicking a PKC substrate, and the peptide substrate also failed to compete the PKCl-diMeO inhibitor and restore $V_{max}$ (FIG. 8B). Therefore, 2-amino-4-phenyl-thiophenes are non-competitive inhibitors of PKCζ. Similar assays were performed with other compounds described herein and depicted in FIGS. 1 and 3. The results of the assays are illustrated in FIGS. 2A, 2B, 4A, 4B, 5A, and 5B.

Figure 9:
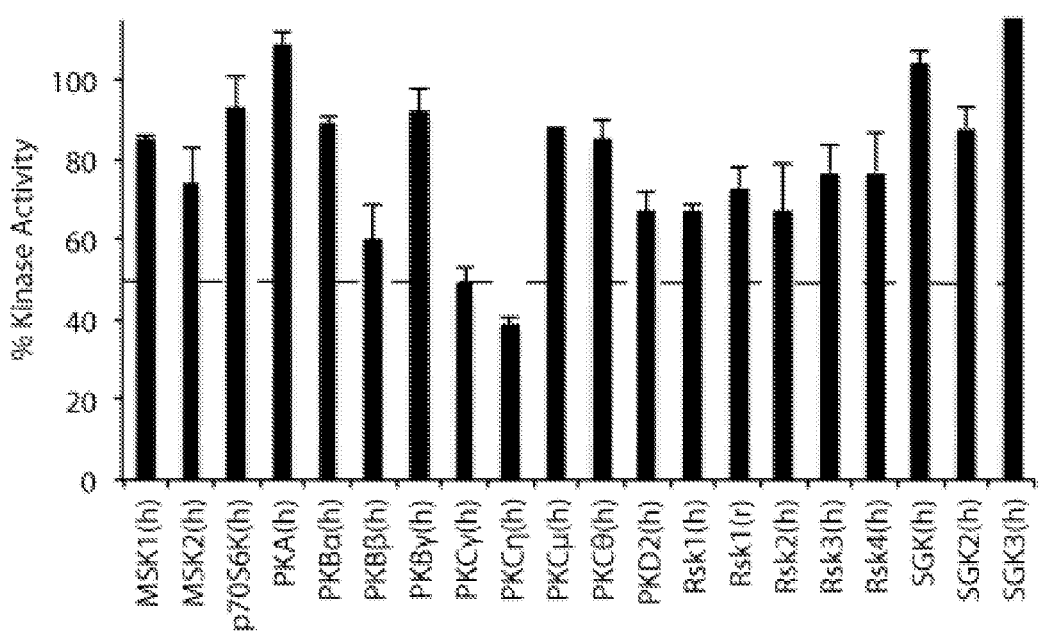
FIG. 9 is a bar graph illustrating the specificity of PKCl-diMeO for aPKCs. AGC superfamily kinases are provided on the X-axis and % kinase activity is provided on the Y-axis.

PKCldiMeO and PKCζl-diCl were screened against other PKC isoforms to determine class specificity using a radio-labeled kinase assay at the $K_{mapp}$ for ATP. $IC_{50}$ values were determined for PKCl-diMeO against the other PKC isoforms: PKCα $IC_{50}$ 282 µM; PKCβ $IC_{50}$ 124 µM; PKCδ $IC_{50}$ 147 µM; PKCε $IC_{50}$>100 µM; and PKCι $IC_{50}$ 5 µM. PKCζl-diCl was 5-10 fold more specific towards the atypical PKC isoforms compared to the classical PKCs (α, β) and over 10-20 fold more specific compared to the novel class (δ,ε). PKCl-diMeO improved on specificity against the classical PKC isoforms and was 25-50 fold more specific towards the aPKC isoform (ι) compared to the cPKCs (α,β) and 25-fold more specific compared to nPKCs (δ,ε). The compounds did not exhibit specificity within the atypical PKC class with similar $IC_{50}$ values for PKC and PKCζ. To determine if PKCl-diMeO possessed significant inhibitor activity towards other kinases, 20 AGC super-family kinases sharing the most similar sequence homology to PKCs, were screened at 100 µM, 2.5 fold the $K_i$ for aPKC isoforms. PKCl-diMeO demonstrated limited inhibitory activity to these other kinases with only a modest reduction in two other PKC isoforms tested (FIG. 9). Additionally, PKCl-diMeO did not inhibit cPKC activity in cell culture. Erk phosphorylation, which is downstream of cPKC in endothelial cells, was unaffected by PKCl-diMeO treatment. Furthermore, AKT, a downstream mediator of PI3K signaling in endothelial cells was also unaffected with PKCl-diMeO treatment. Finally, PKCl-diMeO inhibited an active kinase fragment devoid of regulatory domains (amino acids 211-592) of PKCζ as effectively as it inhibited full-length PKCζ demonstrating it acted within this region of the kinase. Collectively, the studies demonstrated that phenyl-thiophene derivatives are potent inhibitors of aPKC isoforms with high specificity.

Figure 10:
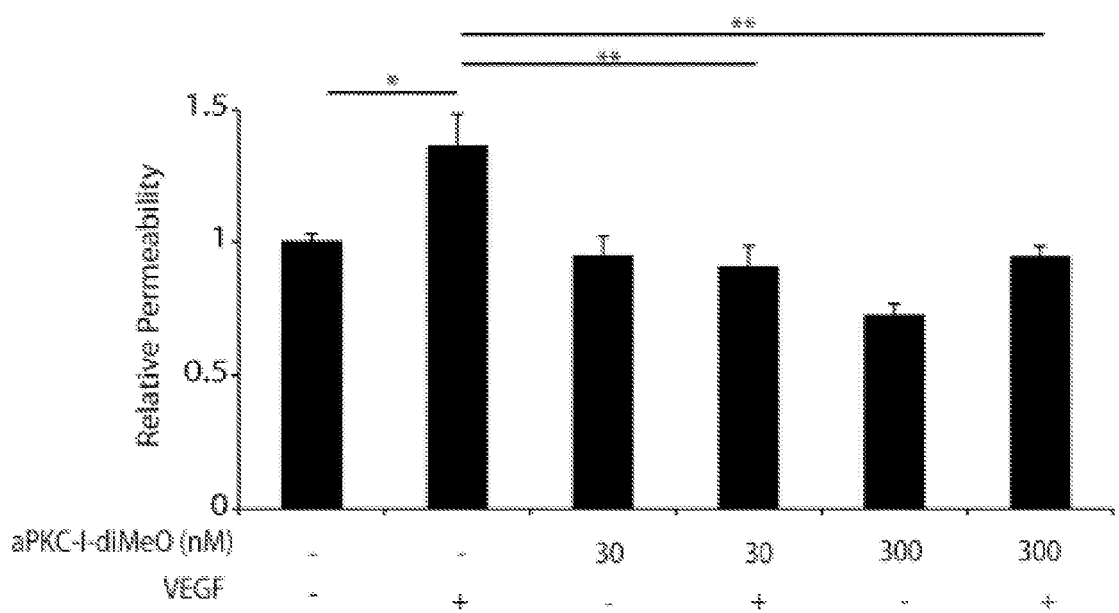
FIG. 10 is a bar graph correlating concentrations of PKCl-diMeO and VEGF (X-axis) with the relative permeability of a BREC monolayer to 70 kDa RITC-Dextran (Y-axis) determined in a VEGF-induced retinal endothelial permeability assay.

Phenyl-Thiophenes Prevent VEGF-Induced and TNF/VEGF-Induced Vascular Endothelial Permeability The effectiveness of phenyl-thiophenes in preventing VEGF-induced increases in endothelial permeability was determined. Primary BREC were grown to confluence on 0.4 µm Transwell filters and pretreated with 30 nM or 100 nM of PKCζl-diCl or 30 nM or 300 nM of PKCl-diMeO 30 minutes prior to 30 minutes of treatment with 50 ng/ml VEGF. PKCζl-diCl dose-dependently blocked VEGF-induced permeability in BREC. PKCζl-diMeO also dose-dependently blocked VEGF-induced endothelial permeability in BREC (FIG. 10). Measures of BREC viability at 24 and 48 hours revealed no evidence of cell death after treatment with PKCl-diMeO at up to 300 nM. To measure inhibition of TNF/VEGF-induced retinal endothelial permeability, BREC cells were pre-treated with PKCl-diMeO and other compounds described herein and illustrated in FIG. 7 for 30 minutes. The cells were then treated with TNFα for 1 hour followed by VEGF for 30 minutes. Permeability to 70 kDa RITC-Dextran was measured over 4 hours, starting 30 minutes following addition of VEGF. PKCl-diMeO and piperonyl-substituted phenyl-thiophene (Compound 268-020-002 in FIG. 7) were able to significantly reduce the TNF/VEGF-induction of BREC permeability. The $EC_{50}$ for inhibition of TNF/VEG-induced endothelial permeability was 1 nM for PKCl-diMeO and 20 nM for Compound 268-020-002. Other compounds tested exhibited inhibition of TNF/VEGF-induced retinal endothelial permeability, but to a lesser degree.

To further examine the role of aPKC isoforms on steady state barrier regulation, a dose-response curve with aPKC inhibitors was performed. BREC were plated on Transwell filters as above and treated with PKCζ-PD at doses ranging from 10 to 0.1 µM for 30 min prior to the addition of the fluorescent tracer. The compound significantly decreased the permeability of the BREC monolayer at a dose as low as 1 µM. The basal effect of reducing permeability was also observed in human retinal endothelial primary cells (HREC) monolayers with the PKCζl-diCl molecule. The data demonstrated aPKC isoforms play an important role in barrier homeostasis in endothelial monolayers.

aPKC Inhibition Prevents Disorganization of Tight Junctions Proteins Following VEGF Treatment VEGF treatment of retinal endothelial cells and diabetes leads to a breakdown of the tight junction complex and internalization of tight junction proteins occludin and ZO-1. The ability of the phenyl-thiophene derivatives to prevent the VEGF-induced reduction in tight junction border staining was examined. BREC were grown to confluence on coverslips and pretreated with 100 nM PKCζ-diCl for 30 minutes prior to treatment with 50 ng/ml VEGF for 60 minutes. Cells were fixed and stained with antibodies for ZO-1 or occludin and were visualized by confocal microscopy. VEGF decreased the border staining and continuity of ZO-1 and occludin labeling at the cell border. Pretreatment of cells with PKCζ inhibitors (PKCζls) blocked the VEGF-induced redistribution of occludin and ZO-1 proteins as evidenced by preserved continuous border staining. This effect on the tight junction correlated with the observed attenuation of VEGF-induced permeability.

PKCζls Block the VEGF Induction of Retinal Vascular Permeability In Vivo

To determine if PKCζls block retinal vascular permeability in vivo, the ability of PKCζls to block the VEGF-induced extravasation of Evan's blue dye in the retina was examined. Sprague-Dawley rats (150-175 g) received 5 µl intra-vitreal injections of either PBS, or a final estimated vitreous concentration of 25 µM PKCζl-diCl, 50 ng VEGF, or PKCζl plus VEGF as indicated. Treatment with VEGF caused an approximate 50-60% increase in accumulation of Evan's blue in the retina. Administration of 25 µM PKCζl prevented this effect and yielded measures that were not statistically different from controls.

To determine the effects of VEGF injection and aPKC isoform inhibition on the retinal vasculature tight junction complex, retinal flat mounts were prepared and immuno-labeled with occludin following the intra-vitreal injection of VEGF and/or PKCζl-diCl. In vehicle-injected eyes, occludin border staining was intense and continuous; however, upon VEGF treatment, the immuno-reactivity was decreased and a discontinuous border-staining pattern was observed. Upon PKCζl-diCl co-injection, occludin border staining was preserved and overall immuno-reactivity was increased. These results combined with the cell culture studies demonstrate that inhibiting aPKC isoforms in retinal endothelial cells prevented VEGF-induced retinal vascular permeability Atypical PKC Inhibition Prevents TNF-Induced NF-kB Activation Human embryonic kidney cells containing a luciferase reporter gene for NF-kB activation (HEK293pNF-kBluc) were treated with candidate compounds described herein for three hours. The cells were then stimulated with TNF for five hours and the inhibition of NF-kB was evaluated. After pretreatment with 100 nM of aPKC inhibitor, NF-kB activity was reduced by as much as 80%. $EC_{50}$ values were determined for PKCl-diMeO and other compounds described herein and illustrated in FIG. 7 using 100 nM of aPKCζ inhibitor and 5 ng/mL TNF: PKCl-diMeO $EC_{50}$ 3 nM; 317-080-001 $EC_{50}$ 1 nM; 317-094-001 $EC_{50}$ 1 nM; 268-020-002 $EC_{50}$ 3 nM; 317-054-001 $EC_{50}$ 10 nM; 317-052-004 $EC_{50}$ 2 nM; 252-036-001 $EC_{50}$ 1 nM. Other compounds tested inhibited TNF-induced NF-kB activity, but to a lesser degree.

SUMMARY aPKC isoforms directly associate and co-localize with the apical tight junction complex of mammalian cells, supporting their role in barrier regulation. Calcium deprivation assays to monitor de novo barrier formation in mammalian epithelial cells demonstrates that PKCζ is required for junction assembly. In this regard, a kinase-dead PKCζ prevents barrier assembly and leads to permeability of 40 kDa-dextran molecules following calcium deprivation (Suzuki et al., *J Cell Biol*, 152:1183-1196 (2001)). The data described above demonstrates involvement of aPKC isoforms in the regulation of the endothelial tight junction complex and in controlling vascular permeability induced by VEGF. The compounds identified as described herein demonstrated low μM potency for aPKC accompanied by low toxicity in primary endothelial cells consistent with the relatively normal PKCζ knockout mouse phenotype. The compounds are non-competitive in regards to ATP and substrate pocket and exhibit selectivity for aPKCs within the PKC family. The identified phenylthiophenes further exhibit in vivo efficacy and block VEGF-induced and TNF/VEGF-induced retinal permeability in the rat eye, a clinically-relevant animal model. The compounds are potent at inhibiting PKC in kinase assays. The compounds and methods disclosed herein inhibit vascular permeability and aPKC and represent novel therapies to inhibit, e.g., metabolic disorders, inflammation, cancer cell proliferation, and angiogenesis.

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed:

1. A method of inhibiting or reducing vascular permeability comprising:
administering to a subject in need thereof a composition comprising a compound in an amount effective to inhibit or reduce vascular permeability, the compound having a structure selected from the group consisting of structural formula (I) to (VIII):

structural formula (I):

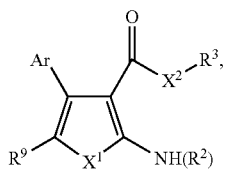

(I)

structural formula (II):

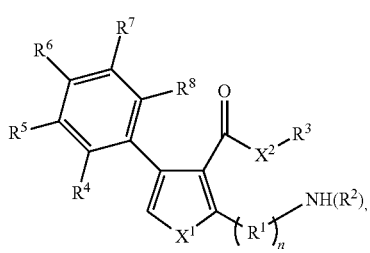

(II)

structural formula (III):

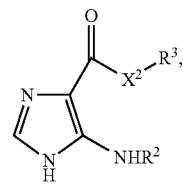

(III)

structural formula (IV):

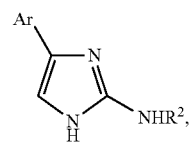

(IV)

structural formula (V):

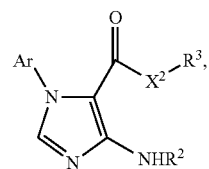

(V)

structural formula (VI):

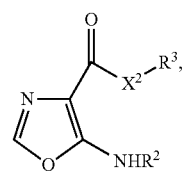

(VI)

structural formula (VII):

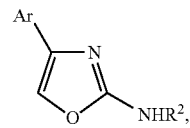

(VII)

and structural formula (VIII):

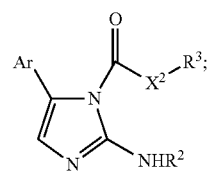

(VIII)

wherein $X^1$ is selected from the group consisting of O, S, NH, and NMe;

wherein n has a value of zero (0), one (1), or two (2);
wherein $R^1$ is selected from the group consisting of $CH_2$, $CH(CH_3)$, $C(CH_3)_2$, $C_2H_4$, and $C_2H_2$;
wherein $R^2$ is selected from the group consisting of H, $CH_3$, $CH_2OH$, $C_2H_5$, $C_2H_5O$, $CH(CH_3)_2$, $C(CH_3)$, $CH_2CH(CH_3)_2$, and $CH_2C(CH_3)_3$;
wherein $X^2$ is selected from the group consisting of O, S, NH and N; when $X^2$ is O, S, or NH, $R^3$ is selected from the group consisting of an aryl residue, an alkyl residue having 1 to 10 carbon atoms, an alkoxy residue having 1 to 10 carbon atoms, and a polyglycol residue having two to twelve carbon atoms; when $X^2$ is N, $R^3$ is either two independently selected residues each selected from the group consisting of an aryl residue, an alkyl residue having 1 to 10 carbon atoms, an alkoxy residue having 1 to 10 carbon atoms, and a polyglycol residue having two to twelve carbon atoms; or $X^2$ and $R^3$ are a cyclic group ($X^2$—$R^3$) having five or six members and optionally one or more additional heteroatoms;
wherein $R^4$ and $R^8$ are individually selected from the group consisting of H, F, Cl, OH, and $OCH_3$;
wherein $R^5$ and $R^7$ are individually selected from the group consisting of H, F, Cl, Br, $CH_3$, $C_2H_5$, OH, $OCH_3$, $OCH_2CH_3$, $OCH_2OCH_3$, $S(CH_3)_2^+$, and $N(alkyl)_3^+$;
wherein $R^6$ is selected from the group consisting of H; F; Cl; Br; $CH_3$; $C_2H_5$; $NO_2$; OH; $OCH_3$; $OCH_2CH_3$; $OCH_2OCH_3$; $OCH_2CH_2OH$; $OCH_2CH_2OCH_3$; $OCH_2CH_2OCH_2CH_3$; polyglycol residue selected from the group consisting of methylene glycols, ethylene glycols, propylene glycols and mixtures thereof; and an aryl group;
wherein Ar is selected from the group consisting of phenyl, napthyl, pyridyl, pyrrolidyl, furanyl, pyranyl, azepinyl, oxepinyl, imidizolyl, oxazolyl, pyrimidinyl, purinyl, dimethoxyphenyl, chlorophenyl, dichlorophenyl, bromophenyl, hydroxyphenyl, trimethylphenyl, fluorophenyl, nitrophenyl, methoxyphenyl, dihydrobenzopyran, pyridine, dimethyl aminophenyl, aminophenyl, piperonyl, fluoromethoxyphenyl, acetamidophenyl, and carbomoylphenyl;
wherein $R^9$ is selected from the group consisting of H, $CH_3$, $CH_2N(CH_3)_2$, and phenyl;
wherein when either $R^5$ or $R^7$ is Cl and the other is H, $R^6$ is not Cl; and
wherein the compound is not isopropyl 2-amino-4-(3,4-dichlorophenyl)thiophene-3-carboxylate.

2. A method of inhibiting or reducing vascular permeability comprising:
administering to a subject in need thereof a composition comprising a compound in an amount effective to inhibit or reduce vascular permeability, the compound having structural formula (IX):

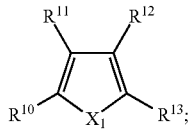

(IX)

wherein $X^1$ is selected from the group consisting of O, S, NH, and NMe;
wherein $R^{10}$ is selected from the group consisting of H, $CH_3$, $COCH_3$, and $C_5H_{10}N$;
wherein $R^{11}$ is selected from the group consisting of phenyl, chlorophenyl, dichlorophenyl, dimethylaminophenyl, aminophenyl, piperonyl, dimethoxyphenyl, methoxyphenyl, acetamidophenyl, carbomoylphenyl, fluoromethoxyphenyl, napthyl, pyridyl, pyrrolidyl, furanyl, pyranyl, azepinyl, oxepinyl, imidizolyl, oxazolyl, pyrimidinyl, purinyl, and substituted groups thereof;
wherein $R^{12}$ is selected from the group consisting of an aryl ester carboxylate, an alkyl ester carboxylate, an alkoxy ester carboxylate, an aryl carboxamide, an alkyl carboxamide, an alkoxy carboxamide, $C_2H_4NO$, and nitrile;
wherein $R^{13}$ is selected from the group consisting of $NH_2$, $C_2H_3O$, $C_7H_4N_2O_3Cl$, $C_7H_4NOClF$, $C_6H_4N_2O_3Cl$, and $C_2H_4NO$;
wherein when $R^{10}$ is $CH_3$, $R^{13}$ is not $C_2H_4NO$; and
wherein when $R^{12}$ is isopropyl carboxylate, $R^{11}$ is not 3,4-dichlorophenyl.

3. The method of claim 1, wherein the vascular permeability is associated with a disease or disorder characterized by abnormal vascular permeability selected from the group consisting of macular edema, diabetic retinopathy, retinopathy of prematurity, age-related macular degeneration, uveitis, branch retinal vein occlusion, central retinal vein occlusion, ischemia-reperfusion injury, neoplasic disease, and brain edema.

4. The method of claim 1, wherein $X^1$ is S; $X^2$ is O; n has a value of zero (0); and $R^2$ is H.

5. The method of claim 1, wherein $R^3$ is an aryl residue or an alkyl residue having 1 to 10 carbons; and $R^4$ and $R^8$ are H.

6. The method of claim 1, wherein $R^7$ is H; and $R^5$ is selected from the group consisting of H, F, Cl, Br, $CH_3$, $C_2H_5$, OH, $OCH_3$, $OCH_2CH_3$, $OCH_2OCH_3$, $S(CH_3)^+$, and $N(alkyl)_3^+$.

7. The method of claim 1, wherein $R^6$ is selected from the group consisting of H, F, Cl, Br, $CH_3$, $C_2H_5$, $NO_2$, OH, $OCH_3$, $OCH_2CH_3$, $OCH_2CH_2OH$, $OCH_2CH_2OCH_3$, and $OCH_2CH_2OCH_2CH_3$.

8. The method of claim 1, wherein $R^5$ is selected from the group consisting of H, $OCH_3$, and $OCH_2CH_3$; $R^6$ is selected from the group consisting of OH, $OCH_3$, $OCH_2CH_3$, $OCH_2CH_2OH$, $OCH_2CH_2OCH_3$, and $OCH_2CH_2OCH_2CH_3$; and $R^7$ is H.

9. The method of claim 1, wherein $R^5$ is $OCH_3$; $R^6$ is $OCH_3$; and $R^7$ is H.

10. The method of claim 1, wherein $R^9$ is selected from the group consisting of H, $CH_3$, and $CH_2N(CH_3)_2$.

11. The method of claim 1, wherein Ar is selected from the group consisting of phenyl, dimethoxyphenyl, chlorophenyl, dichlorophenyl, bromophenyl, hydroxyphenyl, trimethylphenyl, fluorophenyl, nitrophenyl, methoxyphenyl, dihydrobenzopyran, or pyridine.

12. The method of claim 11, wherein $X^1$ is S; $X^2$ is O; n has a value of zero (0), $R^2$ is H, $R^3$ is $CH(CH_3)_2$, $R^9$ is H, and Ar is a dimethoxyphenyl group.

13. The method of claim 1, wherein the compound has a structure of structural formula (I).

14. The method of claim 13, wherein Ar is selected from the group consisting of dimethoxyphenyl, chlorophenyl, dichlorophenyl, bromophenyl, hydroxyphenyl, trimethylphenyl, fluorophenyl, nitrophenyl, methoxyphenyl, dihydrobenzopyran, and pyridine.

15. The method of claim 14, wherein Ar is dimethoxyphenyl.

16. The method of claim 1, wherein the compound has a structure of structural formula (II).

* * * * *